(12) United States Patent
Ko

(10) Patent No.: US 10,396,296 B2
(45) Date of Patent: Aug. 27, 2019

(54) ORGANIC LIGHT-EMITTING DEVICE

(71) Applicant: SAMSUNG DISPLAY CO., LTD., Yongin-si, Gyeonggi-do (KR)

(72) Inventor: Heejoo Ko, Yongin-si (KR)

(73) Assignee: Samsung Display Co., Ltd., Yongin-Si, Gyeonggi-do (KR)

( * ) Notice: Subject to any disclaimer, the term of this patent is extended or adjusted under 35 U.S.C. 154(b) by 256 days.

(21) Appl. No.: 15/602,581

(22) Filed: May 23, 2017

(65) Prior Publication Data

US 2018/0019408 A1 Jan. 18, 2018

(30) Foreign Application Priority Data

Jul. 13, 2016 (KR) .................. 10-2016-0088853

(51) Int. Cl.
| | |
|---|---|
| *H01L 51/00* | (2006.01) |
| *C07C 211/54* | (2006.01) |
| *C07D 209/86* | (2006.01) |
| *H01L 51/50* | (2006.01) |
| *H01L 51/52* | (2006.01) |

(52) U.S. Cl.
CPC ........ *H01L 51/0072* (2013.01); *C07C 211/54* (2013.01); *C07D 209/86* (2013.01); *H01L 51/0059* (2013.01); *H01L 51/5004* (2013.01); *H01L 51/5056* (2013.01); *H01L 51/5278* (2013.01); *C07C 2601/14* (2017.05); *H01L 51/504* (2013.01); *H01L 51/508* (2013.01); *H01L 51/5206* (2013.01); *H01L 51/5221* (2013.01); *H01L 2251/301* (2013.01); *H01L 2251/303* (2013.01); *H01L 2251/552* (2013.01)

(58) Field of Classification Search
None
See application file for complete search history.

(56) References Cited

U.S. PATENT DOCUMENTS

| | | | |
|---|---|---|---|
| 6,717,358 | B1 | 4/2004 | Liao et al. |
| 7,273,663 | B2 | 9/2007 | Liao et al. |
| (Continued) | | | |

FOREIGN PATENT DOCUMENTS

| | | |
|---|---|---|
| KR | 10-2007-0043014 A | 4/2007 |
| KR | 10-2008-0105640 A | 12/2008 |
| (Continued) | | |

*Primary Examiner* — Robert S Loewe
(74) *Attorney, Agent, or Firm* — Lee & Morse, P.C.

(57) ABSTRACT

An organic light-emitting device includes electrodes and light-emitting units that each include an emission layer; and a charge generation layer, including n- and p-type charge generation layers, disposed between each adjacent pair of light-emitting units. A wavelength of maximum intensity of light emitted from one of the light-emitting units may be different from another, an n-type charge generation layer may have a metal-containing material having a work function of about 2.0 eV to about 4.5 eV, and a p-type charge generation layer may be formed of a hole transport material, an absolute value of a HOMO energy level of the hole transport material being greater than about 5.5 eV, and an absolute value of a LUMO energy level of the hole transport material being less than that of a LUMO energy level of a hole transport layer of a light-emitting unit adjacent to the p-type charge generation layer.

20 Claims, 6 Drawing Sheets

(56) References Cited

U.S. PATENT DOCUMENTS

| | | | |
|---|---|---|---|
| 7,696,681 B2* | 4/2010 | Park | H01L 27/3209 313/503 |
| 7,816,859 B2* | 10/2010 | Spindler | C09K 11/06 313/504 |
| 7,859,186 B2 | 12/2010 | Noh et al. | |
| 8,080,934 B2* | 12/2011 | Kido | C07C 211/58 313/504 |
| 8,373,191 B2 | 2/2013 | Ide et al. | |
| 8,476,624 B1* | 7/2013 | Wu | H01L 51/5004 257/40 |
| 8,564,190 B2* | 10/2013 | Seo | C09K 11/06 313/504 |
| 8,680,693 B2* | 3/2014 | Kang | H01L 27/3209 257/40 |
| 9,012,902 B2* | 4/2015 | Ide | H01L 51/5044 257/40 |
| 9,070,884 B2* | 6/2015 | Tung | C09K 11/06 |
| 9,105,861 B2* | 8/2015 | Jung | H01L 51/5044 |
| 9,276,221 B2* | 3/2016 | Nowatari | H01L 51/0078 |
| 9,356,242 B2* | 5/2016 | Kaiser | H01L 51/0067 |
| 9,356,249 B2* | 5/2016 | Chang | H01L 51/5008 |
| 9,455,415 B2* | 9/2016 | Kim | H01L 27/32 |
| 2003/0170491 A1* | 9/2003 | Liao | H01L 51/5036 428/690 |
| 2006/0040132 A1* | 2/2006 | Liao | H01L 51/5036 428/690 |
| 2009/0102366 A1* | 4/2009 | Ushikubo | C09K 11/06 313/504 |
| 2010/0148166 A1* | 6/2010 | Ushikubo | C09K 11/06 257/40 |
| 2011/0240972 A1* | 10/2011 | Nowatari | H01L 51/0078 257/40 |
| 2011/0248249 A1* | 10/2011 | Forrest | H01L 51/5016 257/40 |
| 2011/0315968 A1* | 12/2011 | Nowatari | H01L 51/0078 257/40 |
| 2012/0119197 A1* | 5/2012 | Nishimura | C07D 209/86 257/40 |
| 2013/0256637 A1* | 10/2013 | Seo | H01L 51/5004 257/40 |
| 2013/0264551 A1* | 10/2013 | Pieh | H01L 51/5056 257/40 |
| 2014/0084269 A1* | 3/2014 | Weaver | H01L 27/3209 257/40 |
| 2014/0117338 A1* | 5/2014 | Cho | H01L 51/5044 257/40 |
| 2014/0159023 A1* | 6/2014 | Matsumoto | H01L 51/0061 257/40 |
| 2015/0034923 A1* | 2/2015 | Kim | H01L 51/5044 257/40 |
| 2015/0060825 A1* | 3/2015 | Song | H01L 51/5278 257/40 |
| 2015/0144897 A1* | 5/2015 | Kang | H01L 51/5076 257/40 |
| 2015/0287949 A1* | 10/2015 | Okamoto | H01L 51/5004 257/40 |
| 2015/0340635 A1* | 11/2015 | Ahn | H01L 51/504 257/40 |
| 2016/0043327 A1* | 2/2016 | Yoo | H01L 51/504 257/40 |
| 2016/0118613 A1* | 4/2016 | Nam | H01L 51/5278 257/40 |
| 2016/0141502 A1* | 5/2016 | Joo | H01L 51/0052 257/40 |
| 2016/0164004 A1* | 6/2016 | Seo | H01L 27/3209 257/40 |
| 2016/0181563 A1* | 6/2016 | Cho | H01L 51/5024 257/40 |
| 2016/0285010 A1* | 9/2016 | Yoon | H01L 51/0072 |
| 2017/0054084 A1* | 2/2017 | Kim | H01L 51/0058 |

FOREIGN PATENT DOCUMENTS

| | | |
|---|---|---|
| KR | 10-2010-0068617 A | 6/2010 |
| KR | 10-2011-0043722 A | 4/2011 |

* cited by examiner

ORGANIC LIGHT-EMITTING DEVICE

CROSS-REFERENCE TO RELATED APPLICATION

Korean Patent Application No. 10-2016-0088853, filed on Jul. 13, 2016, in the Korean Intellectual Property Office, and entitled: "Organic Light-Emitting Device," is incorporated by reference herein in its entirety.

BACKGROUND

1. Field

Embodiments relate to an organic light-emitting device.

2. Description of the Related Art

Organic light-emitting devices are self-emission devices that may be used to produce full-color images, and may provide displays having wide viewing angles, high contrast ratios, and short response times, as well as excellent characteristics in terms of brightness, driving voltage, and response speed.

As an example, such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state, thereby generating light.

SUMMARY

Embodiments are directed to an organic light-emitting device, including a first electrode, a second electrode facing the first electrode, and a plurality of light-emitting units disposed in a stack between the first and second electrodes, each light emitting unit including an emission layer, and a charge generation layer, including an n-type charge generation layer and a p-type charge generation layer, disposed between each adjacent pair of light-emitting units. A wavelength of maximum intensity of light emitted from one of the light-emitting units may be different from the wavelength of maximum intensity of light emitted from another of the light-emitting units, at least one n-type charge generation layer may consist of a metal-containing material having a work function of about 2.0 eV to about 4.5 eV, the metal-containing material being a metal, a metal oxide, a metal halide, or a combination thereof, and at least one p-type charge generation layer may include a hole transport material, at least one light-emitting unit adjacent to the p-type charge generation layer including the hole transport material includes a hole transport region, the hole transport region includes a hole transport layer, an absolute value of a highest occupied molecular orbital (HOMO) energy level of the hole transport material being greater than about 5.5 eV, and an absolute value of a lowest unoccupied molecular orbital (LUMO) energy level of the hole transport material being less than that of a LUMO energy level of a hole transport layer of a light-emitting unit adjacent to the p-type charge generation layer.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
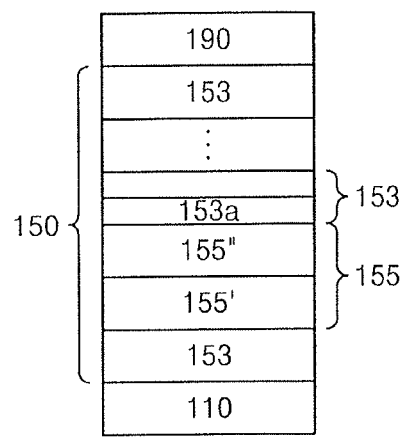
FIGS. 1 to 5 illustrate schematic diagrams of a structure of an organic light-emitting device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an example embodiment, an organic light-emitting device according to an embodiment may include:

a first electrode;

a second electrode facing the first electrode;

m light-emitting units disposed between the first electrode and the second electrode and including at least one emission layer; and m−1 charge generation layer(s) disposed between two adjacent light-emitting units among m light-emitting units and including an n-type charge generation layer and a p-type charge generation layer, wherein m represents an integer of 2 or greater, a wavelength of maximum intensity of light emitted from at least one selected from m light-emitting units is different from that of light emitted from at least one selected from the remaining light-emitting units, at least one selected from m−1 n-type charge generation layer(s) consists of a metal-containing material, the metal-containing material has a work function in a range from about 2.0 to about 4.5 eV, the metal-containing material is a metal, a metal oxide, a metal halide, or a combination thereof, at least one selected from m−1 p-type charge generation layer(s) includes a hole transport material, at least one light-emitting unit adjacent to the p-type charge generation layer including the hole transport material includes a hole transport region, the hole transport region includes a hole transport layer, an absolute value of a highest occupied molecular orbital (HOMO) energy level of the hole transport material of the p-type charge generation layer is greater than about 5.5 eV, and an absolute value of a lowest unoccupied molecular orbital (LUMO) energy level of the hole transport material of the p-type charge generation layer is less than that of a LUMO energy level of the hole transport layer of at least one light-emitting unit adjacent to the p-type charge generation layer.

FIG. 1 is a schematic view of an organic light-emitting device 10 according to an embodiment. In FIG. 1, the organic light-emitting device 10 includes a first electrode 110, a second electrode 190 facing the first electrode 110, m light-emitting units 153 (m being greater than or equal to 2) disposed between the first electrode 110 and the second electrode 190, and m−1 charge generation layer(s) 155 disposed between two adjacent light-emitting units 153 among m light-emitting units 153 and including an n-type charge generation layer 155' and a p-type charge generation layer 155".

The light-emitting unit may include, for example, one or more emission layers. In some embodiments, the light-emitting unit may further include an organic layer, in addition to the one or more emission layers.

The organic light-emitting device 10 may include m light-emitting units 153 stacked on top of one another, wherein m represents an integer of 2 or greater. m, which represents the number of the light-emitting units 153, may be selected according to the intended device structure. For example, the organic light-emitting device 10 may include 2, 3, 4, or 5 light-emitting units 153.

In an embodiment, a maximum emission wavelength or wavelength of maximum intensity of light emitted from at least one selected from m light-emitting units 153 may be different from that of light emitted from at least one selected from the remaining light-emitting units 153. For example, in an organic light-emitting device 10 in which a first light-emitting unit and a second light-emitting unit are stacked in the stated order, a wavelength of maximum intensity of light emitted from the first light-emitting unit may be different from that of light emitted from the second light-emitting unit.

An emission layer included in each of the first light-emitting unit and the second light-emitting unit may have, for example, i) a single-layered structure formed of a single material, ii) a single-layered structure formed of a plurality of different materials, or iii) a multi-layered structure having a plurality of layers formed of a plurality of different materials. Accordingly, light emitted from the first light-emitting unit or light emitted from the second light-emitting unit may be single color light or mixed color light. For example, in an organic light-emitting device 10 in which a first light-emitting unit, a second light-emitting unit, and a third light-emitting unit are stacked in the stated order, a wavelength of maximum intensity of light emitted from the first light-emitting unit may be the same as that of light emitted from the second light-emitting unit, but may be different from that of light emitted from the third light-emitting unit. In another implementation, a wavelength of maximum intensity of light emitted from the first light-emitting unit, a wavelength of maximum intensity of light emitted from the second light-emitting unit, and a wavelength of maximum intensity of light emitted from the third light-emitting unit may be different from each other.

The organic light-emitting device 10 may include the charge generation layer 155 between two adjacent light-emitting units 153 among m light-emitting units 153.

The expression "adjacent" as used herein may refer to an arrangement relationship of closest layers among the layers, in which the closest layers are referred to as adjacent layers. For example, the expression "two adjacent light-emitting units" as used herein may refer to an arrangement relationship of two light-emitting units that are arranged the most closely to each other among a plurality of light-emitting units. The expression "adjacent" as used herein may refer to a case when two layers are physically in contact, or a case when another layer is disposed between two layers. For example, a light-emitting unit 153 adjacent to the second electrode 190 of the organic light-emitting device 10 may refer to the light-emitting unit 153 arranged closest to the second electrode 190 of the organic light-emitting device 10 among a plurality of the light-emitting units 153.

In an embodiment, the second electrode 190 and the light-emitting unit 153 may be physically in contact, but in one or more embodiments, layers other than the light-emitting unit 153 may be disposed between the second electrode 190 and the light-emitting unit 153. For example, an electron transport layer may be disposed between the second electrode 190 and the light-emitting unit 153. In FIG. 1, the charge generation layer 155 is disposed between two adjacent light-emitting units 153.

The charge generation layer 155 as used herein may refer to a layer that serves as a cathode by generating an electron for one of the two adjacent light-emitting units 153 and serves as an anode by generating a hole for the other one of the two adjacent light-emitting units 153, wherein the charge generation layer 155 is not directly connected to the electrodes, but separates the light-emitting units 153 that are adjacent to each other. The organic light-emitting device 10 including m light-emitting units 153 may include m−1 charge generation layer(s) 155, for example, in an interleaved stack.

The charge generation layer 155 may include an n-type charge generation layer 155' and a p-type charge generation layer 155". Here, the n-type charge generation layer 155' may directly contact the p-type charge generation layer 155" to form an NP junction.

Through the NP junction, an electron and a hole may be generated at the same time between the n-type charge generation layer 155' and the p-type charge generation layer 155". The formed electron may be then transported to one of the two adjacent light-emitting units 153 via the n-type charge generation layer 155'. The formed hole may be then transported to the other one of the two adjacent light-emitting units 153 via the p-type charge generation layer 155".

The charge generation layer 155 may include one n-type charge generation layer 155' and one p-type charge generation layer 155", and thus, the organic light-emitting device 10 including m−1 charge generation layer(s) 155 may have m−1 n-type charge generation layer(s) 155' and m−1 p-type charge generation layer(s) 155".

The term "n-type" as used herein may refer to a characteristic of an n-type semiconductor, and that is, may refer to an electron injecting or transporting characteristic. The term "p-type" as used herein may refer to a characteristic of a p-type semiconductor, and that is, may refer to a hole injecting or transporting characteristic.

In an embodiment, at least one selected from m−1 n-type charge generation layer(s) may consist of a metal-containing material.

In an embodiment, the metal-containing material may have a work function in a range from about 2.0 eV to about 4.5 eV. In an embodiment, the metal-containing material may have a work function, for example, in a range from about 2.5 eV to about 4.0 eV, about 2.5 eV to about 3.0 eV, etc.

The metal-containing material may be a metal, a metal oxide, a metal halide, or a combination thereof.

In an embodiment, when at least one selected from m−1 n-type charge generation layer(s) includes a metal as the metal-containing material, examples of such a metal may include an alkali metal, an alkaline earth metal, a rare earth metal, a transition metal, a post-transition metal, and a combination thereof.

In an embodiment, when at least one selected from m−1 n-type charge generation layer(s) includes a metal oxide as the metal-containing material, an example of such a metal oxide includes an alkali metal oxide.

In an embodiment, when at least one selected from m−1 n-type charge generation layer(s) includes a metal halide as the metal-containing material, an example of such a metal halide includes an alkali metal halide.

In an embodiment, the metal-containing material may include at least one selected from ytterbium (Yb), silver (Ag), aluminum (Al), samarium (Sm), magnesium (Mg), lithium (Li), RbI, titanium (Ti), rubidium (Rb), sodium (Na), potassium (K), barium (Ba), manganese (Mn), and YbSi$_2$. In an embodiment, the metal-containing material may include at least one selected from Yb, Ag, and Al.

Referring to FIG. 1, at least one selected from m−1 p-type charge generation layer(s) 155" may include a hole transport material, and the light-emitting unit 153 adjacent to the p-type charge generation layer 155" including the hole transport material may include a hole transport region. The hole transport region may include a hole transport layer 153a. The p-type charge generation layer 155" including the hole transport material may be adjacent to the hole transport layer 153a.

In an embodiment, an absolute value of a lowest unoccupied molecular orbital (LUMO) energy level of the hole transport material of the p-type charge generation layer 155" may be less than that of a LUMO energy level of the hole transport layer of at least one light-emitting unit 153 adjacent to the p-type charge generation layer 155". In an embodiment, an absolute value of a LUMO energy level of the hole transport material of the p-type charge generation layer 155" may be about 2.8 eV or less.

In an embodiment, an absolute value of a highest occupied molecular orbital (HOMO) energy level of the hole transport material of the p-type charge generation layer may be the same as or greater than that of a HOMO energy level of the hole transport layer of the hole transport region of at least one light-emitting unit 153 adjacent to the p-type charge generation layer 155". In an embodiment, an absolute value of a HOMO energy level of the hole transport material of the p-type charge generation layer 155" may be greater than that of a HOMO energy level of the hole transport layer of the hole transport region of at least one light-emitting unit 153 adjacent to the p-type charge generation layer 155".

In an embodiment, an absolute value of a HOMO energy level of the hole transport material in the p-type charge generation layer 155" may be greater than about 5.5 eV. In an embodiment, an absolute value of a HOMO energy level of the hole transport material in the p-type charge generation layer 155" may be greater than about 5.5 eV, and may be about 7.0 eV or less. In an embodiment, an absolute value of a HOMO energy level of the hole transport material in the p-type charge generation layer 155" may be of greater than about 5.5 eV to about 6.0 eV or less.

In an embodiment, the hole transport material in the p-type charge generation layer 155" may be selected from compounds not including a cyano group and having an absolute value of a HOMO energy level greater than about 5.5 eV, but about 7.0 eV or less. For example, the hole transport material in the p-type charge generation layer 155" may be selected from an amine-containing compound and a carbazole-containing compound, each having an absolute value of a HOMO energy level greater than about 5.5 eV, but about 7.0 eV or less.

The term "amine-containing compound" as used herein may refer to a compound including at least one amine group, and examples thereof include a monoamine compound including one amine group and a diamine compound including two amine groups. The term "carbazole-containing compound" as used herein may refer to a compound having at least one carbazole group, and an example thereof includes a biscarbazole compound including two carbazole groups.

In an embodiment, the hole transport material may be selected from groups represented by Formulae 201, 202, and 301-2:

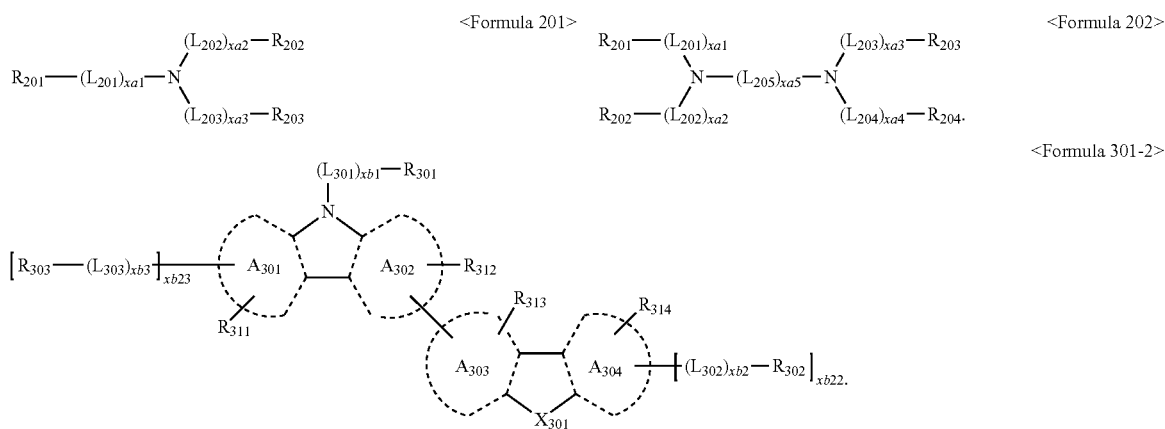

In Formulae 201, 202, and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or $N-[(L_{304})_{xb4}-R_{304}]$, $L_{201}$ to $L_{204}$ and $L_{301}$ to $L_{303}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N$(Q_{201})$-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, xb1 to xb4 may be an integer of 0 to 5, xb22 and xb23 may each independently be 0, 1, or 2, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{301}$ to $R_{304}$ may each independently be selected from deuterium, —F, —Cl, —Br, —I, a hydroxyl group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_{301})(Q_{302})(Q_{303})$, —N$(Q_{301})(Q_{302})$, —B$(Q_{301})(Q_{302})$, —C(=O)$(Q_{301})$, —S(=O)$_2(Q_{301})$, and —P(=O)$(Q_{301})(Q_{302})$, $R_{311}$ to $R_{314}$ may each independently be selected from hydrogen, deuterium, —F, —Cl, —Br, —I, a hydroxyl group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, and $Q_{31}$ to $Q_{33}$ and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group.

NPD or NPB (see NPB structure below) has an absolute value of a HOMO energy level that is not greater than about 5.5 eV, in contrast to the hole transport material in the p-type charge generation layer 155".

In an embodiment, in Formula 301-2, $A_{301}$ to $A_{304}$ may each independently be a benzene group, and $X_{301}$ may be N-$[(L_{304})_{xb4}-R_{304}]$.

In an embodiment, the hole transport material may be selected from Compounds 1 to 10:

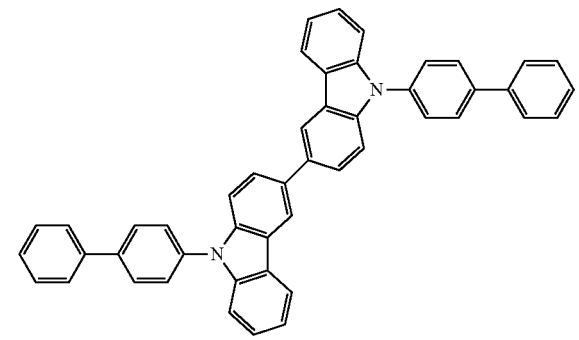

1

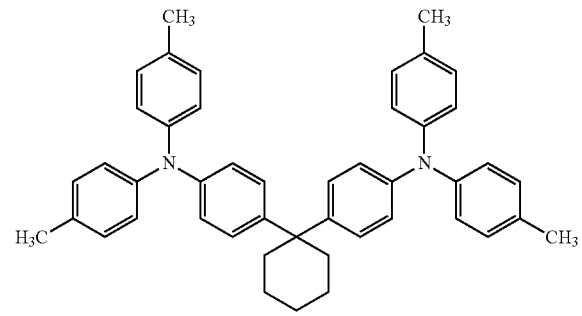

2

3
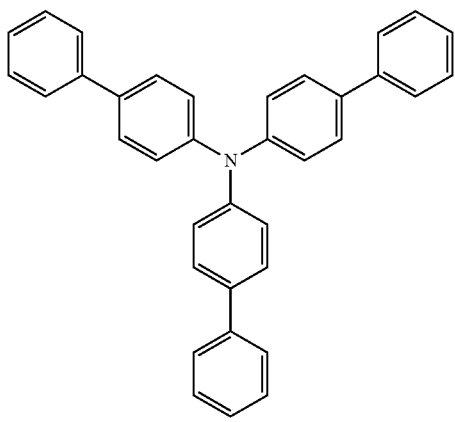
4
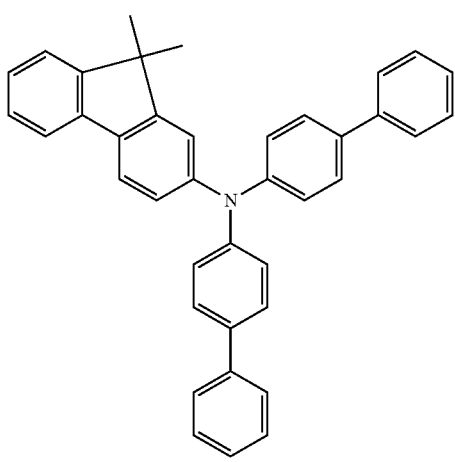
5
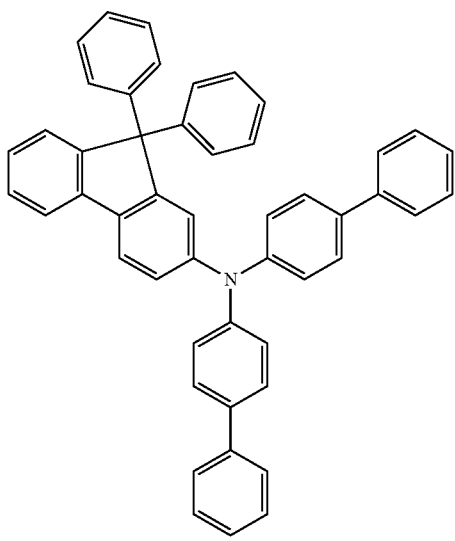
6
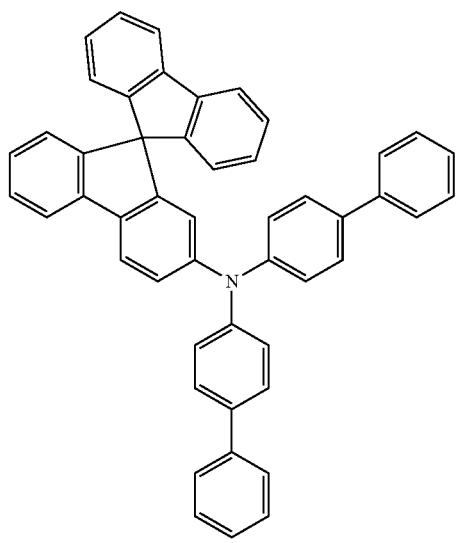
7
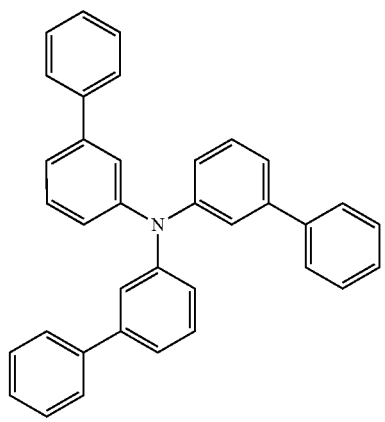
8

-continued

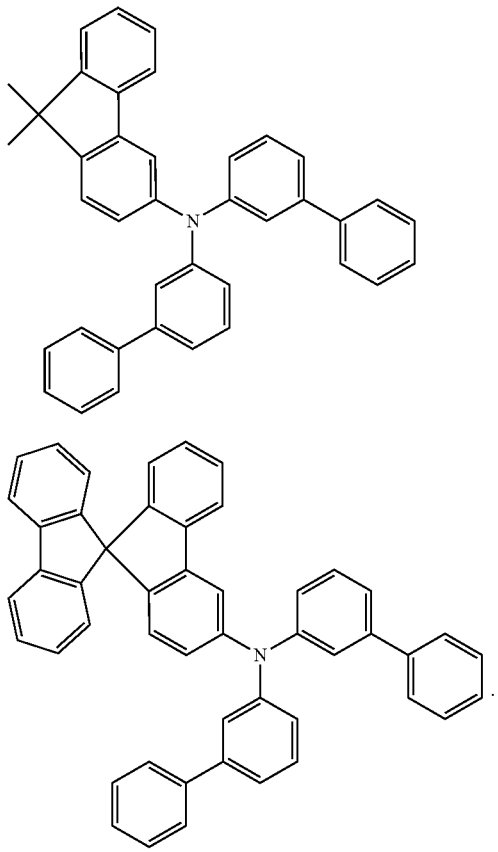

In an embodiment, at least one selected from m−1 p-type charge generation layer(s) 155″ may consist of the hole transport material.

In an embodiment, a thickness of each of the n-type charge generation layer 155′ and the p-type charge generation layer 155″ may be of about 20 Å to about 200 Å. For example, a thickness of each of the n-type charge generation layer 155′ and the p-type charge generation layer 155″ may be about 20 Å to about 100 Å.

When the thickness of each of the n-type charge generation layer 155′ and the p-type charge generation layer 155″ is within the ranges above, high-quality light emission characteristics may be implemented without a substantial increase in driving voltage.

In an embodiment, the organic light-emitting device 10 may further include at least one first electron transport layer disposed between at least one selected from m−1 n-type charge generation layer(s) 155′ and the light-emitting unit 153 adjacent to the at least one selected from m−1 n-type charge generation layer(s) 155′. The first electron transport layer may include, for example, an electron transport material and a metal-containing material, and the metal-containing material may include a metal, a metal oxide, a metal halide, or a combination thereof. The first electron transport layer may facilitate electron transport between the n-type charge generation layer 155′ and the light-emitting unit 153, thereby improving efficiency of the organic light-emitting device 10.

In an embodiment, in the first electron transport layer, an amount of the electron transport material may be greater than that of the metal-containing material. In an embodiment, in the first electron transport layer, an amount of the metal-containing material may be of about 0.1% to about 5% with respect to an amount of the electron transport material.

In an embodiment, the electron transport material may be an organic compound including at least one π electron-depleted nitrogen-containing ring. The term "π electron-depleted nitrogen-containing ring electron" will be described below in connection with an electron transport region.

The electron transport material may be an organic compound including, for example, an imidazole ring, a pyrazole ring, a thiazole ring, an isothiazole ring, an oxazole ring, an isoxazole ring, a pyridine ring, a pyrazine ring, a pyrimidine ring, a pyridazine ring, an indazole ring, a purine ring, a quinoline ring, an isoquinoline ring, a benzoquinoline ring, a phthalazine ring, a naphthyridine ring, a quinoxaline ring, a quinazoline ring, a cinnoline ring, a phenanthridine ring, an acridine ring, a phenanthroline ring, a phenazine ring, a benzimidazole ring, an isobenzothiazole ring, a benzoxazole ring, an isobenzoxazole ring, a triazole ring, a tetrazole ring, an oxadiazole ring, a triazine ring, a thiadiazol ring, an imidazopyridine ring, an imidazopyrimidine ring, an azacarbazole ring, etc. In an embodiment, the electron transport material may be an organic compound including at least one selected from a triazole ring, an oxadiazole ring, a benzimidazole ring, a phenanthroline ring, an imidazole ring, a pyridine ring, a pyrazine ring, a pyrimidine ring, a pyridazine ring, and a triazine ring.

In an embodiment, the electron transport material may be represented by Formula 1:

$$[Ar_1]_{c1}\text{-}[(L_1)_{a1}\text{-}R_1]_{b1} \qquad <\text{Formula 1}>$$

In Formula 1, $Ar_1$ may be a substituted or unsubstituted $C_5\text{-}C_{60}$ carbocyclic group or a substituted or unsubstituted $C_1\text{-}C_{60}$ heterocyclic group, c1 may be 1, 2, or 3, wherein, when c1 is two or more, two or more $Ar_1(s)$ may be identical to or different form each other, and may be linked to each other via a single bond, $L_1$ may be selected from a substituted or unsubstituted $C_3\text{-}C_{10}$ cycloalkylene group, a substituted or unsubstituted $C_1\text{-}C_{10}$ heterocycloalkylene group, a substituted or unsubstituted $C_3\text{-}C_{10}$ cycloalkenylene group, a substituted or unsubstituted $C_1\text{-}C_{10}$ heterocycloalkenylene group, a substituted or unsubstituted $C_6\text{-}C_{60}$ arylene group, a substituted or unsubstituted $C_1\text{-}C_{60}$ heteroarylene group, a substituted or unsubstituted divalent non-aromatic condensed polycyclic group, and a substituted or unsubstituted divalent non-aromatic condensed heteropolycyclic group, a1 may be an integer of 0 to 5, wherein, when a1 is 0, *-$(L_1)_{a1}$-*' may be a single bond, and when a1 is two or more, two or more $L_1(s)$ may be identical to or different from each other, $R_1$ may be selected from a substituted or unsubstituted $C_3\text{-}C_{10}$ cycloalkyl group, a substituted or unsubstituted $C_1\text{-}C_{10}$ heterocycloalkyl group, a substituted or unsubstituted $C_3\text{-}C_{10}$ cycloalkenyl group, a substituted or unsubstituted $C_1\text{-}C_{10}$ heterocycloalkenyl group, a substituted or unsubstituted $C_6\text{-}C_{60}$ aryl group, a substituted or unsubstituted $C_6\text{-}C_{60}$ aryloxy group, a substituted or unsubstituted $C_6\text{-}C_{60}$ arylthio group, a substituted or unsubstituted $C_1\text{-}C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —C(=O)($Q_1$), —S(=O)$_2$($Q_1$), and —P(=O)($Q_1$)($Q_2$), wherein $Q_1$ to $Q_3$ may each independently be a $C_1\text{-}C_{10}$ alkyl group, a $C_1\text{-}C_{10}$ alkoxy group, a phenyl group, a biphenyl group, a terphenyl group, or a naphthyl group, and b1 may be an integer of 1 to 5, wherein, when b1 is two or more, two or more $(L_1)_{a1}$-$R_1$(s) may be identical to or different from each other.

In an embodiment, in Formula 1, $Ar_1$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, an azacarbazole group, a pyridoquinazoline group, and a benzoimidazoquinazoline group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, an azacarbazole group, a pyridoquinazoline group, and a benzoimidazoquinazoline group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), $L_1$ may be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, and $R_1$ may be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, and a pyridonaphthyridinyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, and a pyridonaphthyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S($=$O)$_2$($Q_1$) and —P($=$O)($Q_1$)($Q_2$), wherein $Q_1$, $Q_2$, and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

The metal-containing material included in the first electron transport layer may be as defined herein.

In an embodiment, the metal-containing material included in at least one selected from m−1 n-type charge generation layer(s) may be the same as the metal-containing material included in the first electron transport layer.

In an embodiment, the metal-containing material included in at least one selected from m−1 n-type charge generation layer(s) may be different from the metal-containing material included in the first electron transport layer.

The organic light-emitting device 10 according to an embodiment may further include a second electron transport layer between the first electron transport layer and the light-emitting unit adjacent to the first electron transport layer. The second electron transport layer may include an electron transport material.

In an embodiment, the electron transport material included in the second electron transport layer may include at least one π electron-depleted nitrogen-containing ring. For example, the electron transport material included in the second electron transport layer may include at least one selected from a triazole ring, an oxadiazole ring, a benzimidazole ring, a phenanthroline ring, an imidazole ring, a pyridine ring, a pyrazine ring, a pyrimidine ring, a pyridazine ring, and a triazine ring.

In an embodiment, the electron transport material included in the first electron transport layer may be the same as the electron transport material included in the second electron transport layer.

In an embodiment, the hole transport region may further include a buffer layer. The buffer layer will be further described in detail below.

Figure 2:
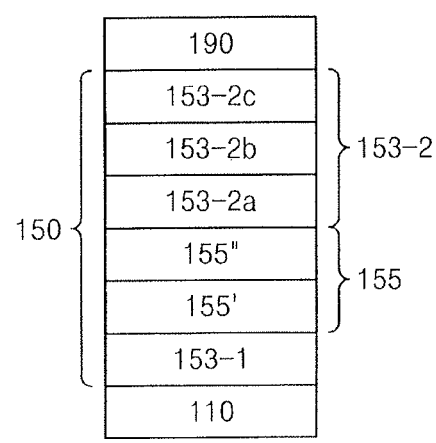
Figure 3:
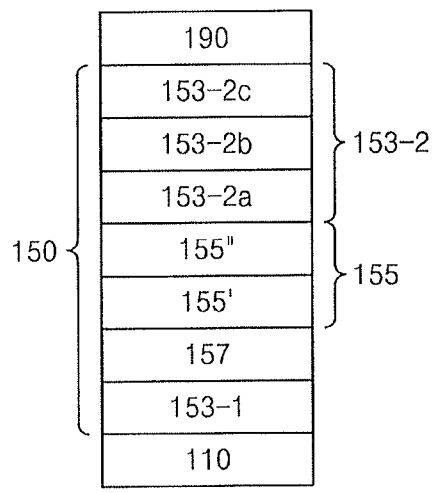
Figure 4:
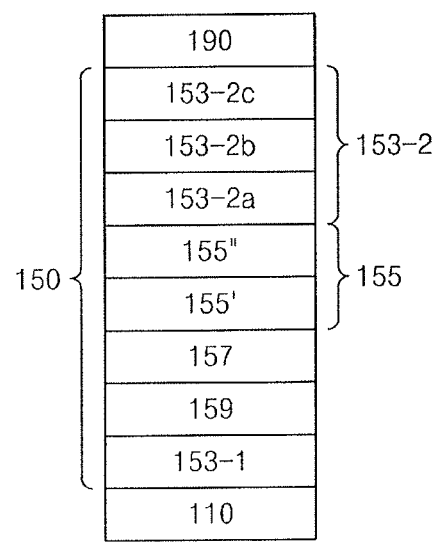
Figure 5:
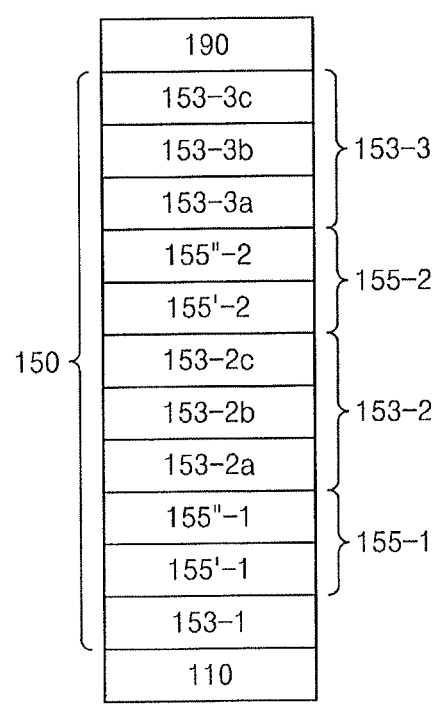

In the organic light-emitting device 10 according to an embodiment, m may be, for example, 2 or 3. FIGS. 2 to 4 each show an organic light-emitting device in which m is 2, and FIG. 5 shows an organic light-emitting device in which m is 3.

In an embodiment of the organic light-emitting device in which m is 2, m light-emitting units may include a first light-emitting unit and a second light-emitting unit, m−1 charge generation layer(s) may include charge generation layer, the charge generation layer may be disposed between the first light-emitting unit and the second light-emitting unit, the first light-emitting unit may be disposed between the first electrode and the charge generation layer, the second light-emitting unit may be disposed between the charge generation layer and the second electrode, the charge generation layer may include the n-type charge generation layer and the p-type charge generation layer, wherein the n-type charge generation layer may be disposed between the first light-emitting unit and the second light-emitting unit, and the p-type charge generation layer may be disposed between the n-type charge generation layer and the second light-emitting unit, the n-type charge generation layer may consist of the metal-containing material, the p-type charge generation layer may include the hole transport material, the second light-emitting unit may include the hole transport region, the hole transport region may include the hole transport layer, the p-type charge generation layer may be adjacent to the hole transport layer in the second light-emitting unit, an absolute value of a HOMO energy level of the hole transport material of the p-type charge generation layer may be greater than about 5.5 eV, and an absolute value of a LUMO energy level of the hole transport material of the p-type charge generation layer may be less than that of a LUMO energy level of the hole transport layer of the second light-emitting unit.

In an embodiment, an absolute value of a LUMO energy level of the hole transport material of the p-type charge generation layer may be the same as or greater than that of a LUMO energy level of the hole transport layer of the second light-emitting unit.

In an embodiment, the organic light-emitting device may further include a first electron transport layer disposed between the n-type charge generation layer and the first light-emitting unit. The first electron transport layer may include the electron transport material and the metal-containing material, and the metal-containing material may be a metal, a metal oxide, a metal halide, or a combination thereof.

In an embodiment, the organic light-emitting device may further include a second electron transport layer disposed between the first electron transport layer and the first light-emitting unit. The second electron transport layer may include the electron transport material. The electron transport material and the metal-containing material may each independently be as defined herein.

In an embodiment of the organic light-emitting device in which m is 3, m light-emitting units may include a first light-emitting unit, a second light-emitting unit, and a third light-emitting unit, m−1 charge generation layer(s) may include a first charge generation layer and a second charge generation layer, the first charge generation layer may be disposed between the first light-emitting unit and the second light-emitting unit, the second charge generation layer may be disposed between the second light-emitting unit and the third light-emitting unit, the first light-emitting unit may be disposed between the first electrode and the first charge generation layer, the second light-emitting unit may be disposed between the first charge generation layer and the second charge generation layer, the third light-emitting unit may be disposed between the second charge generation layer and the second electrode, the first charge generation layer may include a first n-type charge generation layer and a first p-type charge generation layer, wherein the first n-type charge generation layer may be disposed between the first light-emitting unit and the second light-emitting unit, and the first p-type charge generation layer may be disposed between the first n-type charge generation layer and the second light-emitting unit, the second charge generation layer may include a second n-type charge generation layer and a second p-type charge generation layer, wherein the second n-type charge generation layer may be disposed between the second light-emitting unit and the third light-emitting unit, and the second p-type charge generation layer may be disposed between the second n-type charge generation layer and the third light-emitting unit, the first n-type charge generation layer or the second n-type charge generation layer may consist of the metal-containing material, the first p-type charge generation layer or the second p-type charge generation layer may include the hole transport material, the second light-emitting unit or the third light-emitting unit may include the hole transport region, the hole transport region may include the hole transport layer, the first p-type charge generation layer may be adjacent to the hole transport layer in the second light-emitting unit, or the second p-type charge generation layer may be adjacent to the hole transport layer in the third light-emitting unit, an absolute value of a HOMO energy level of the hole transport material of the first p-type charge generation layer or the second p-type charge generation layer may be greater than about 5.5 eV, and an absolute value of a LUMO energy level of the hole transport material of the first p-type charge generation layer may be less than that of a LUMO energy level of the hole transport layer of the second light-emitting unit, or an absolute value of a LUMO energy level of the hole transport material of the second p-type charge generation layer may be less than that of a LUMO energy level of the hole transport layer of the third light-emitting unit.

When the n-type charge generation layer consists of the metal-containing material having a work function of about 2.0 eV to about 4.5 eV, the electron transport between the electron-rich metal-containing material and the electron transport layer of the electron transport region of the light-emitting unit adjacent to the n-type charge generation layer may be smoothly performed. Furthermore, by the electron transport, the metal-containing material adjacent to an interface between the n-type charge generation layer and the p-type charge generation layer may have a positive charge so that polarity inside the p-type charge generation layer may be separated.

As a result, holes may be transported from the p-type charge generation layer to the hole transport layer in the light-emitting unit adjacent to the p-type charge generation layer without introducing another p-type dopant, and in this regard, current leakage caused by a general p-type dopant may be reduced or eliminated.

In addition, when an absolute value of a HOMO energy level of the hole transport material of the p-type charge generation layer is the same as or greater than that of a HOMO energy level of the hole transport layer adjacent to the p-type charge generation layer, due to the difference in the HOMO energy levels therebetween, the hole transport from the p-type charge generation layer to the hole transport layer adjacent to the p-type charge generation layer may become more advantageous, which may improve efficiency of the light-emitting unit and more effectively reducing driving voltage.

In addition, when the organic light-emitting device includes the first electron transport layer including the metal-containing material and the electron transport material, electron transport between adjacent light-emitting units may be further facilitated, which may improve the efficiency of the organic light-emitting device.

In addition, when the organic light-emitting device further includes the second electron transport layer including the electron transport material, a transport speed of electrons to the adjacent light-emitting units may be appropriately controlled, which may improve the lifespan of the organic light-emitting device.

[Descriptions of FIGS. 2 to 5]

FIG. 2 is a schematic view of an organic light-emitting device 11 according to an embodiment in which m is 2. In FIG. 2, the organic light-emitting device 11 has a stacked structure including the first electrode 110, a first light-emitting unit 153-1, the charge generation layer 155 including the n-type charge generation layer 155' and the p-type charge generation layer 155", the second light-emitting unit 153-2 including a hole transport layer 153-2a, an emission layer 153-2b, and an electron transport layer 153-2c, and the second electrode 190.

FIG. 3 is a schematic view of an organic light-emitting device 12 according to an embodiment in which m is 2. In FIG. 3, the organic light-emitting device 12 has a stacked structure including the first electrode 110, the first light-emitting unit 153-1, the first electron transport layer 157, the charge generation layer 155 including the n-type charge generation layer 155' and the p-type charge generation layer 155", the second light-emitting unit 153-2 including the hole transport layer 153-2a, the emission layer 153-2b, and the electron transport layer 153-2c, and the second electrode 190.

FIG. 4 is a schematic view of an organic light-emitting device 13 according to an embodiment in which m is 2. In FIG. 4, the organic light-emitting device 13 has a stacked structure including the first electrode 110, the first light-emitting unit 153-1, a second electron transport layer 159, the first electron transport layer 157, the charge generation layer 155 including the n-type charge generation layer 155' and the p-type charge generation layer 155", the second light-emitting unit 153-2 including the hole transport layer 153-2a, the emission layer 153-2b, and the electron transport layer 153-2c, and the second electrode 190.

FIG. 5 is a schematic view of an organic light-emitting device 14 according to an embodiment in which m is 3. In FIG. 5, the organic light-emitting device 14 has a stacked structure including the first electrode 110, the first light-emitting unit 153-1, a first charge generation layer 155-1 including a first n-type charge generation layer 155'-1 and a first p-type charge generation layer 155"-1, the second light-emitting unit 153-2 including the hole transport layer 153-2a, the emission layer 153-2b, and the electron transport layer 153-2c, a second charge generation layer 155-2 including a second n-type charge generation layer 155'-2 and a second p-type charge generation layer 155"-2, a third light-emitting unit 153-3 including a hole transport layer 153-3a, an emission layer 153-3b, and an electron transport layer 153-3c, and the second electrode 190.

Hereinafter, the structures of the organic light-emitting devices 10, 11, 12, 13, and 14 according to embodiments and methods of manufacturing the organic light-emitting devices 10, 11, 12, 13, and 14 according to embodiments will be described in connection with FIGS. 1 to 5.

[First Electrode 110]

In FIGS. 1 to 5, a substrate may be additionally disposed under the first electrode 110 or above the second electrode 190. The substrate may be, for example, a glass substrate or a transparent plastic substrate, which may afford excellent mechanical strength, thermal stability, transparency, surface smoothness, ease of handling, and water resistance.

The first electrode 110 may be formed by, for example, depositing or sputtering a material for forming the first electrode 110 on the substrate. When the first electrode 110 is an anode, the material for forming the first electrode 110 may be selected from materials with a high work function to facilitate hole injection.

The first electrode 110 may be, for example, a reflective electrode, a semi-transmissive electrode, or a transmissive electrode. When the first electrode 110 is a reflective electrode, examples of the material for forming the first electrode 110 include indium tin oxide (ITO), indium zinc oxide (IZO), tin oxide ($SnO_2$), and zinc oxide (ZnO). When the first electrode 110 is a semi-transmissive electrode or a reflective electrode, the material for forming the first electrode 110 may be selected from, for example, magnesium (Mg), silver (Ag), aluminum (Al), aluminum-lithium (Al—Li), calcium (Ca), magnesium-indium (Mg—In), magnesium-silver (Mg—Ag), and a combination thereof.

The first electrode 110 may have a single-layered structure, or a multi-layered structure including two or more layers. For example, the first electrode 110 may have a three-layered structure of ITO/Ag/ITO.

[Organic Layer 150]

The organic layer 150 may be disposed on the first electrode 110. The organic layer 150 may include at least one of the light-emitting units 153, 153-1, 153-2, and 153-3.

The organic layer 150 may further include the hole transport region disposed between the first electrode 110 and the at least one of the light-emitting units 153, 153-1, 153-2, and 153-3, and the electron transport region disposed between the at least one of the light-emitting units 153, 153-1, 153-2, and 153-3 and the second electrode 190.

[Hole Transport Region in Organic Layer 150]

The hole transport region may have, for example, i) a single-layered structure including a single material, ii) a single-layered structure including a plurality of different materials, or iii) a multi-layered structure having a plurality of layers including a plurality of different materials.

The hole transport region may include, for example, at least one layer selected from a hole injection layer, the hole transport layer 153-2a or 153-3a, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in their stated orders.

The hole transport region may further include at least one selected from, for example, m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201, and a compound represented by Formula 202:

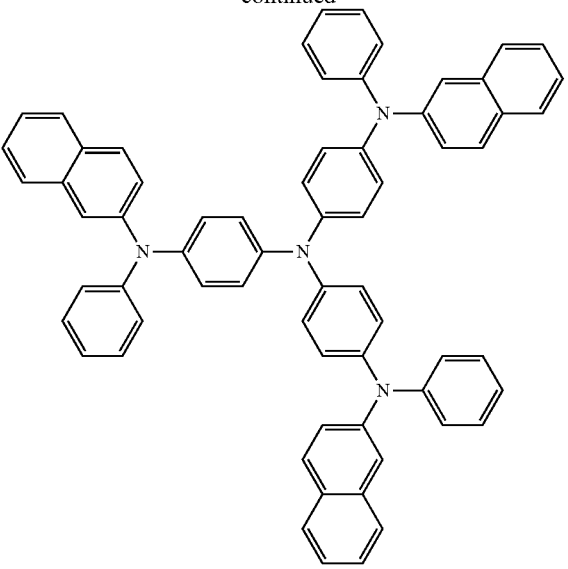

2-TNATA

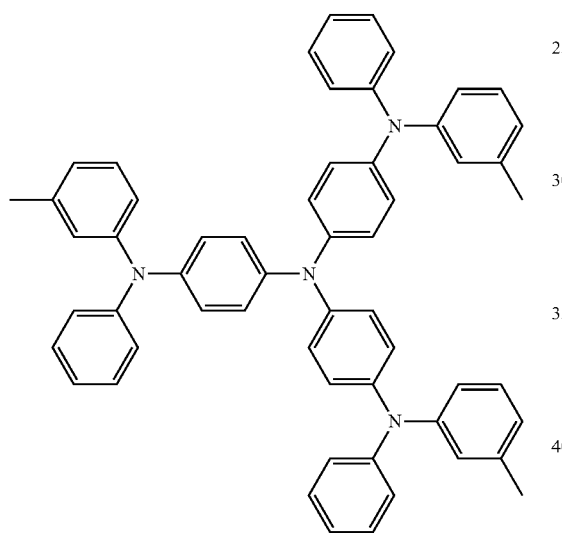

m-MTDATA

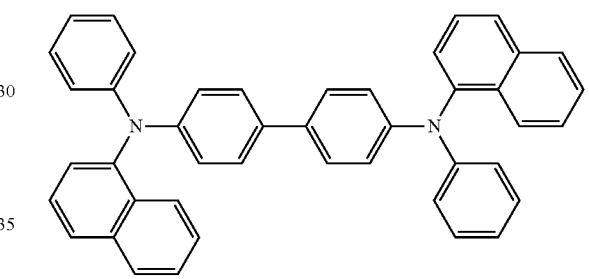

NPB

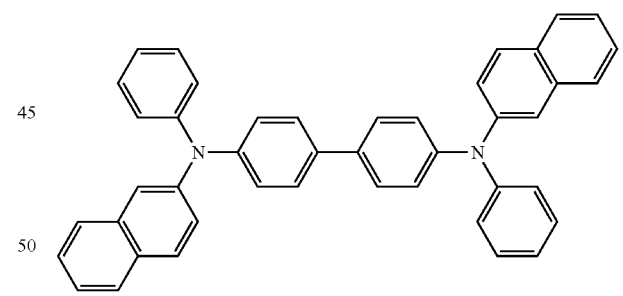

β-NPB

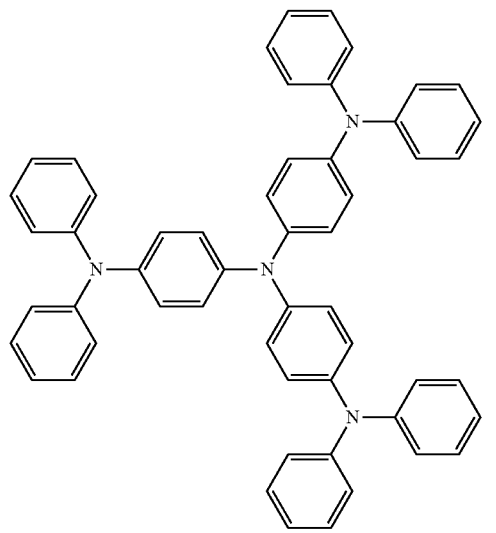

TDATA

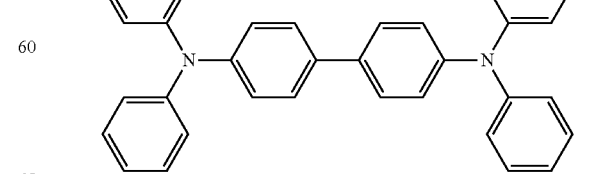

TPD

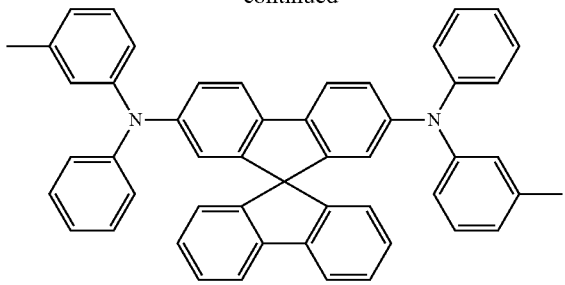

Spiro-TPD

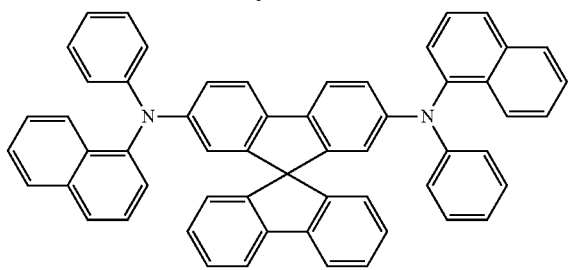

Spiro-NPB

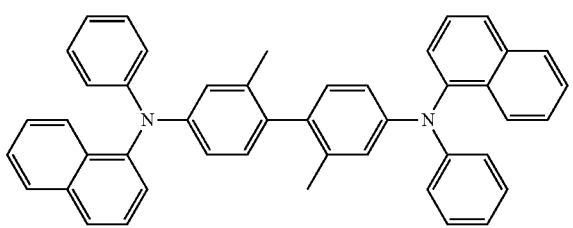

methylated NPB

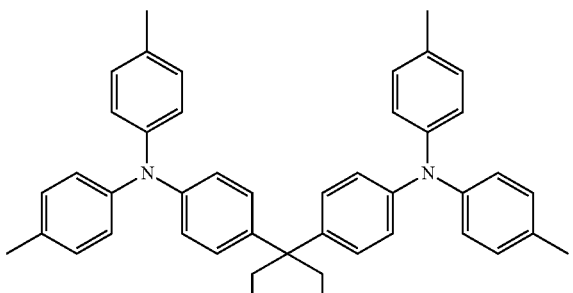

TAPC

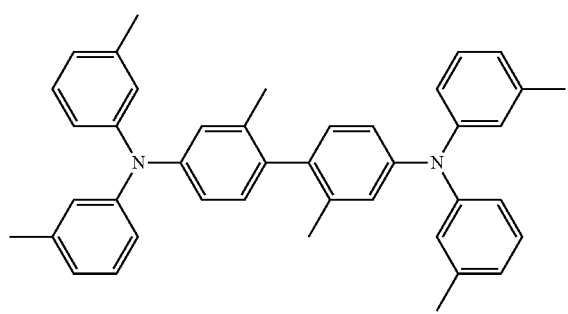

HMTPD

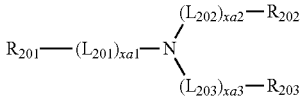

<Formula 201>

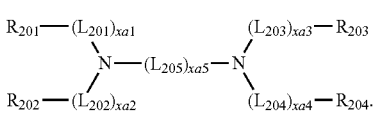

<Formula 202>

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked to each other via a single bond, a dimethyl-methylene group, or a diphenyl-methylene group, and $R_{203}$ and $R_{204}$ may optionally be linked to each other via a single bond, a dimethyl-methylene group, or a diphenyl-methylene group.

In an embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an embodiment, xa1 to xa4 may each independently be 0, 1, or 2.

In an embodiment, xa5 may be 1, 2, 3, or 4.

In an embodiment, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be as defined herein.

In an embodiment, in Formula 201, at least one selected from $R_{201}$ to $R_{203}$ may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

In an embodiment, in Formula 202, i) $R_{201}$ and $R_{202}$ may be linked to each other via a single bond, and/or ii) $R_{203}$ and $R_{204}$ may be linked to each other via a single bond.

In an embodiment, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

In an embodiment, the compound represented by Formula 201 may be represented by Formula 201A:

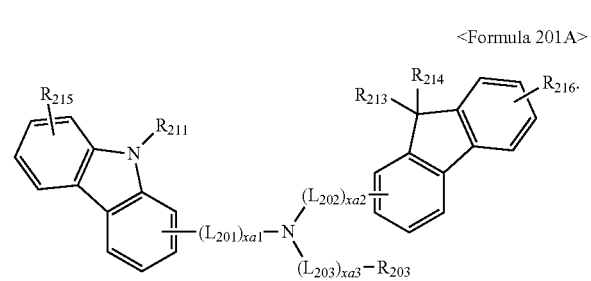
<Formula 201A>

In an embodiment, the compound represented by Formula 201 may be represented by Formula 201A(1):

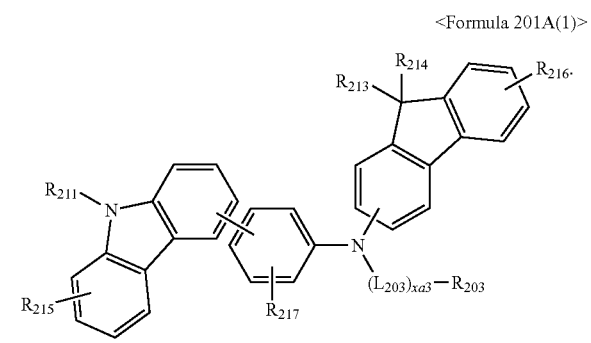
<Formula 201A(1)>

In an embodiment, the compound represented by Formula 201 may be represented by Formula 201A-1:

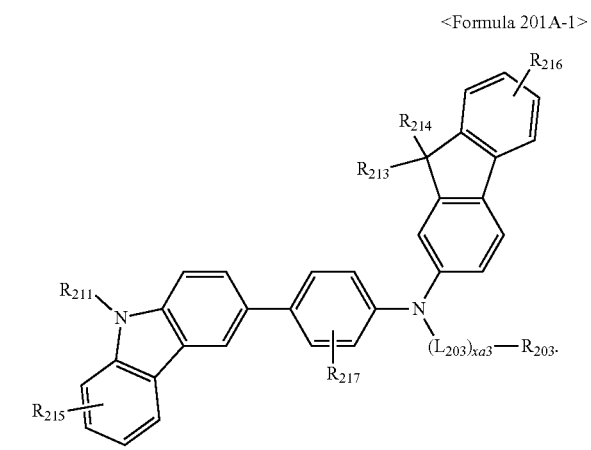
<Formula 201A-1>

In an embodiment, the compound represented by Formula 202 may be represented by Formula 202A:

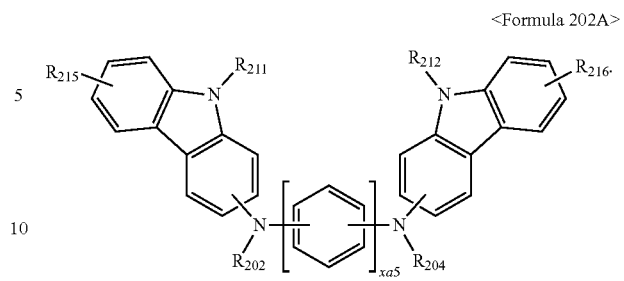
<Formula 202A>

In an embodiment, the compound represented by Formula 202 may be represented by Formula 202A-1:

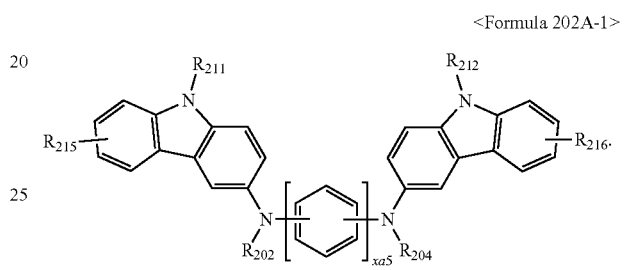
<Formula 202A-1>

In Formulae 201A, 201A(1), 201A-1, 202A, and 202A-1, $L_{201}$ to $L_{203}$, xa1 to xa3, xa5, and $R_{202}$ to $R_{204}$ may each independently be as defined herein, $R_{211}$ and $R_{212}$ may each independently be as defined herein in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In an embodiment, the hole transport region may include at least one compound selected from Compounds HT1 to HT39:

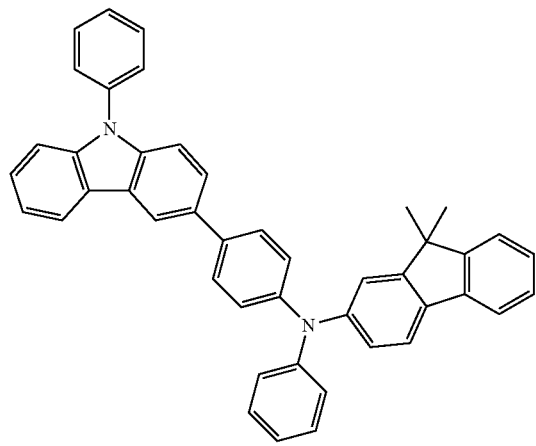
HT1
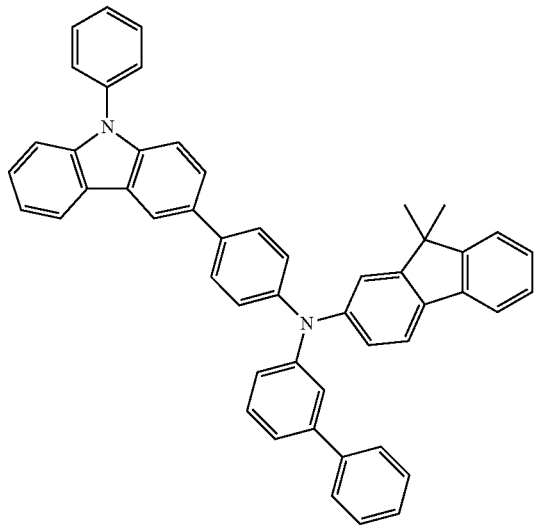
HT2
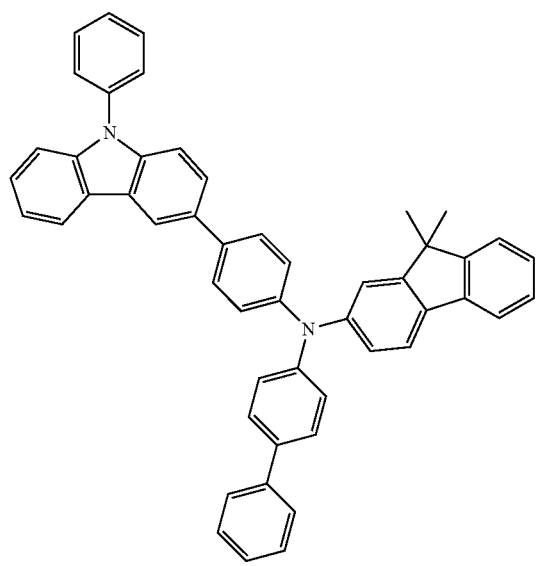
HT3
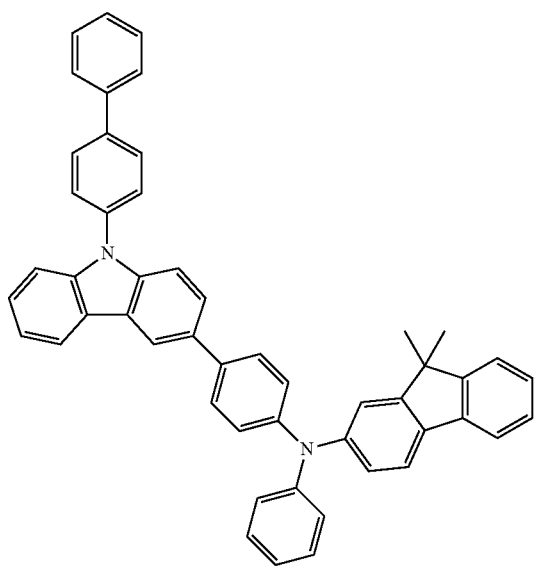
HT4

-continued
HT5
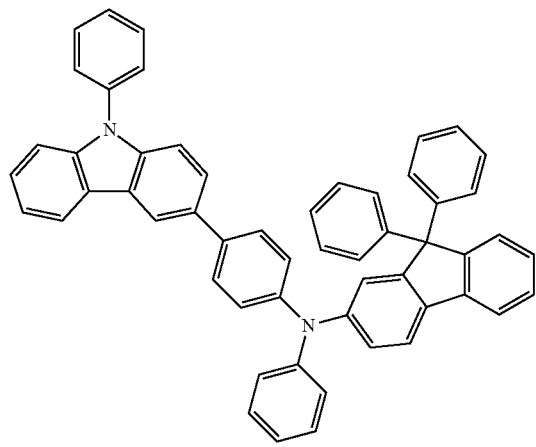
HT6
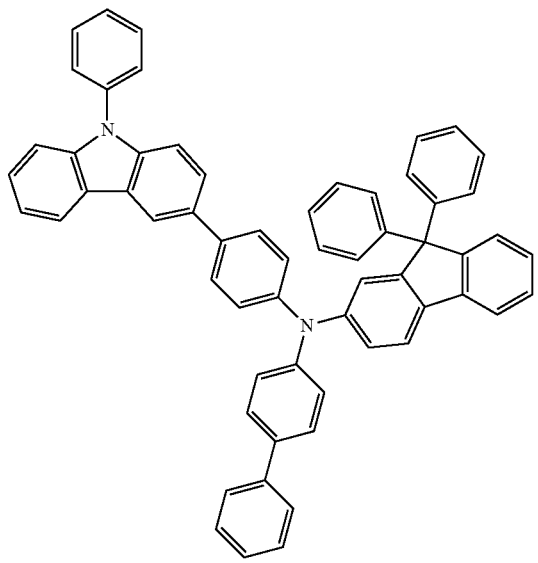
HT7
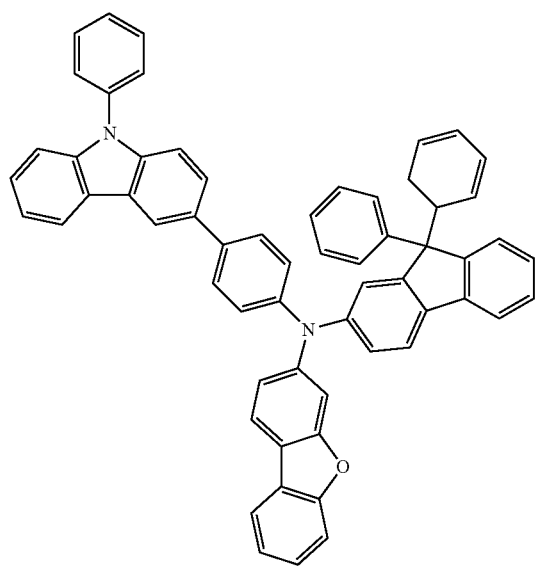
HT8
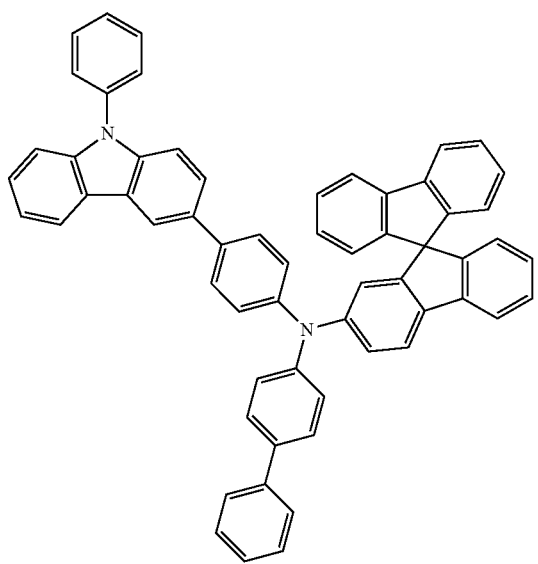

-continued
HT9
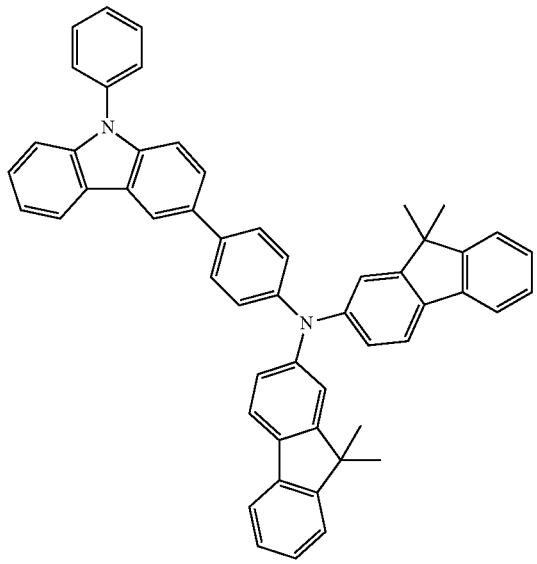
HT10
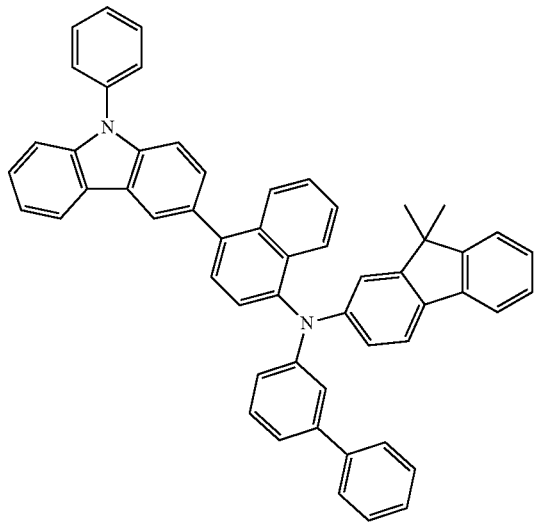
HT11
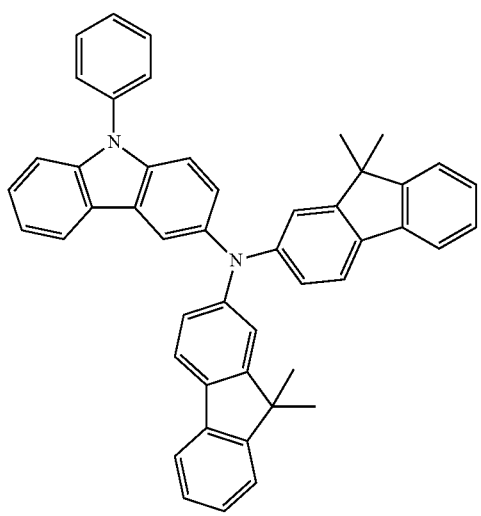
HT12
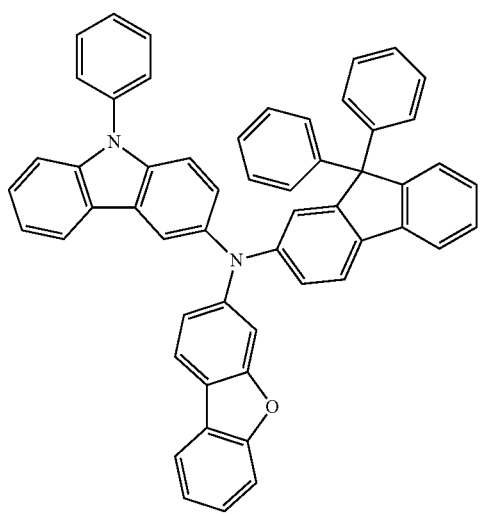
HT13
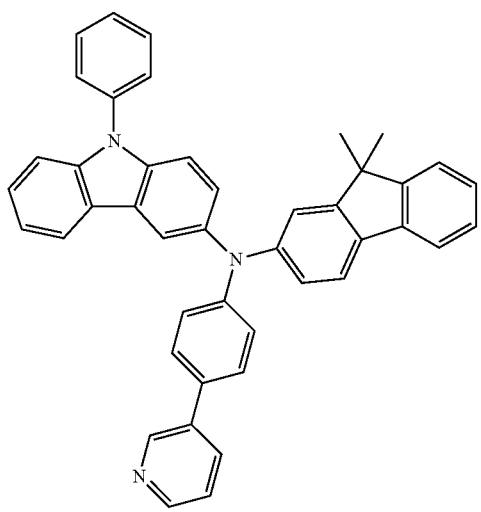
HT14
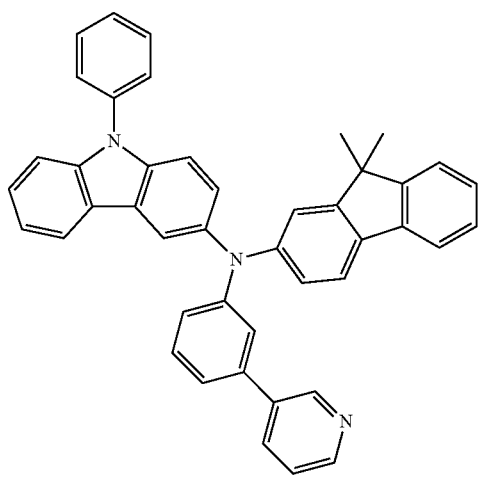

-continued
HT15
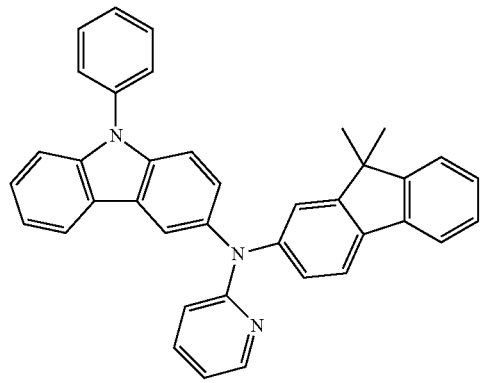
HT16
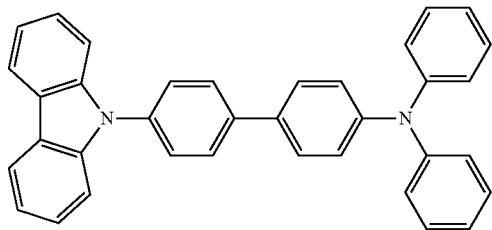
HT17
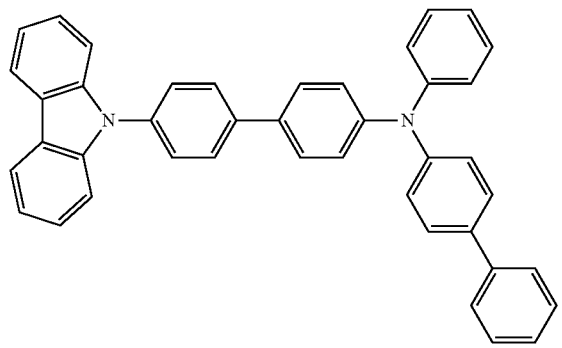
HT18
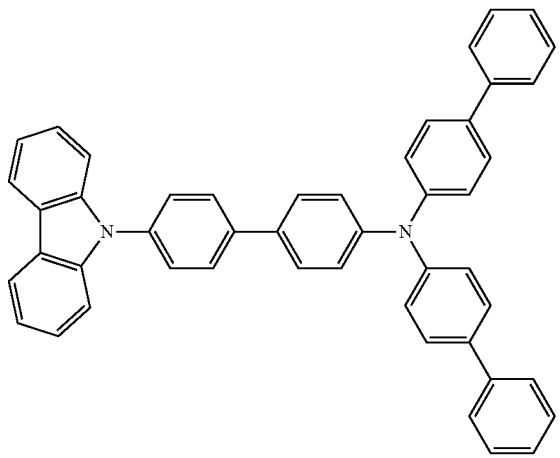
HT19
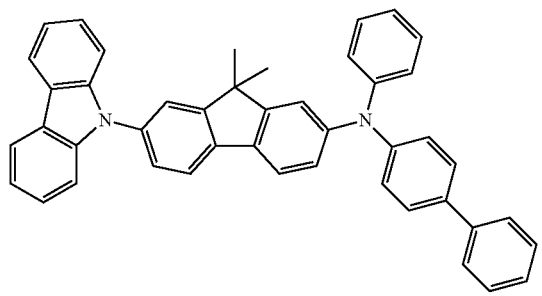
HT20
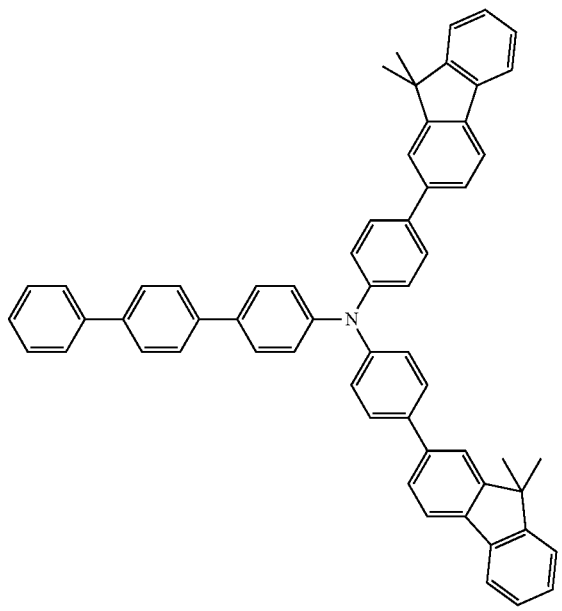

HT21
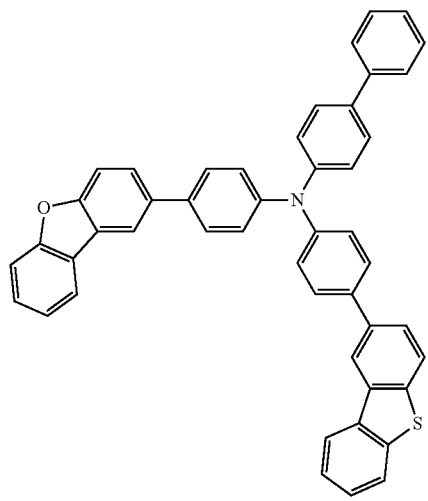
HT22
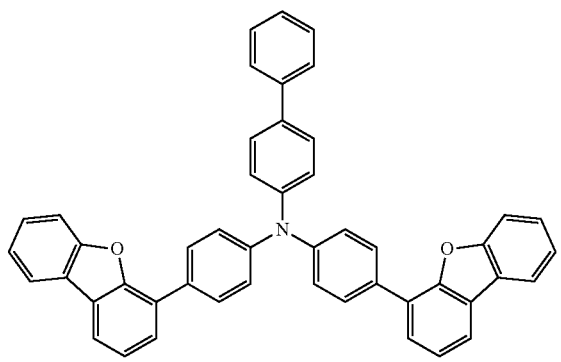
HT23
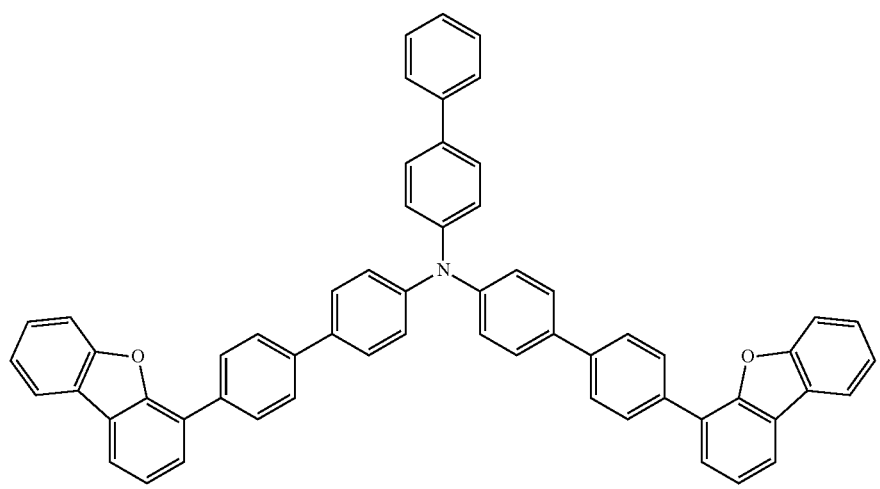
HT24
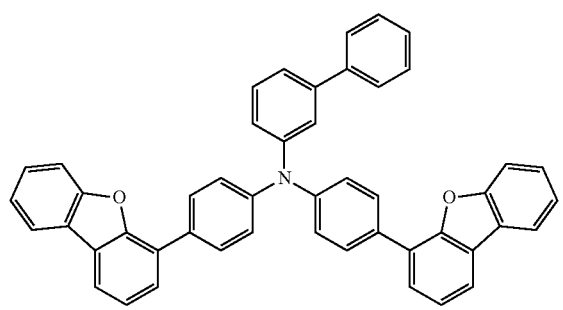
HT25
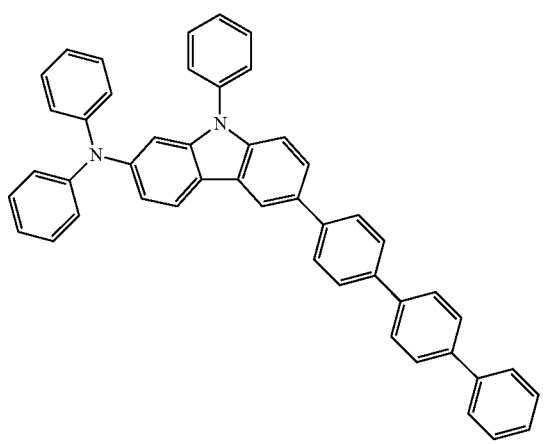

-continued
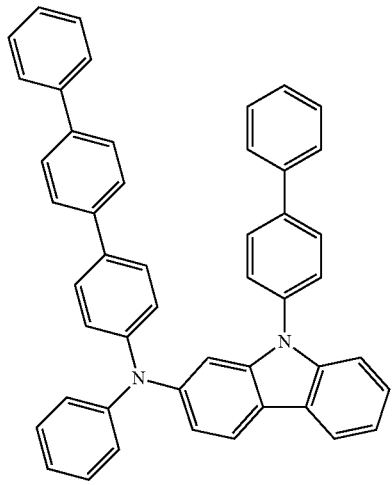
HT26
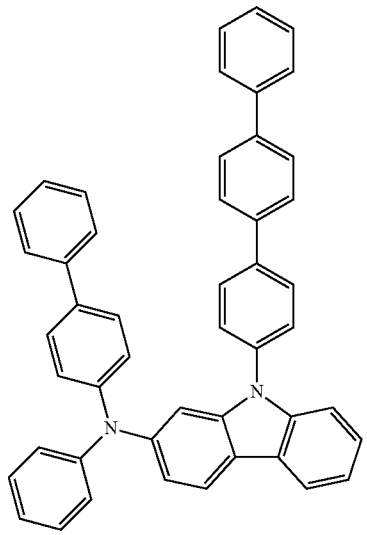
HT27
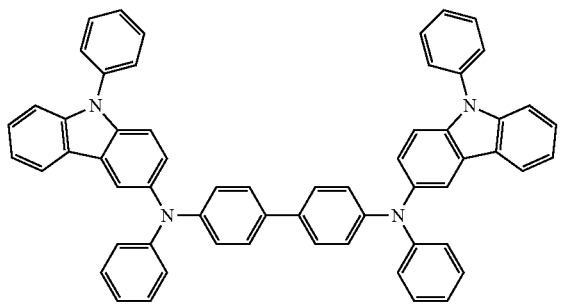
HT28
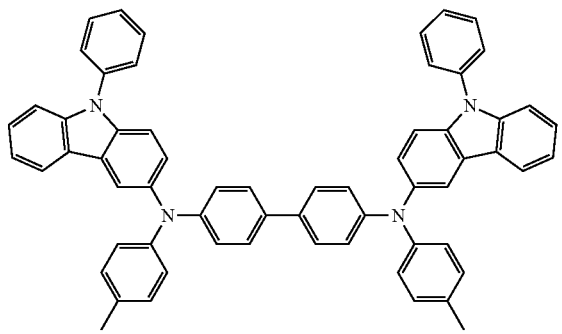
HT29
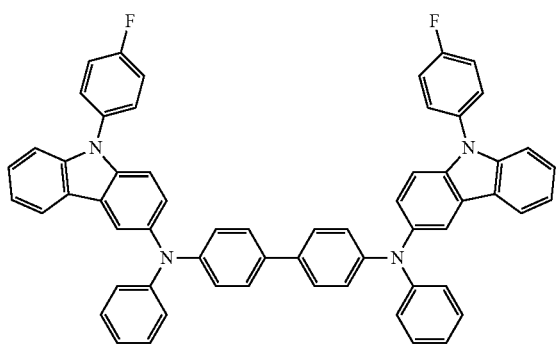
HT30
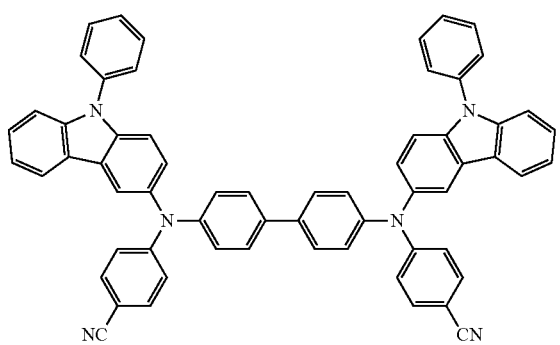
HT31
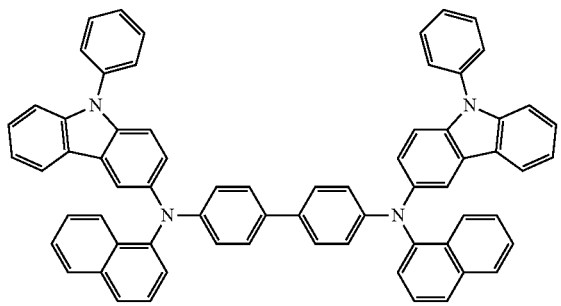
HT32
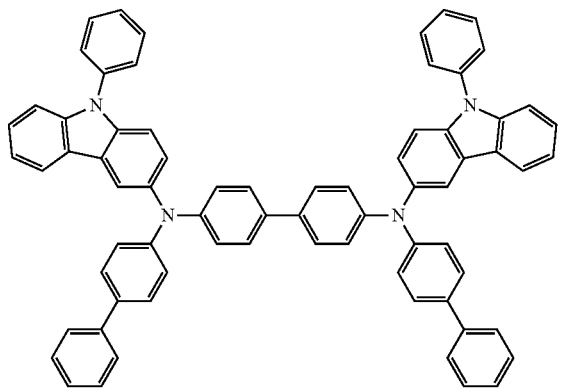
HT33

-continued

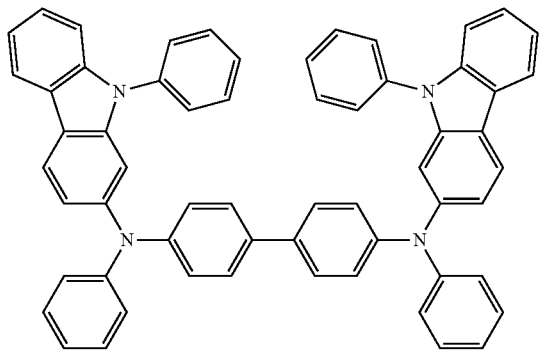
HT34

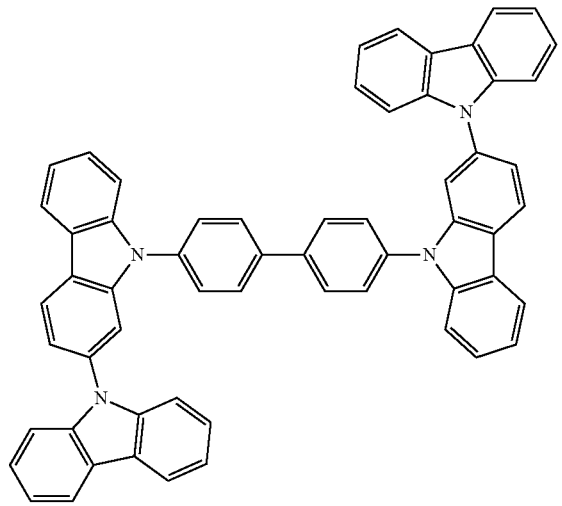
HT35

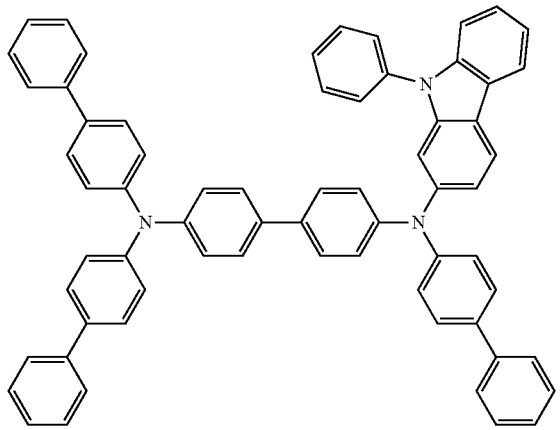
HT36

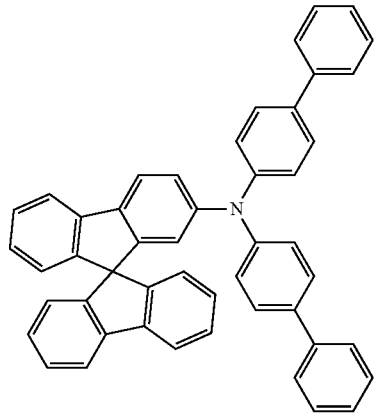
HT37

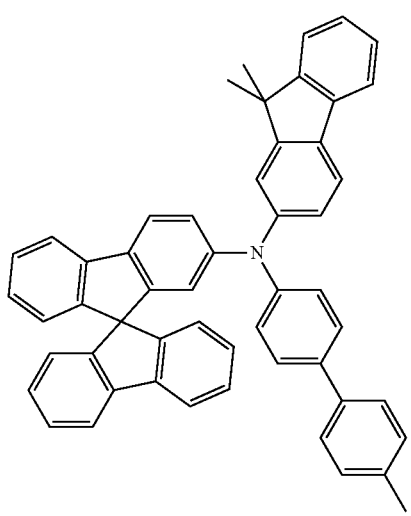
HT38

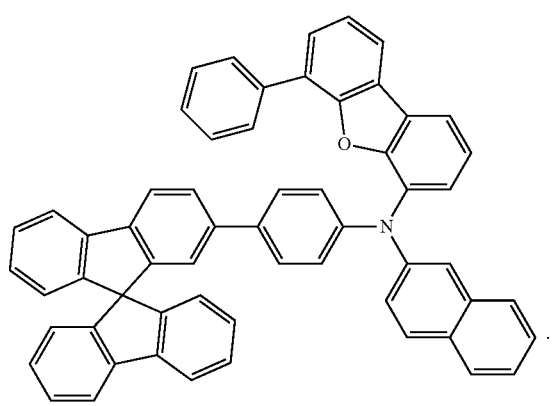
HT39

A thickness of the hole transport region may be in a range from about 50 Å to about 10,000 Å, for example, about 100 Å to about 1,000 Å. When the hole transport region includes at least one of a hole injection layer and a hole transport layer, a thickness of the hole injection layer may be in a range from about 100 Å to about 9,000 Å, for example, about 100 Å to about 1,000 Å, and a thickness of the hole transport layer may be in a range from about 50 Å to about 2,000 Å, for example, about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The emission auxiliary layer may compensate for an optical resonance distance according to a wavelength of light emitted from the emission layer, and thus, light emission efficiency of a formed organic light-emitting device may be improved. The electron blocking layer may block injection of electrons from the electron transport region. The emission auxiliary layer and the electron blocking layer may include the materials described above.

[P-Dopant]

The hole transport region may further include, in addition to the materials described above, a charge-generating material for the improvement of conductive properties.

The charge-generating material may be homogeneously or non-homogeneously dispersed in the hole transport region.

The charge-generating material may be, for example, a p-dopant.

In an embodiment, the p-dopant may have a LUMO energy level of about −3.5 eV or less.

The p-dopant may be one selected from, for example, a quinone derivative, a metal oxide, and a cyano group-containing compound.

For example, the p-dopant may include at least one selected from:

a quinone derivative, such as tetracyanoquinonedimethane (TCNQ) and 2,3,5,6-tetrafluoro-tetracyano-1,4-benzoquinonedimethane (F4-TCNQ);

a metal oxide, such as a tungsten oxide and a molybdenum oxide;

a cyano group-containing compound, such as 1,4,5,8,9,11-hexaazatriphenylene-hexacarbonitrile (HAT-CN); and a compound represented by Formula 221:

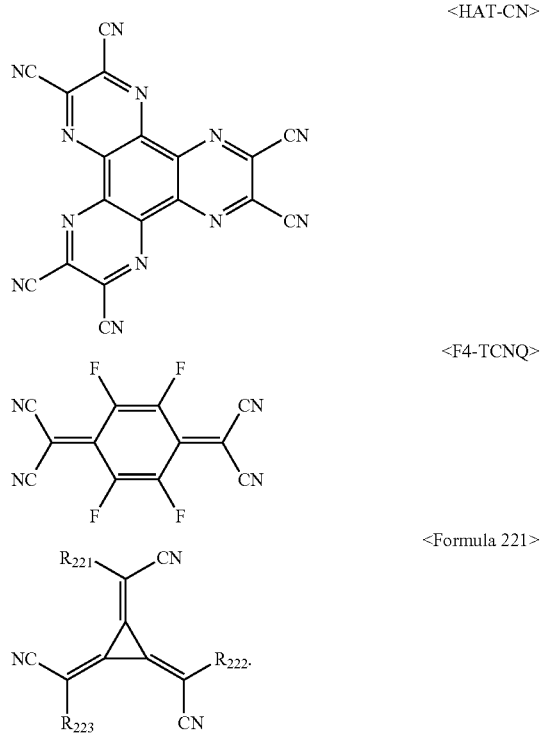

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have a substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layers 153, 153-1, 153-2, or 153-3 in Organic Layer 150]

In the organic light-emitting devices 10, 11, 12, 13, or 14, the light-emitting units 153, 153-1, 153-2, or 153-3 may include the emission layers 153-2b or 153-3b, wherein the emission layers 153-2b or 153-3b may have a stacked structure in which at least two layers selected from a red emission layer, a green emission layer, a yellow emission layer, and a blue emission layer contact each other or are spaced apart from each other. In addition, the emission layers 153-2b or 153-3b may have a structure in which at least two materials selected from a red light-emitting material, a green light-emitting material, a yellow light-emitting material, and a blue light-emitting material are mixed with each other in a single layer.

An electron transporting (ET)-auxiliary layer may further be formed on the emission layers 153-2b or 153-3b, and/or a hole transporting (HT)-auxiliary layer may be formed under the emission layers 153-2b or 153-3b. The HT-auxiliary layer may refer to a layer that serves as the hole transport layer, the emission auxiliary layer, and/or the electron blocking layer described above, and the ET-auxiliary layer may refer to a layer that serves as a buffer layer, a hole blocking layer, an electron control layer, and/or an electron transport layer that will be described below. A material suitable for the HT-auxiliary layer and the ET-auxiliary layer may be a material suitable for the hole transport region described above and an electron transport region that will be described below.

The emission layers 153-2b or 153-3b may include a host and a dopant. The dopant may include, for example, at least one of a phosphorescent dopant and a fluorescent dopant.

An amount of the above dopant in the emission layers 153-2b or 153-3b may be, for example, in a range from about 0.01 parts to about 15 parts by weight based on 100 parts by weight of the host, but is not limited thereto.

A thickness of the emission layers 153-2b or 153-3b may be in a range from about 100 Å to about 1,000 Å, for example, about 200 Å to about 600 Å. When the thickness of the emission layers 153-2b or 153-3b is within any of these ranges, excellent light emission characteristics may be obtained without a substantial increase in driving voltage.

[Host in Emission Layers 153-2b or 153-3b]

The host may include a compound represented by Formula 301:

$[Ar_{301}]_{xb11}$-$[(L_{301})_{xb1}$-$R_{301}]_{xb21}$  <Formula 301>

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer of 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer of 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group.

In an embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 301, when xb11 is two or more, two or more $Ar_{301}$(s) may be linked to each other via a single bond.

In an embodiment, the compound represented by Formula 301 may be represented by Formula 301-1 or 301-2:

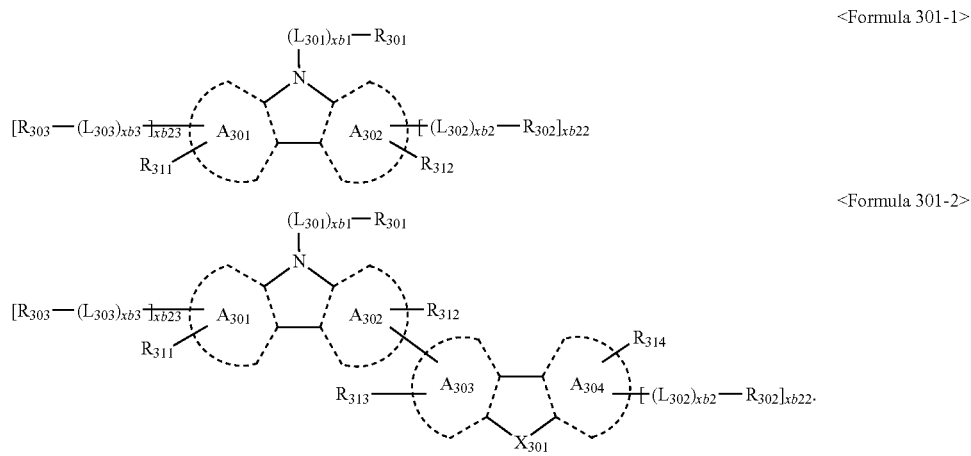

<Formula 301-1>

<Formula 301-2>

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be as defined herein, $L_{302}$ to $L_{304}$ may each independently be as defined herein in connection with $L_{301}$, xb2 to xb4 may each independently be as defined herein in connection with xb1, and $R_{302}$ to $R_{304}$ may each independently be as defined herein in connection with $R_{301}$.

In an embodiment, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be as defined herein.

In an embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be as defined herein.

In an embodiment, the host may include an alkaline earth metal complex. For example, the host may be selected from a beryllium (Be) complex (for example, Compound H55), a Mg complex, and a Zn complex.

In an embodiment, the host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55:

H1

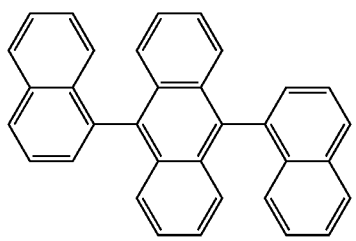

H2

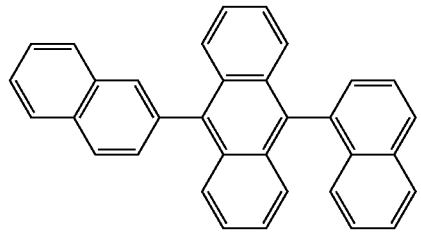

H3

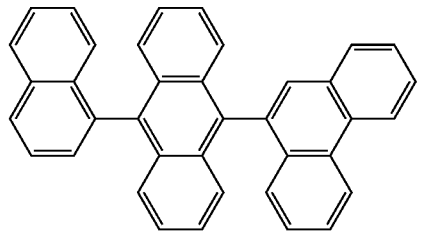

H4

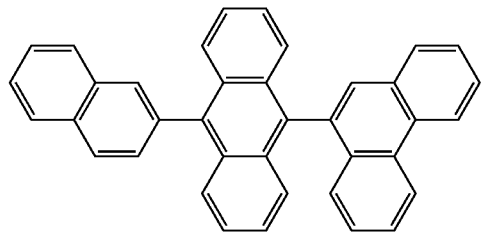

H5

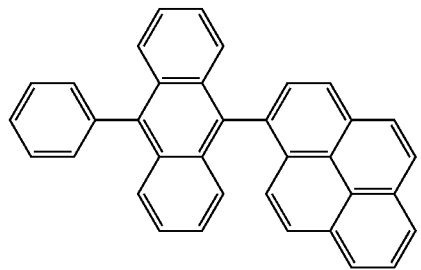

H6

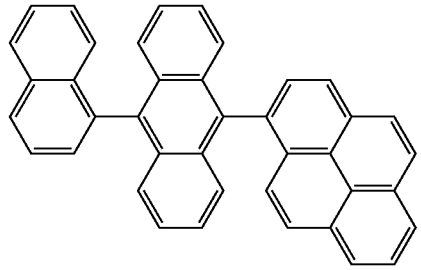

H7

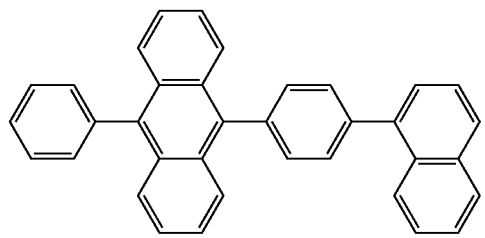

-continued
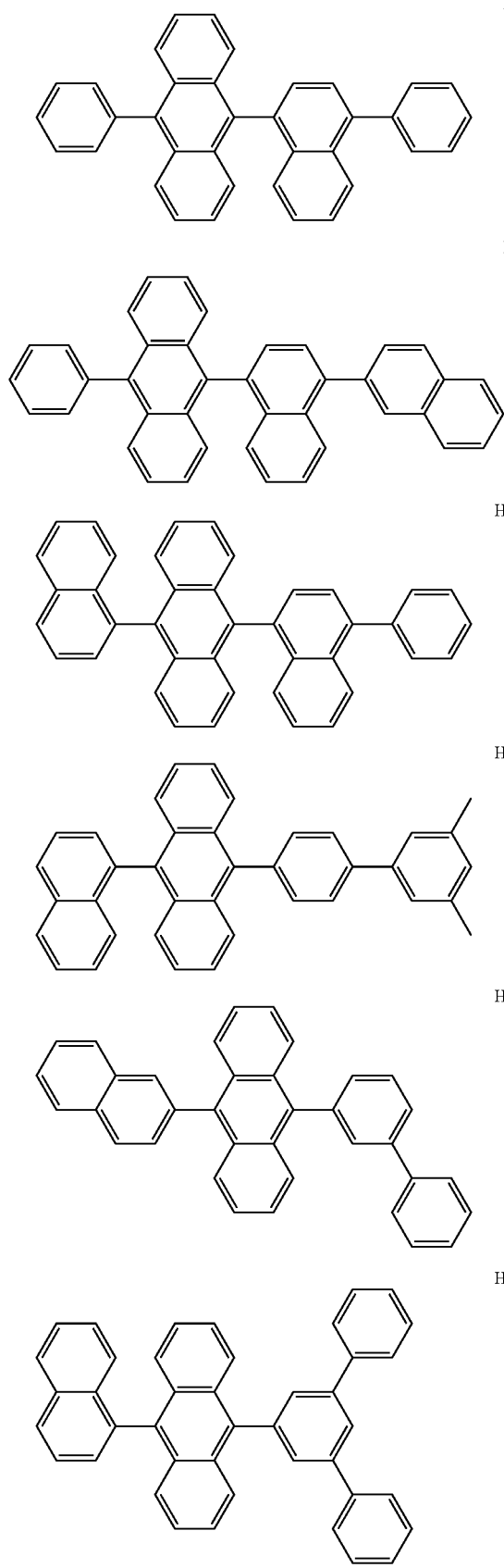
H8
H9
H10
H11
H12
H13
-continued
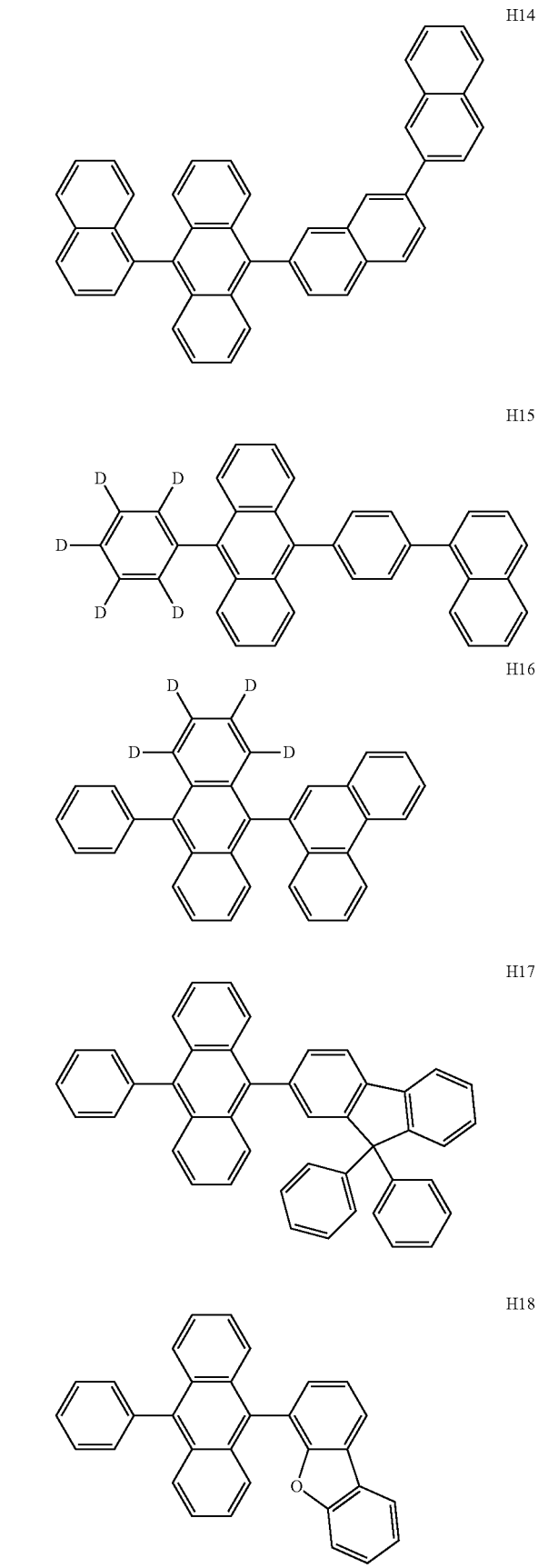
H14
H15
H16
H17
H18

H19
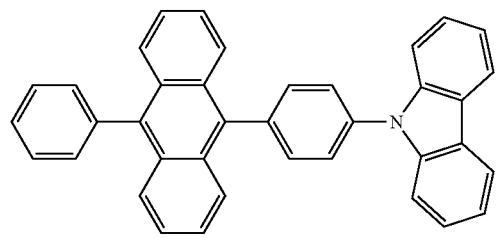
H20
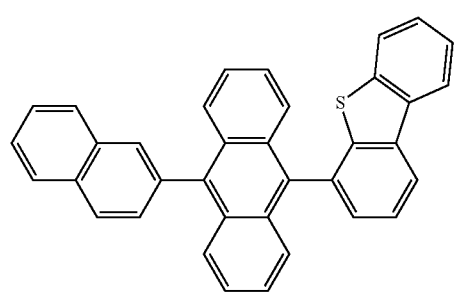
H21
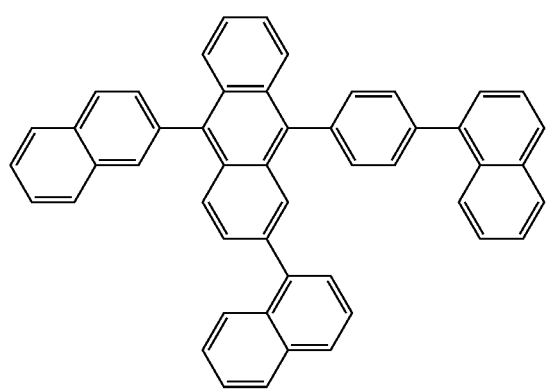
H22
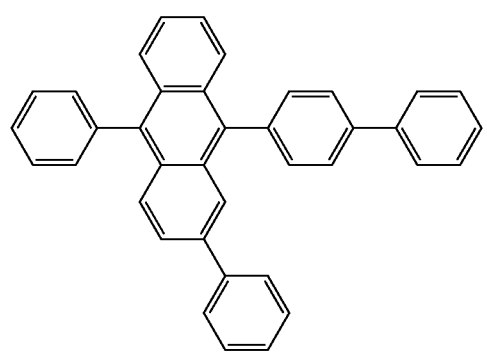
H23
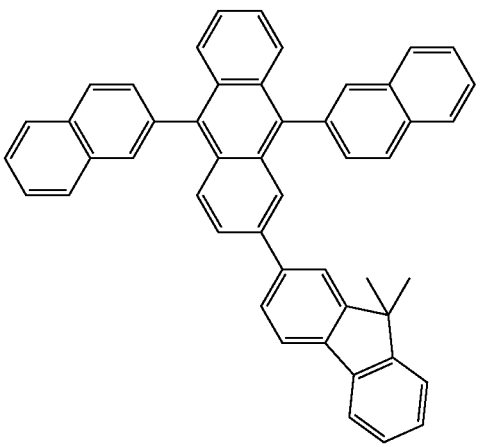
H24
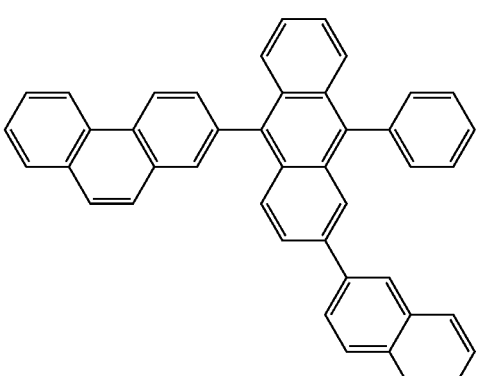
H25
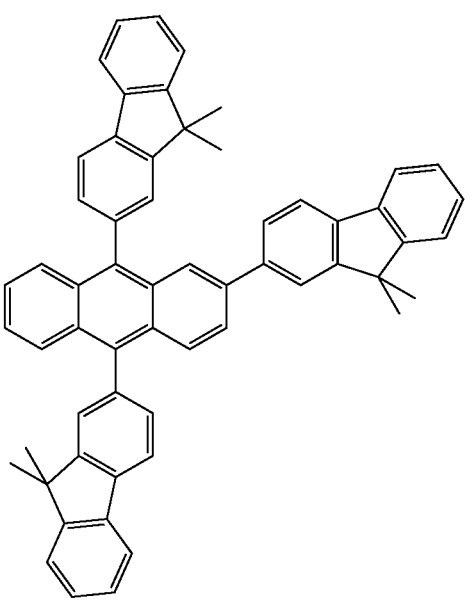

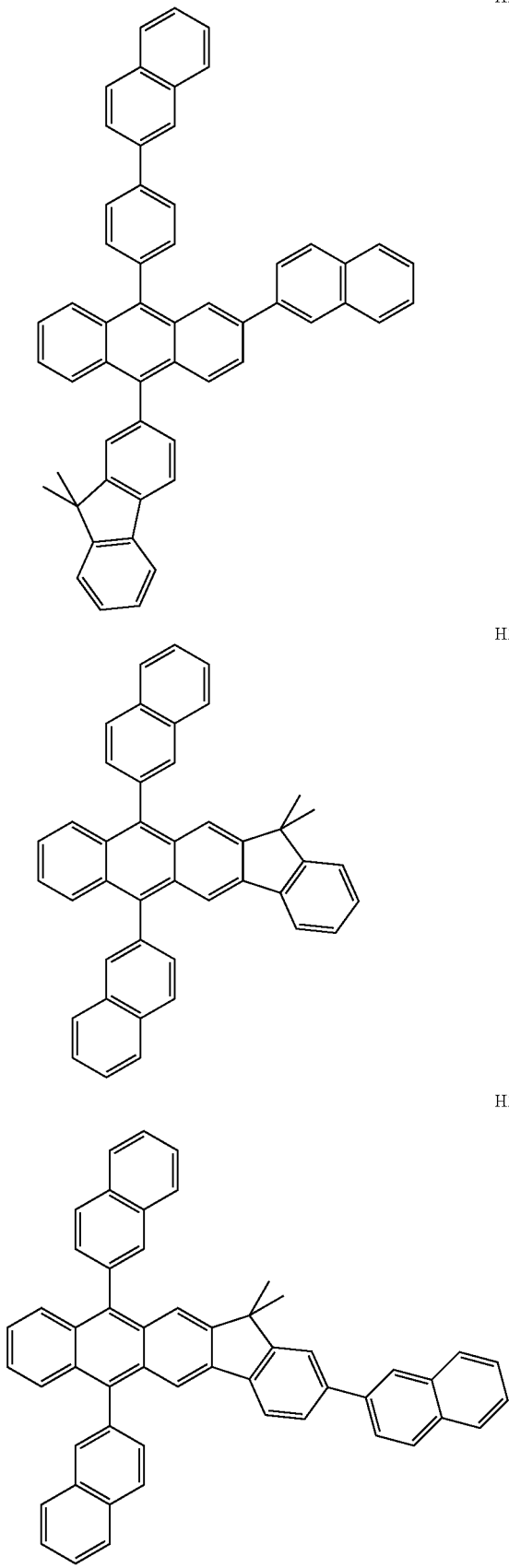
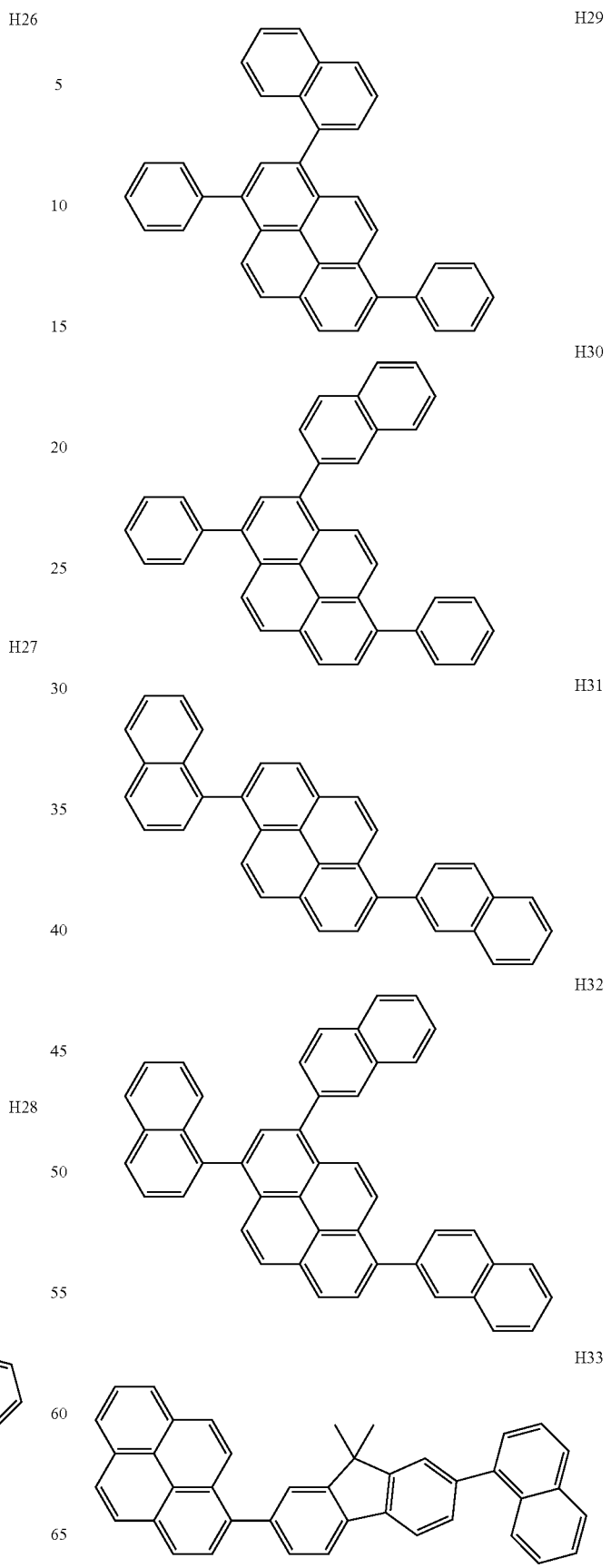

H34
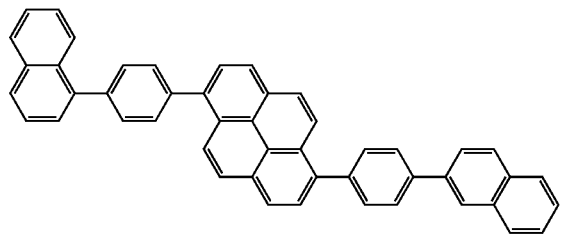
H35
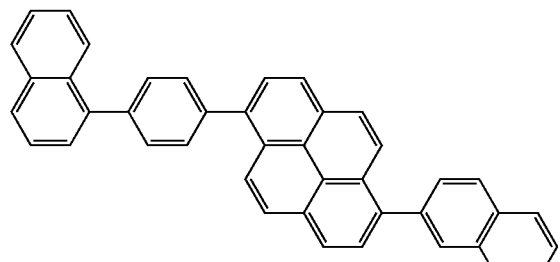
H36
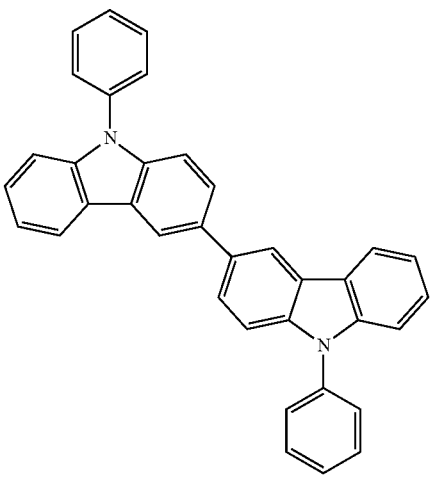
H37
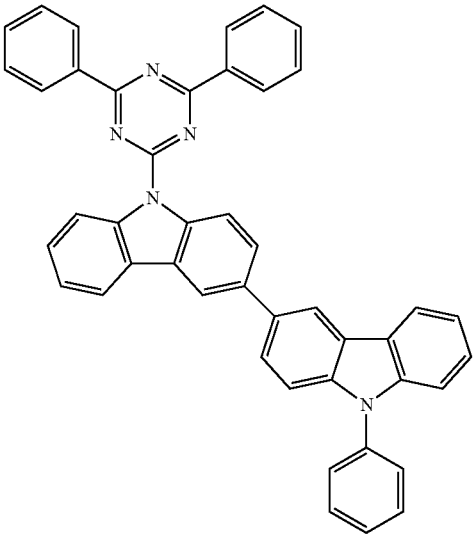
H38
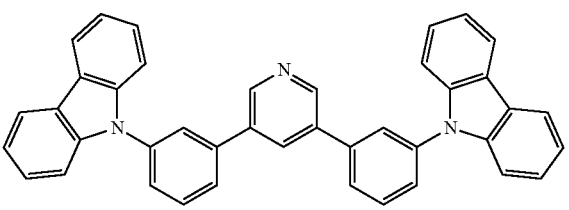
H39
H40

-continued
H41
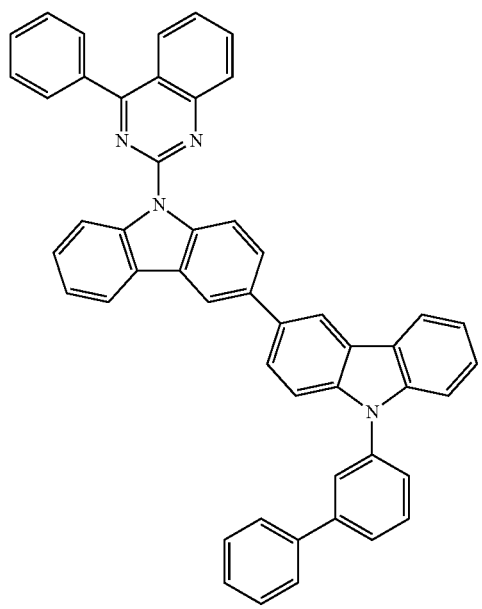
H42
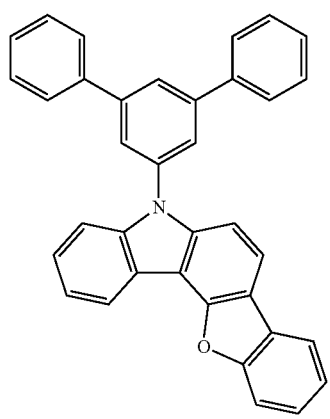
H43
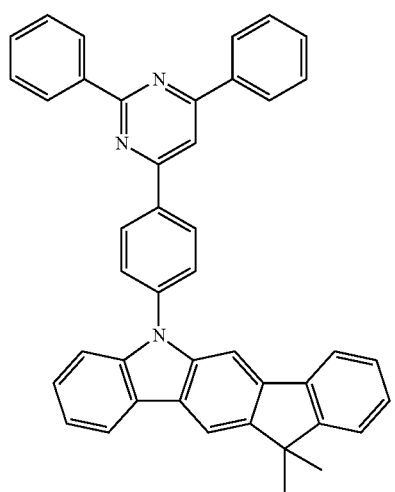
-continued
H44
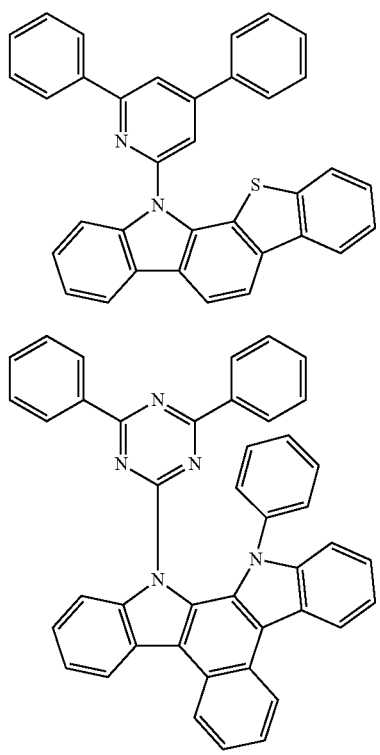
H45
H46
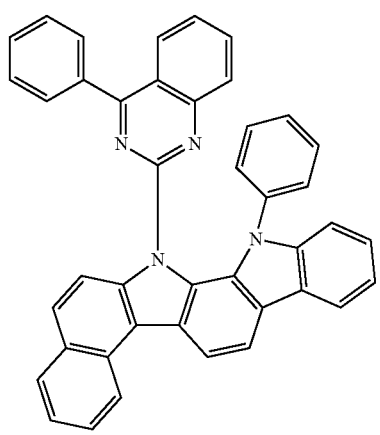
H47
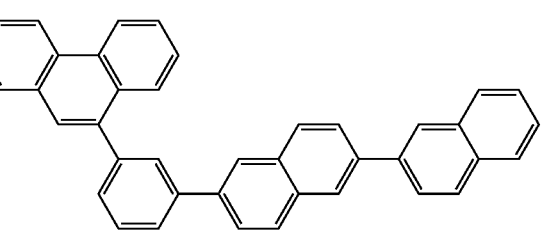
H48
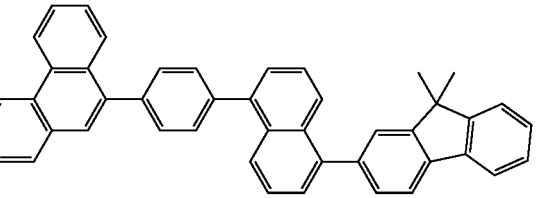

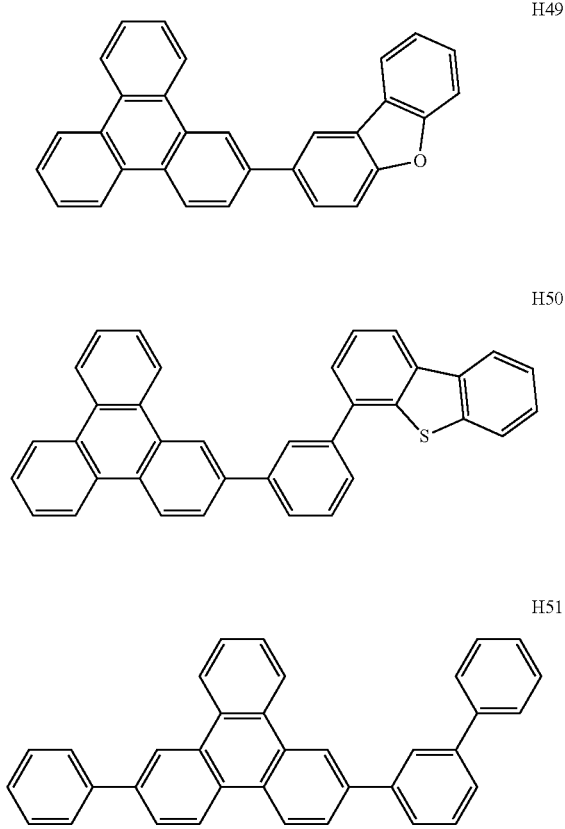

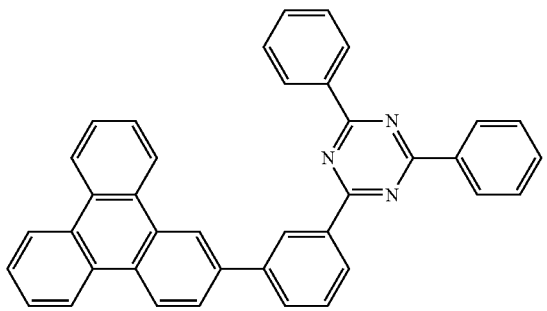

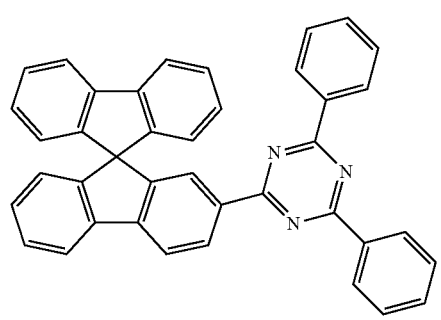

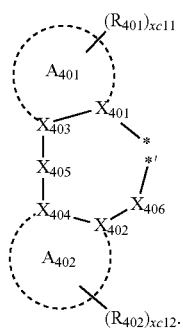

[Phosphorescent Dopant in Emission Layers 153-2b or 153-3b in Organic Layer 150]

The phosphorescent dopant may include an organic metal complex represented by Formula 401:

$$M(L_{401})_{xc1}(L_{402})_{xc2} \qquad \text{<Formula 401>}$$

<Formula 402>

In Formulae 401 and 402,

M may be selected from, for example, iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from a ligand represented by Formula 402, xc1 may be 1, 2, or 3, wherein, when xc1 is two or more, two or more $L_{401}$(s) may be identical to or different from each other, $L_{402}$ may be an organic ligand, xc2 may be an integer of 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked to each other via a single bond or a double bond, $X_{402}$ and $X_{404}$ may be linked to each other via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and in Formula 402, * and *' each indicate a binding site to M of Formula 401.

In an embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In an embodiment, in Formula 402, i) $X_{401}$ may be nitrogen and $X_{402}$ may be carbon, or ii) $X_{401}$ and $X_{402}$ may each be nitrogen at the same time.

In an embodiment, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group.

In an embodiment, in Formula 401, when xc1 is two or more, two $A_{401}$(s) among two or more $L_{401}$(s) may be optionally linked to each other through $X_{407}$, which is a linking group, or two $A_{402}$(s) among two or more $L_{401}$(s) may be optionally linked to each other through $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group).

In Formula 401, $L_{402}$ may be a monovalent, divalent, or trivalent organic ligand. For example, $L_{402}$ may be selected from a halogen, a diketone (for example, acetylacetonate), a carboxylic acid (for example, picolinate), —C(=O), isonitrile, —CN, and phosphorus containing material (for example, phosphine and phosphite).

In an embodiment, the phosphorescent dopant may be, for example, selected from Compounds PD1 to PD25, but embodiments ate not limited thereto:

PD1 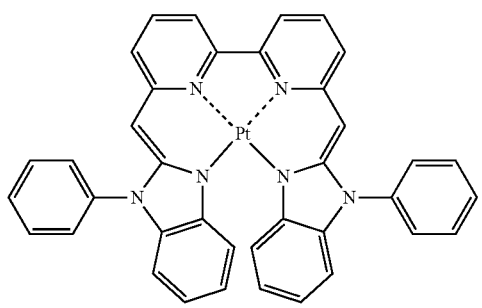
PD2 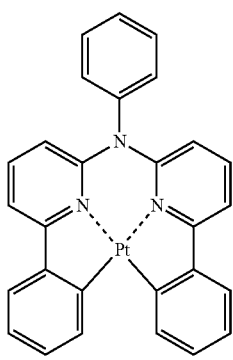
PD3 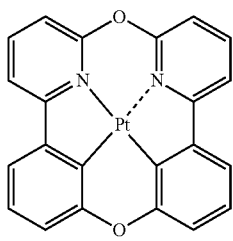
PD4 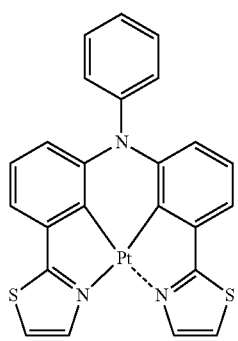
PD5 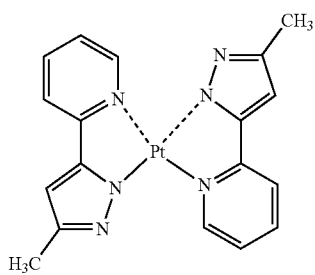
PD6 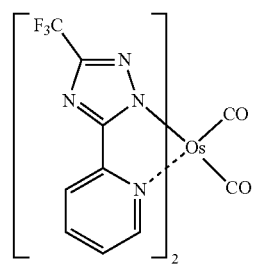
PD7 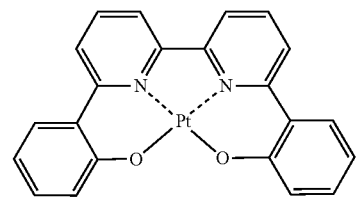
PD8 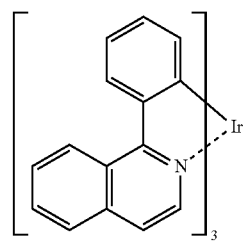
PD9 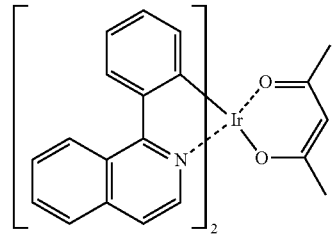
PD10 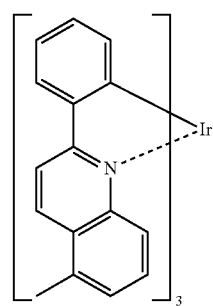
PD11 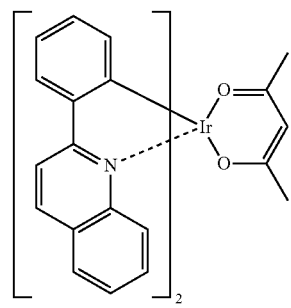

PD12 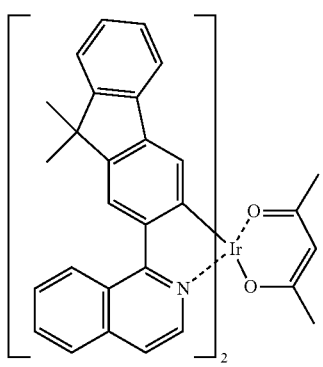
PD13 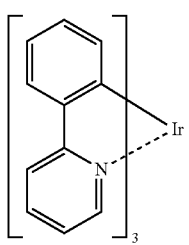
PD14 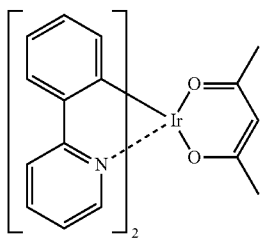
PD15 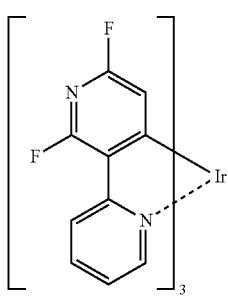
PD16 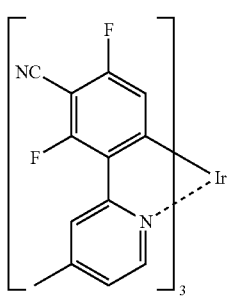
PD17 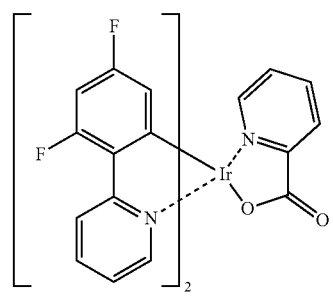
PD18 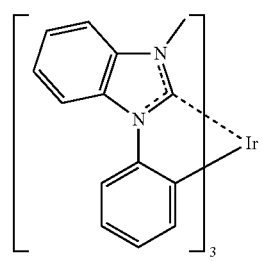
PD19 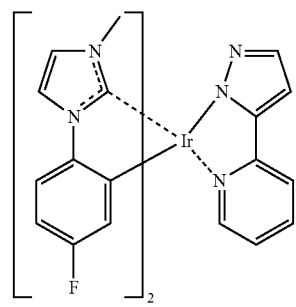
PD20 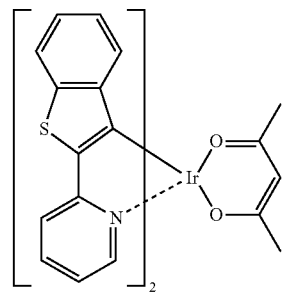
PD21 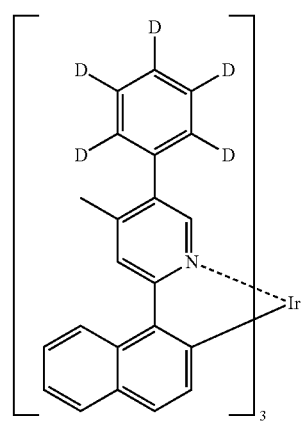

PD22

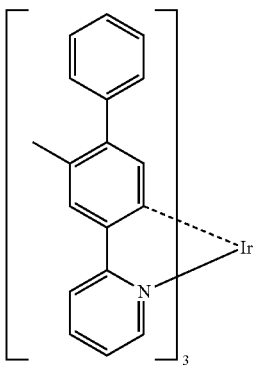

PD23

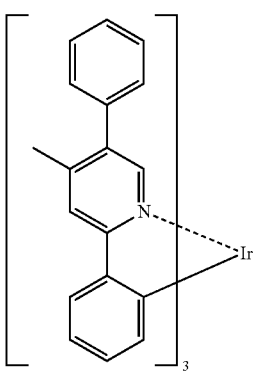

PD24

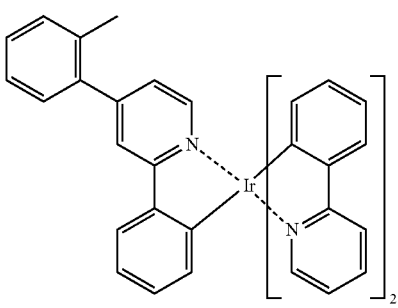

PD25

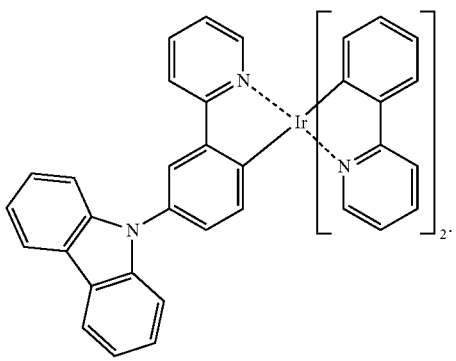

[Fluorescent Dopant in Emission Layers 153-2b or 153-3b]

The fluorescent dopant may include an arylamine compound or a styrylamine compound.

The fluorescent dopant may include a compound represented by Formula 501:

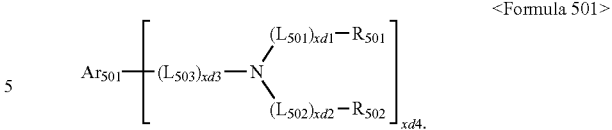

<Formula 501>

In Formula 501, $Ar_{501}$ may be a substituted or unsubstituted $C_5$-$C_{60}$ carbocyclic group, or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In an embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an embodiment, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, and a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In an embodiment, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an embodiment, in Formula 501, xd4 may be 2.

In an embodiment, the fluorescent dopant may be selected from Compounds FD1 to FD22:

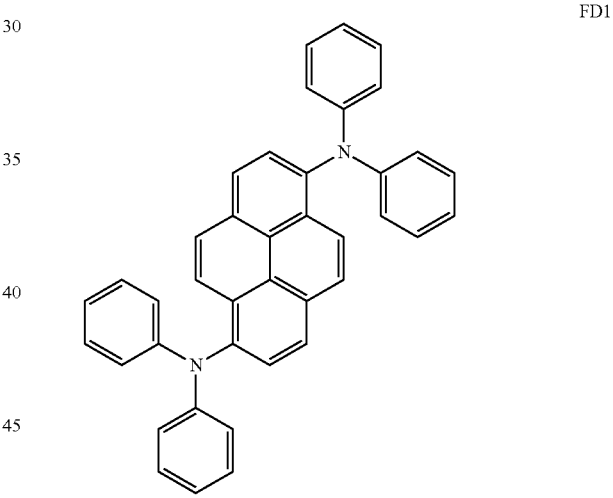

FD1

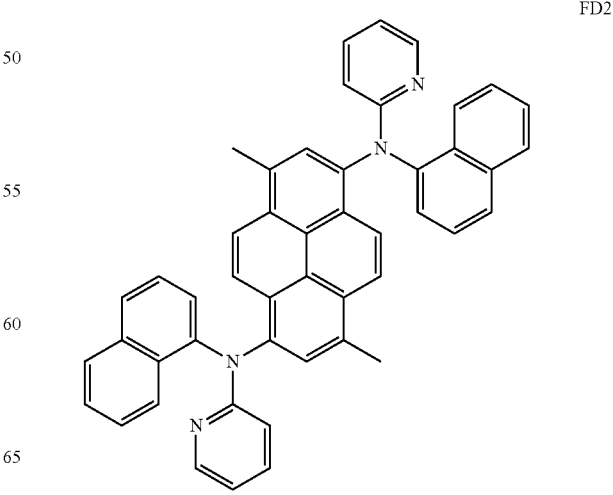

FD2

-continued
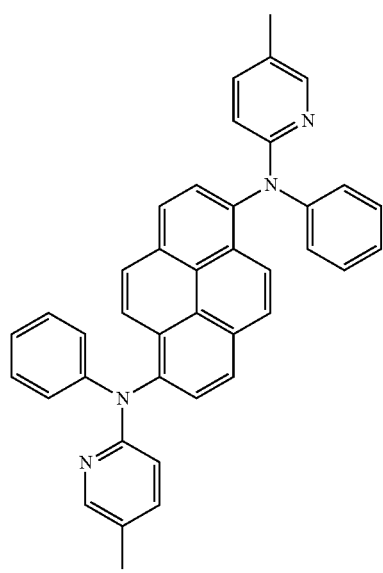
FD3
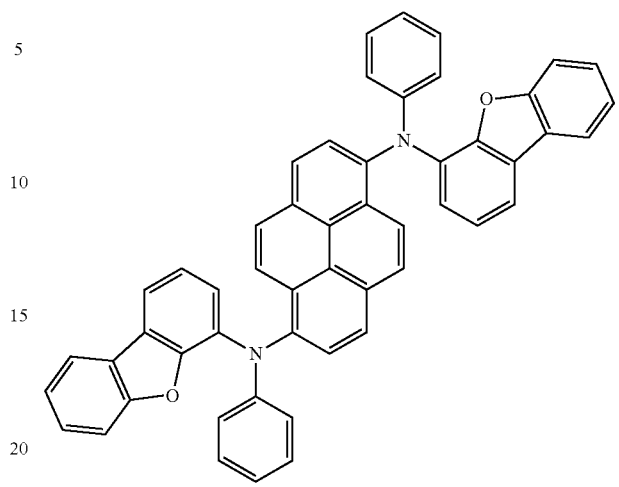
FD5
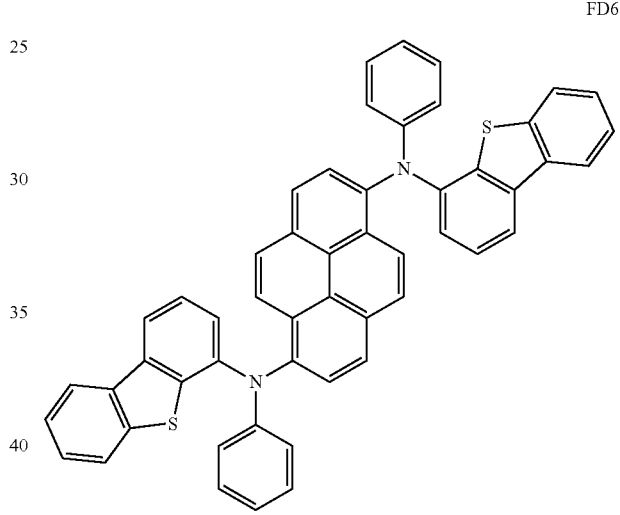
FD6
FD4
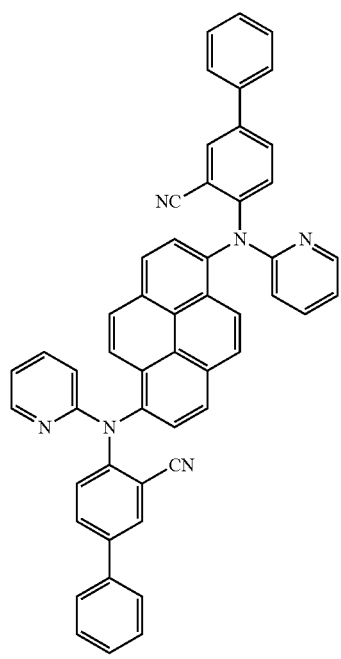
FD7
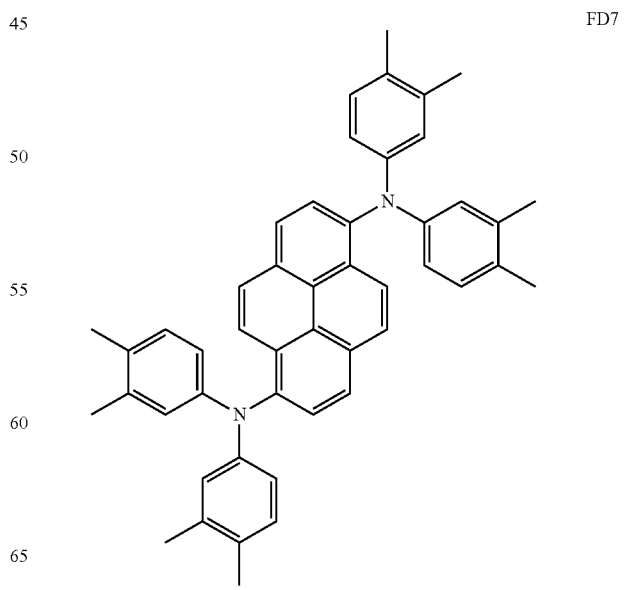

FD8
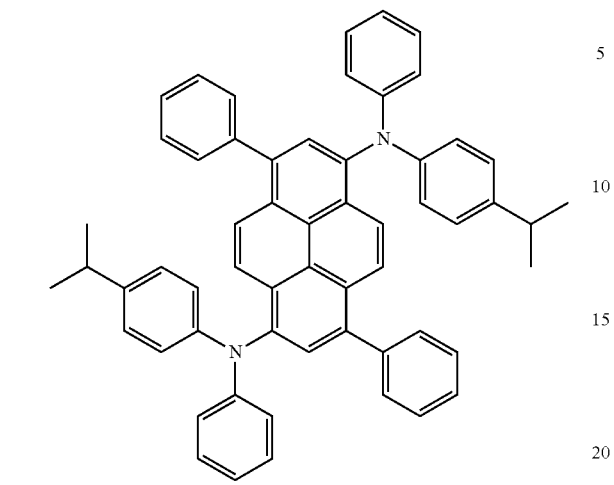
FD9
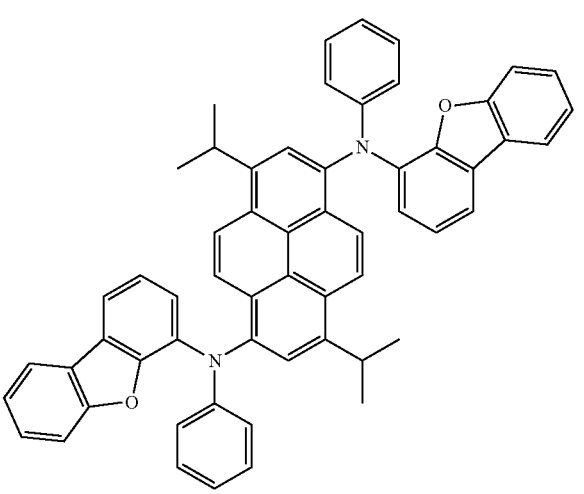
FD10
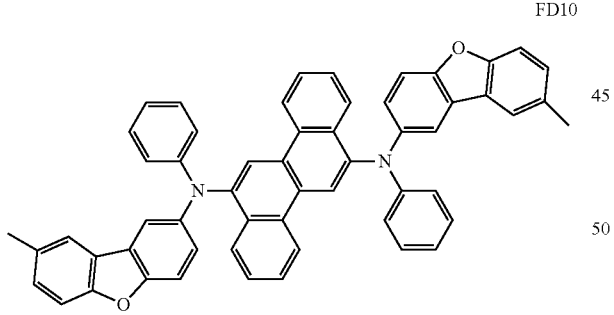
FD11
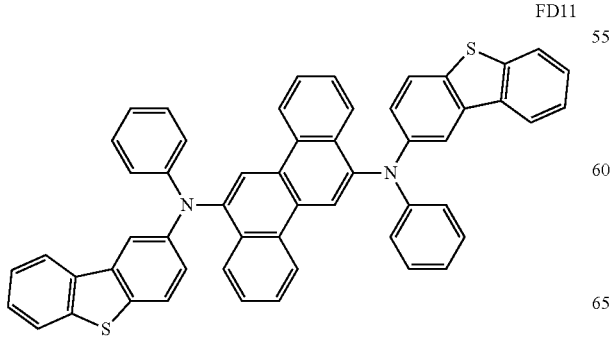
FD12
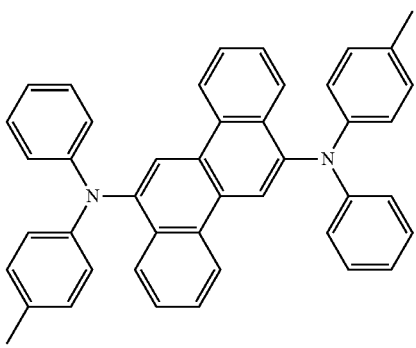
FD13
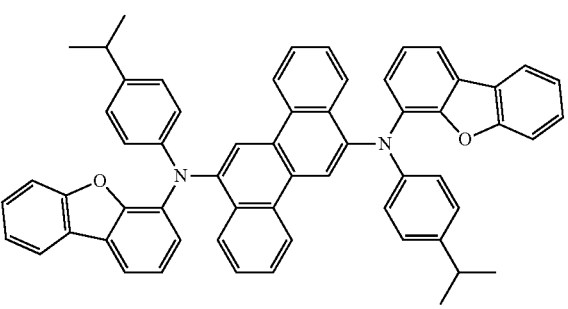
FD14
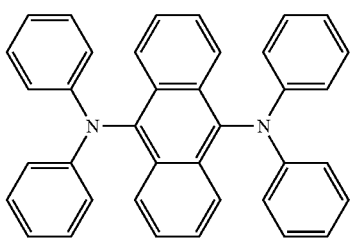
FD15
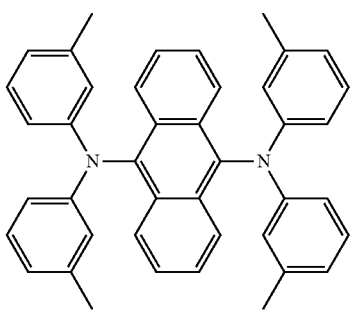
FD16
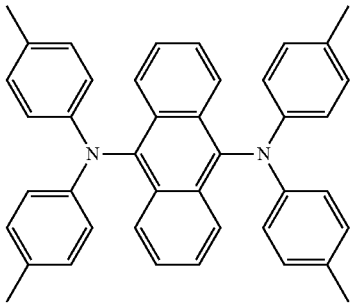

FD17
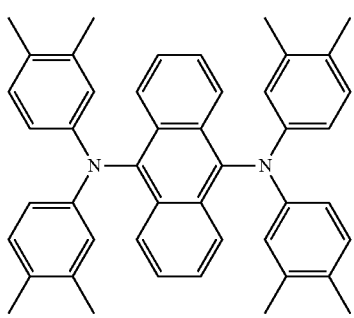
FD18
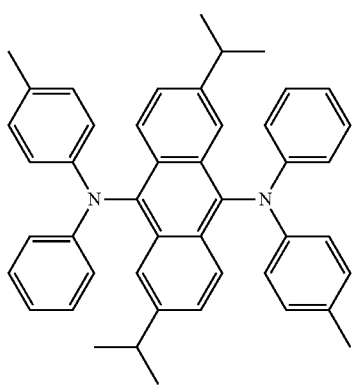
FD19
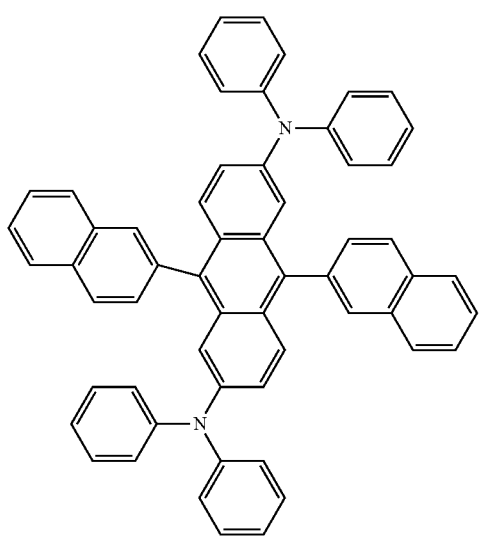
FD20
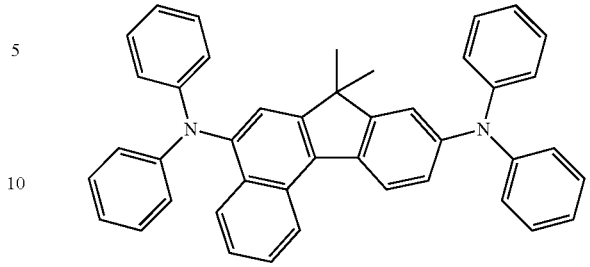
FD21
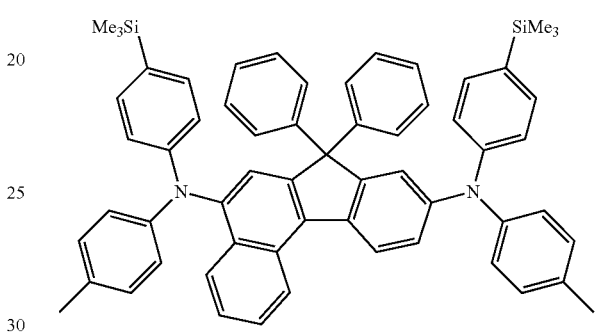
FD22
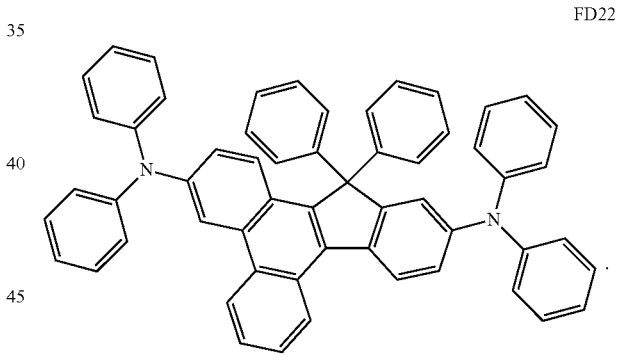
In an embodiment, the fluorescent dopant may be selected from compounds below:
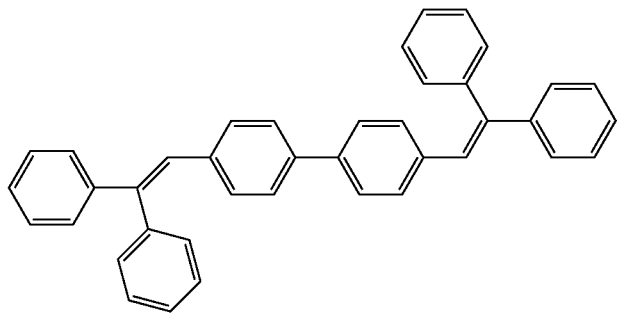
DPVBi

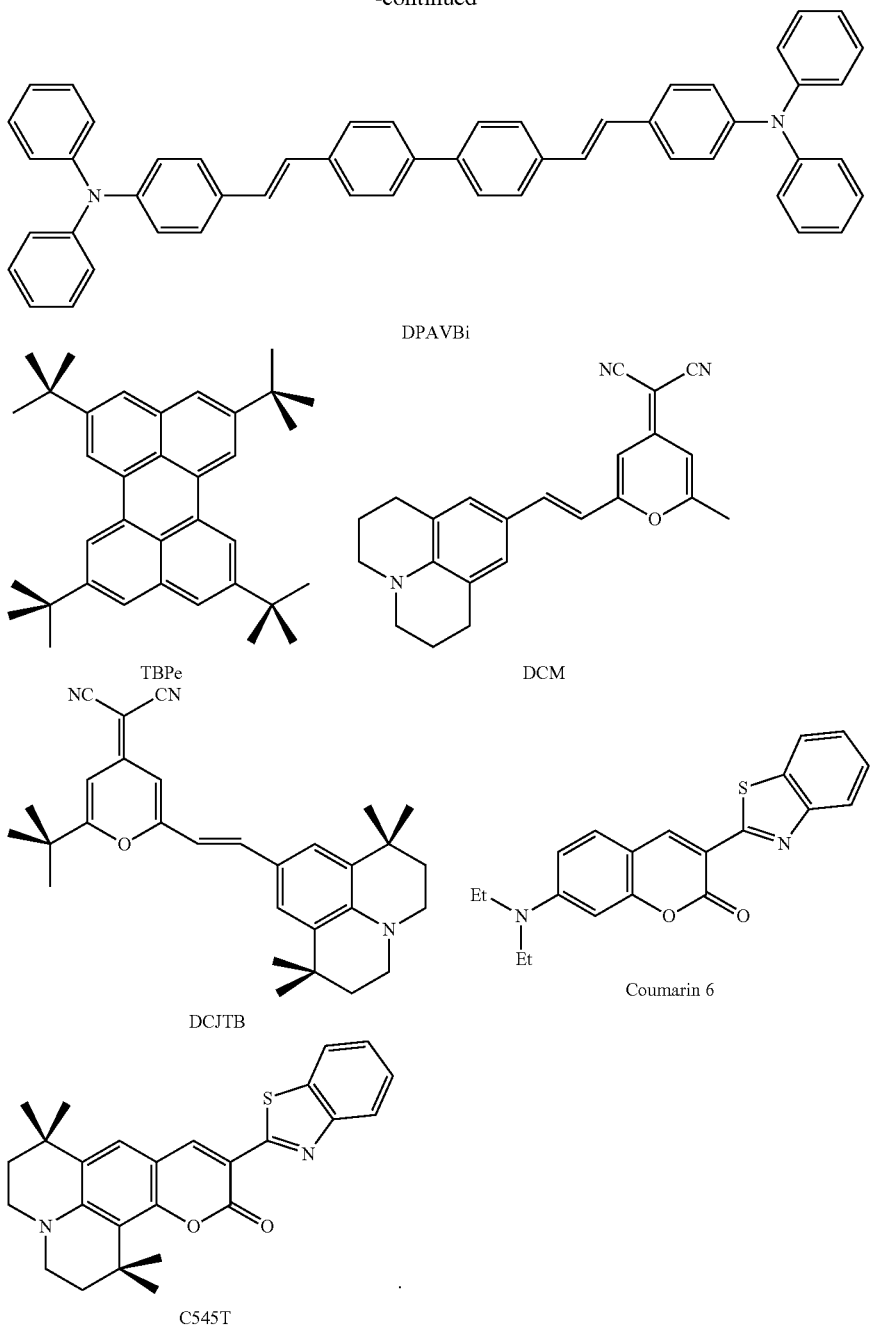

[Electron Transport Region in Organic Layer 150]

The electron transport region may have i) a single-layered structure including a single material, ii) a single-layered structure including a plurality of different materials, or iii) a multi-layered structure having a plurality of layers including a plurality of different materials.

The electron transport region may include at least one layer selected from a buffer layer, a hole blocking layer, an electron control layer, the electron transport layer 153-2c or 153-3c, and an electron injection layer.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from the emission layer in their stated orders, but the structure of the electron transport region is not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring electron" indicates a $C_1$-$C_{60}$ heterocyclic group including at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one 5-membered to 7-membered heteromonocyclic group having at least one *—N=*' moiety is condensed with at least one $C_5$-$C_{60}$ carbocyclic group.

Non-limiting examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, phenanthroline, a phenazine, a benzimidazole, an isobenzothiazole, a benzoxazole, an isobenzoxazole, a triazole, a tetrazole, an oxadiazole, a triazine, a thiadiazol, an imidazopyridine, an imidazopyrimidine, and an azacarbazole.

For example, the electron transport region may include a compound represented by Formula 601.

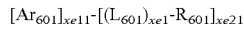  <Formula 601>

In Formula 601, $Ar_{601}$ may be a substituted or unsubstituted $C_5$-$C_{60}$ carbocyclic group, or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer of 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In an embodiment, at least one selected from xe11 $Ar_{601}$(s) and at least one selected from xe21 $R_{601}$(s) may include the π0 electron-depleted nitrogen-containing ring as described above.

In an embodiment, in Formula 601, ring $Ar_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 601, when xe11 is two or more, two or more $Ar_{601}$(s) may be linked to each other via a single bond.

In an embodiment, in Formula 601, $Ar_{601}$ may be an anthracene group.

In an embodiment, the compound represented by 601 may be represented by Formula 601-1:

<Formula 601-1>

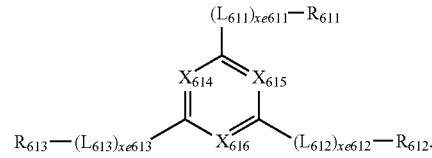

In Formula 601-1, $X_{614}$ may be N or $C(R_{614})$, $X_{615}$ may be N or $C(R_{615})$, and $X_{616}$ may be N or $C(R_{616})$, wherein at least one selected from $X_{614}$ to $X_{616}$ may be nitrogen, $L_{611}$ to $L_{613}$ may each independently be as defined herein in connection with $L_{601}$, xe611 to xe613 may each independently be as defined herein in connection with xe1, $R_{611}$ to $R_{613}$ may each independently be as defined herein in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group.

In an embodiment, in Formulae 601 and 601-1, xe1 and xe611 to xe613 may each independently be 0, 1, or 2.

In an embodiment, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may each independently be as defined herein.

In an embodiment, the electron transport region may include at least one compound selected from Compounds ET1 to ET36:

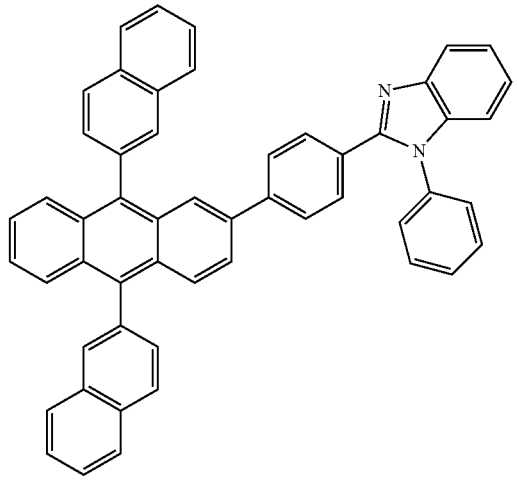

ET1

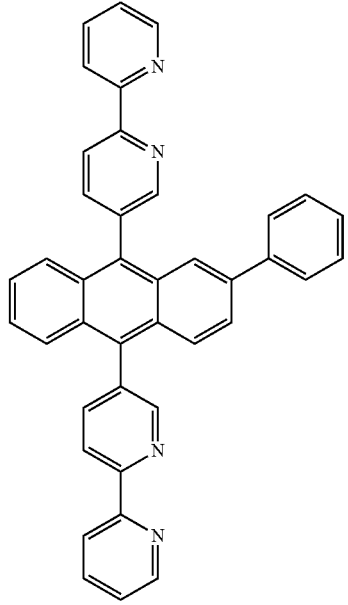

ET2

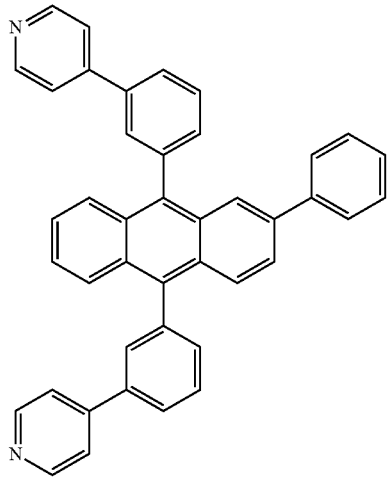

ET3

ET4
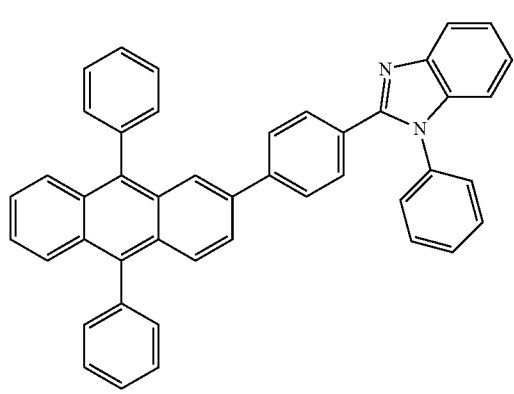
ET7
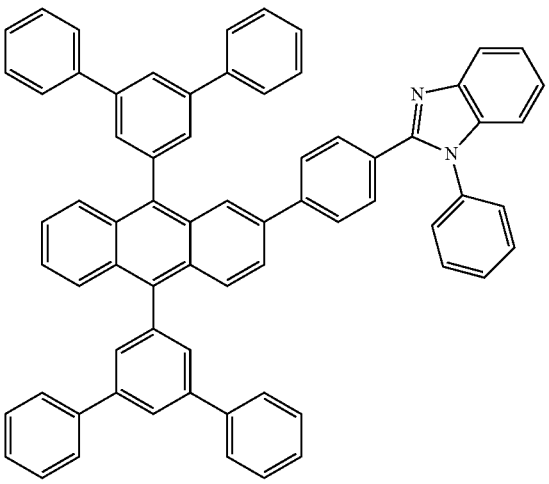
ET5
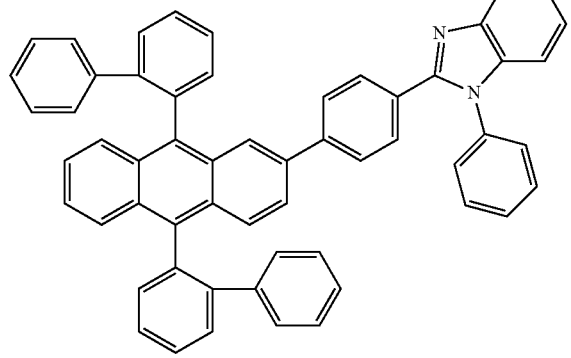
ET8
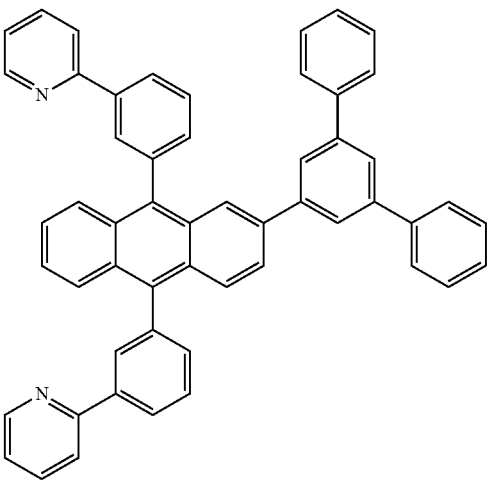
ET6
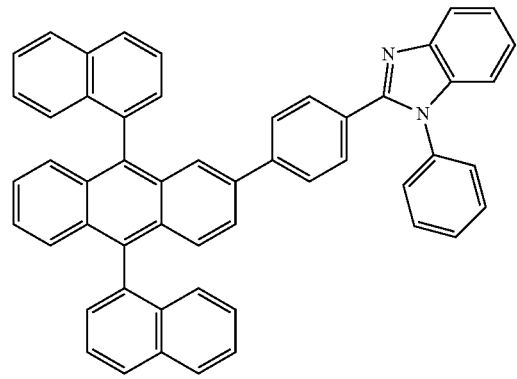
ET9
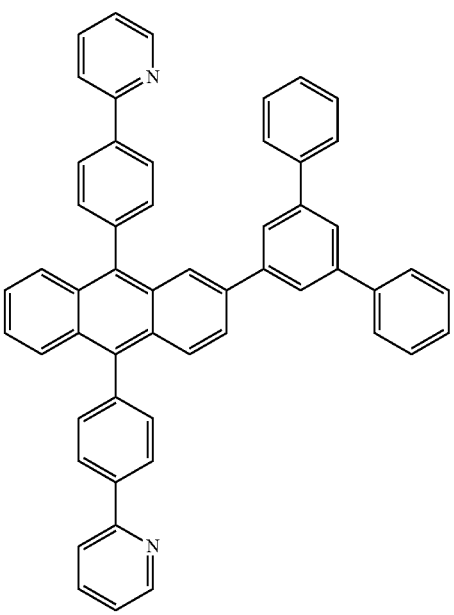

ET10 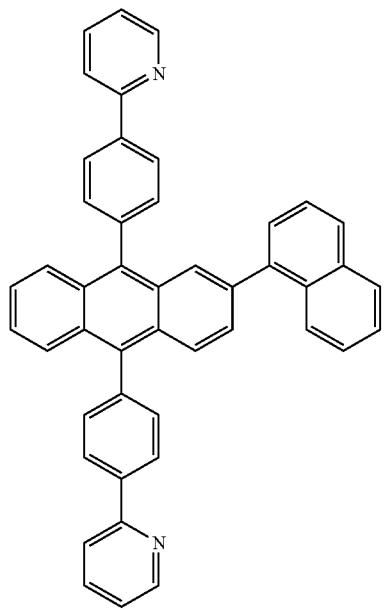
ET13 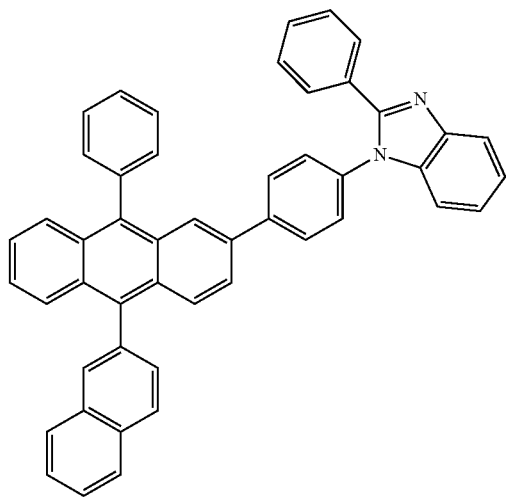
ET11 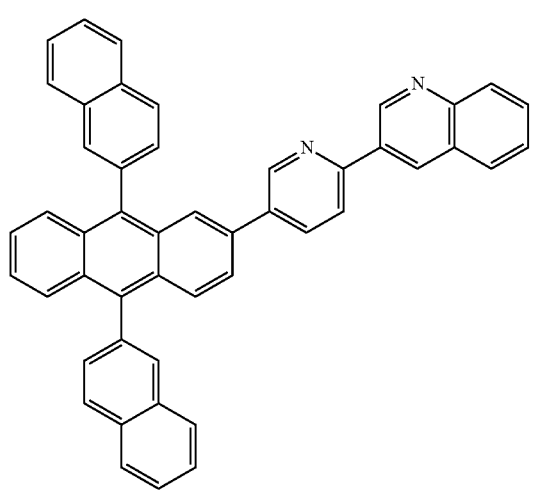
ET14 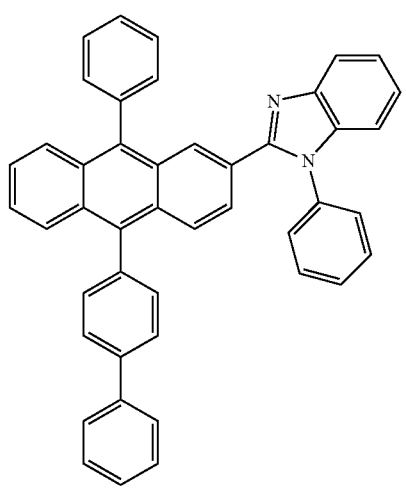
ET12 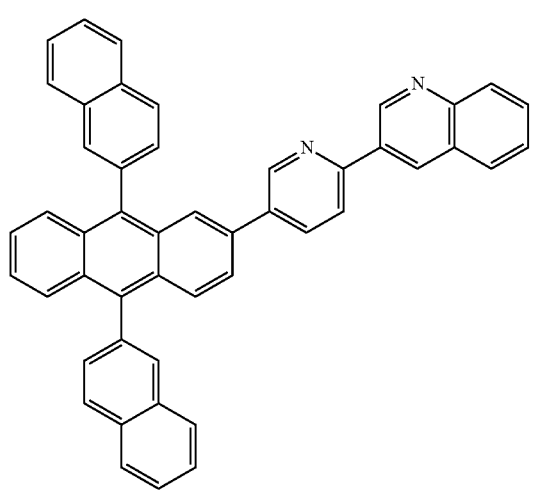
ET15 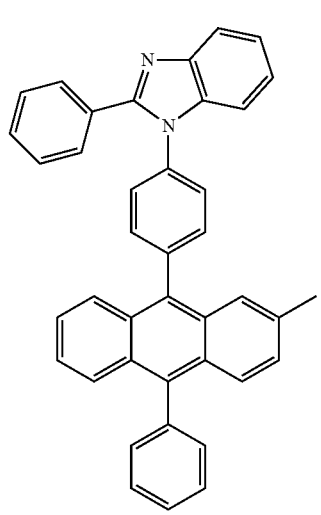

ET16
ET17
ET18
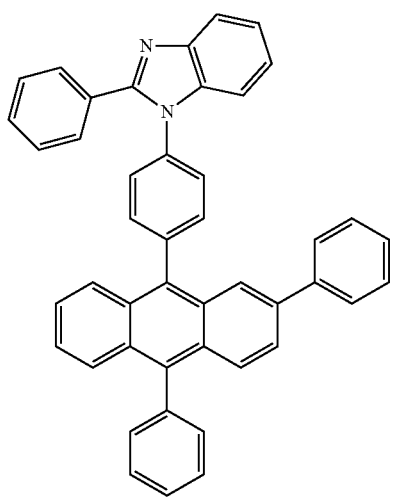
ET19
ET20
ET21
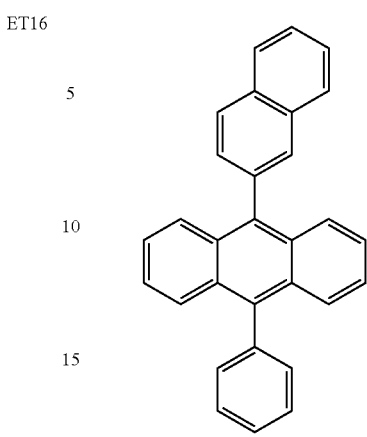

ET22
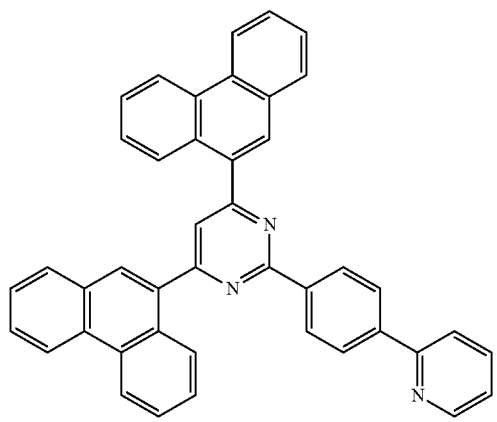
ET23
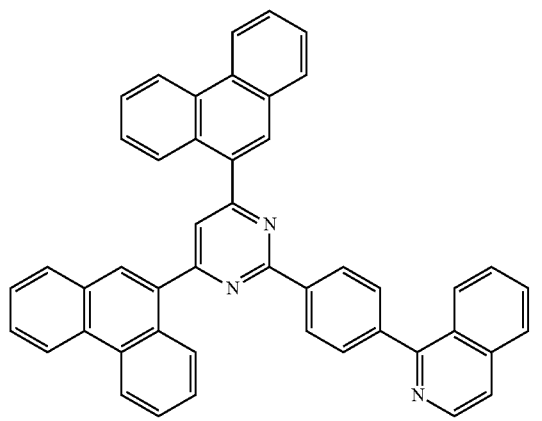
ET24
ET25
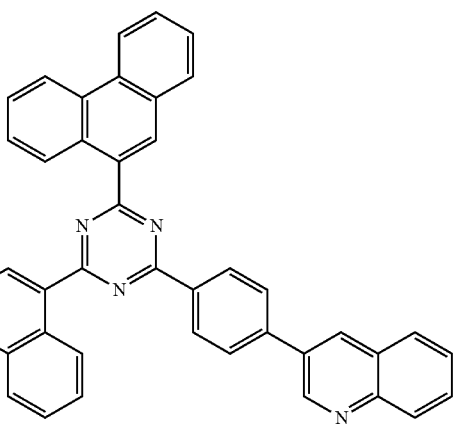
ET26
ET27
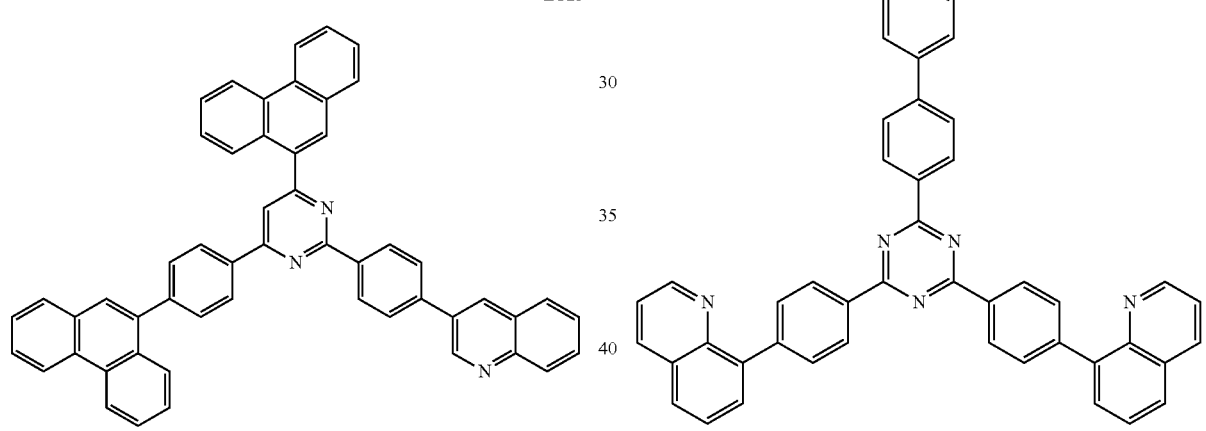
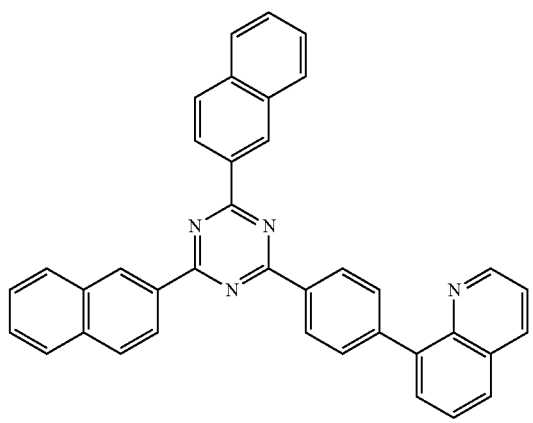

ET28
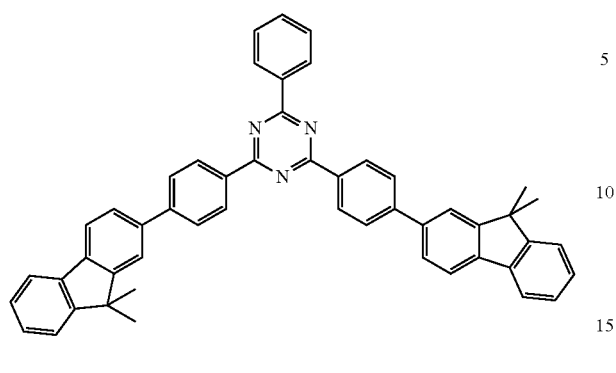
ET29
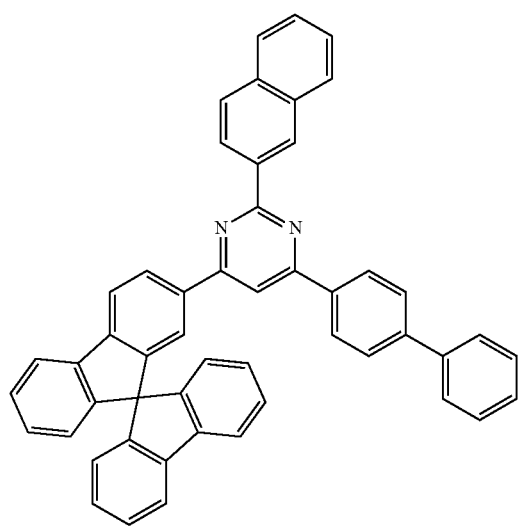
ET30
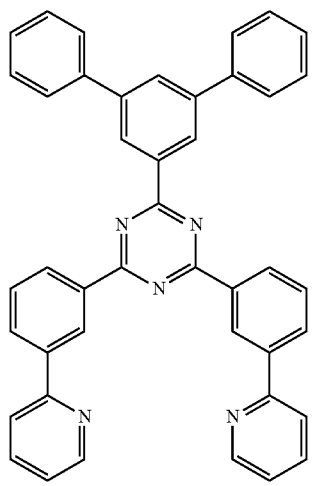
ET31
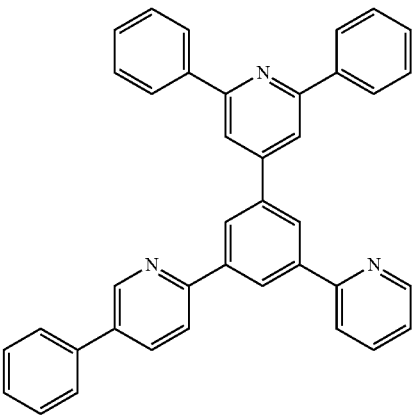
ET32
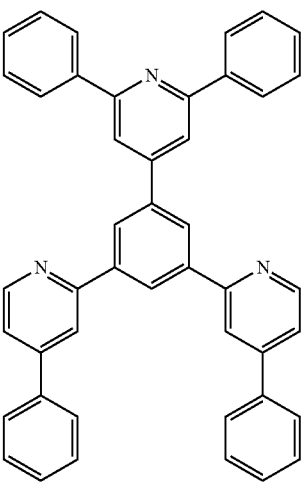
ET33
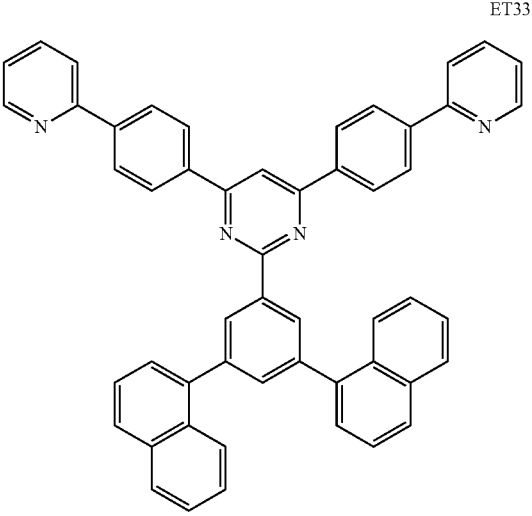

ET34

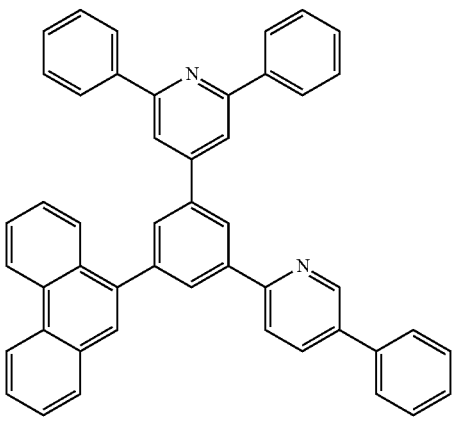

ET35

ET36

In an embodiment, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ:

Alq₃

BAlq

TAZ

NTAZ

A thickness of the buffer layer, the hole blocking layer, or the electron control layer may be, for example, in a range from about 20 Å to about 1,000 Å, for example, about 30 Å to about 300 Å. When the thickness of the buffer layer, the hole blocking layer, or the electron control layer is within any of these ranges, excellent hole blocking characteristics and/or electron control characteristics may be obtained without a substantial increase in driving voltage.

A thickness of the electron transport layer may be, for example, in a range from about 100 Å to about 1,000 Å, for example, about 150 Å to about 500 Å. When the thickness of the electron transport layer is within any of these ranges, satisfactory electron transport characteristics may be obtained without a substantial increase in driving voltage.

The electron transport region (for example, an electron transport layer in the electron transport region) may further include, in addition to the materials described above, a metal-containing material.

The metal-containing material may include, for example, at least one selected from an alkali metal complex and an alkaline earth metal complex. The alkali metal complex may include, for example, a metal ion selected from a Li ion, a Na ion, a K ion, a Rb ion, and a cesium (Cs) ion, and the alkaline earth metal complex may include, for example, a metal ion selected from a beryllium (Be) ion, a Mg ion, a Ca ion, a strontium (Sr) ion, and a barium (Ba) ion. Each ligand coordinated with the metal ion of the alkali metal complex or the alkaline earth metal complex may independently be selected from, for example, a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenylan oxadiazole, a hydroxydiphenylthiadiazol, a hydroxyphenyl pyridine, a hydroxyphenyl benzimidazole, a hydroxyphenyl benzothiazole, a bipyridine, a phenanthroline, and a cyclopentadiene.

For example, the metal-containing material may include a Li complex. The Li complex may include, for example, Compound ET-D1 (lithium quinolate, LiQ) and/or ET-D2:

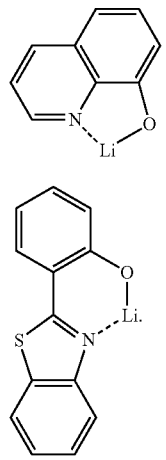

ET-D1

ET-D2

The electron transport region may include an electron injection layer that facilitates injection of electrons from the second electrode 190. The electron injection layer may directly contact the second electrode 190.

The electron injection layer may have, for example, i) a single-layered structure including a single material, ii) a single-layered structure including a plurality of different materials, or iii) a multi-layered structure having a plurality of layers including a plurality of different materials.

The electron injection layer may include, for example, an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from Li, Na, K, Rb, and Cs. In an embodiment, the alkali metal may be Li, Na, or Cs. In an embodiment, the alkali metal may be Li or Cs.

The alkaline earth metal may be selected from Mg, Ca, Sr, and Ba.

The rare earth metal may be selected from, for example, scandium (Sc), yttrium (Y), cerium (Ce), ytterbium (Yb), gadolinium (Gd), and terbium (Tb).

The alkali metal compound, the alkaline earth metal compound, and the rare earth metal compound may be respectively selected from oxides and halides (for example, fluorides, chlorides, bromides, and/or iodides) of the alkali metal, the alkaline earth metal, and the rare earth metal.

The alkali metal compound may be selected from alkali metal oxides, such as $Li_2O$, $Cs_2O$, and $K_2O$, and alkali metal halides, such as LiF, NaF, CsF, KF, LiI, NaI, CsI, KI, and RbI. In an embodiment, the alkali metal compound may be selected from LiF, $Li_2O$, NaF, LiI, NaI, CsI, and KI.

The alkaline earth metal compound may be selected from alkaline earth metal compounds, such as BaO, SrO, CaO, $Ba_xSr_{1-x}O$ (wherein 0<x<1), and $Ba_xCa_{1-x}O$ (wherein 0<x<1). In an embodiment, the alkaline earth metal compound may be selected from BaO, SrO, and CaO.

The rare earth metal compound may be selected from, for example, $YbF_3$, $ScF_3$, $ScO_3$, $Y_2O_3$, $Ce_2O_3$, $GdF_3$, and $TbF_3$. In an embodiment, the rare earth metal compound may be selected from $YbF_3$, $ScF_3$, $TbF_3$, $YbI_3$, $ScI_3$, and $TbI_3$.

The alkali metal complex, the alkaline earth metal complex, and the rare earth metal complex may each include an alkali metal ion, an alkaline earth metal ion, and a rare earth metal ion as described above, respectively, and each ligand coordinated with a metal ion of the alkali metal complex, the alkaline earth metal complex, and the rare earth metal complex may independently be selected from, for example, a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazol, a hydroxyphenyl pyridine, a hydroxyphenyl benzimidazole, a hydroxyphenyl benzothiazole, a bipyridine, a phenanthroline, and a cyclopentadiene.

The electron injection layer may include only the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof. In various embodiments, the electron injection layer may further include an organic material. When the electron injection layer further includes the organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

A thickness of the electron injection layer may be, for example, in a range from about 1 Å to about 100 Å, for example, about 3 Å to about 90 Å. When the thickness of the electron injection layer is in any of these ranges, satisfactory electron injection characteristics may be obtained without a substantial increase in driving voltage.

[Second Electrode 190]

The second electrode 190 may be disposed on the organic layer 150. The second electrode 190 may be, for example, a cathode, which is an electron injection electrode, and in this regard, a material for forming the second electrode 190 may be selected from, for example, a metal, an alloy, an electrically conductive compound, and a mixture thereof, which have a relatively low work function.

The second electrode 190 may include, for example, at least one selected from Li, Ag, Mg, Al, Al—Li, Ca, Mg—In, Mg—Ag, ITO, and IZO. The second electrode 190 may be, for example, a transmissive electrode, a semi-transmissive electrode, or a reflective electrode.

The second electrode 190 may have a single-layered structure or a multi-layered structure including two or more layers.

Hereinbefore, the organic light-emitting device has been described with reference to FIGS. 1 to 5.

The layers constituting the hole transport region, the emission layer, and the layers constituting the electron transport region may each be formed in a specific region using one or more suitable methods selected from, for example, vacuum deposition, spin coating, casting, a Langmuir-Blodgett (LB) method, ink-jet printing, laser printing, and laser induced thermal imaging (LITI).

When the layers constituting the hole transport region, the emission layer, and the layers constituting the electron transport region are each formed by vacuum deposition, for example, the vacuum deposition may be performed at a deposition temperature in a range from about 100° C. to about 500° C., at a vacuum degree in a range from about $10^{-8}$ torr to about $10^{-3}$ torr, and a deposition rate in a range from about 0.01 Å/sec to about 100 Å/sec, depending on a compound to be included in each layer and an intended structure of each layer.

When the layers constituting the hole transport region, the emission layer, and the layers constituting the electron transport region are each formed by spin coating, for example, the spin coating may be performed at a coating rate of about 2,000 rpm to about 5,000 rpm and at a temperature of about 80° C. to about 200° C., depending on the compound to be included in each layer and the intended structure of each layer.

[General Definition of Substituents]

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a ter-butyl group, a pentyl group, an iso-amyl group, and a hexyl group. The term "$C_1$-$C_{60}$ alkylene group" as used herein refers to a divalent group of the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group of the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group of the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group of the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group of the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group of the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group of the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. An example of the monovalent non-aromatic condensed polycyclic group includes a fluorenyl group. The term "divalent non-aromatic condensed polycyclic group" as used herein refers to a divalent group of the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, has a heteroatom selected from N, O, Si, P, and S, other than carbon atoms, as a ring-forming atom, and has no aromaticity in its entire molecular structure. An example of the monovalent non-aromatic condensed heteropolycyclic group includes a carbazolyl group. The term "divalent non-aromatic condensed heteropolycyclic group" as used herein refers to a divalent group of the monovalent non-aromatic condensed heteropolycyclic group.

The term "$C_5$-$C_{60}$ carbocyclic group" as used herein refers to a monocyclic or polycyclic group having only carbon atoms as ring-forming atoms (for example, 5 to 60 carbon atoms). The $C_5$-$C_{60}$ carbocyclic group may be a carbocyclic group or a non-aromatic carbocyclic group. The $C_5$-$C_{60}$ carbocyclic group may be a benzene ring, a monovalent group such as a phenyl group, or a divalent group such as a phenylene group. In an embodiment, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_5$-$C_{60}$ carbocyclic group, but including at least one heteroatom selected from N, O, Si, P, and S, other than carbon atoms (for example, 1 to 60 carbon atoms), as ring-forming atoms.

At least one substituent selected from the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The expression "Ph" as used herein refers to a phenyl group, the expression "Me" as used herein refers to a methyl group, the expression "Et" as used herein refers to an ethyl group, the expression "ter-Bu" or "tBut" as used herein refers to a tert-butyl group, and the expression "OMe" as used herein refers to a methoxy group.

The term "biphenyl group" as used herein refers to "a phenyl group substituted with a phenyl group". In other words, a biphenyl group is a substituted phenyl group having a $C_6$-$C_{60}$ aryl group as a substituent.

The term "terphenyl group" as used herein refers to "a phenyl group substituted with a biphenyl group". In other words, a terphenyl group is a substituted phenyl group having a $C_6$-$C_{60}$ aryl group as a substituent.

The symbols * and *' as used herein, unless defined otherwise, refer to a binding site to a neighboring atom in a corresponding formula.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples. The expression "B was used instead of A" used in describing Synthesis Examples may refer to an identical number of molar equivalents of A being used in place of molar equivalents of B.

EXAMPLES

Example 1

As a substrate and an anode, an ITO glass substrate (a product of Corning Co., Ltd) having a thickness of 15 Ω/cm² (150 Å) was cut to a size 50 mm×50 mm×0.7 mm, sonicated by using isopropyl alcohol and pure water for 5 minutes each, and cleaned by exposure to ultraviolet rays and ozone for 30 minutes, and the resulting ITO glass substrate was mounted on a vacuum deposition apparatus.

TATC (100 Å), HAT-CN (50 Å), and NPB (100 Å) were sequentially deposited in the stated order on the ITO glass substrate to form a hole transport region.

Compound HT1 (100 Å) was deposited on the hole transport region to form an HT-auxiliary layer, AND and DPAVBi (having an amount of about 5 weight %) were co-deposited on the HT-auxiliary layer to form an emission layer having a thickness of about 200 Å, and Alq (50 Å) was deposited on the emission layer to form an ET-auxiliary layer, thereby forming a first light-emitting unit.

Then, Yb (having an amount of about 2 weight %) was deposited on the first light-emitting unit to form an n-type charge generation layer having a thickness of 150 Å, and Compound 1 (100 Å) was deposited on the n-type charge generation layer to form a p-type charge generation layer, thereby forming a first charge generation layer.

(Compound 1)

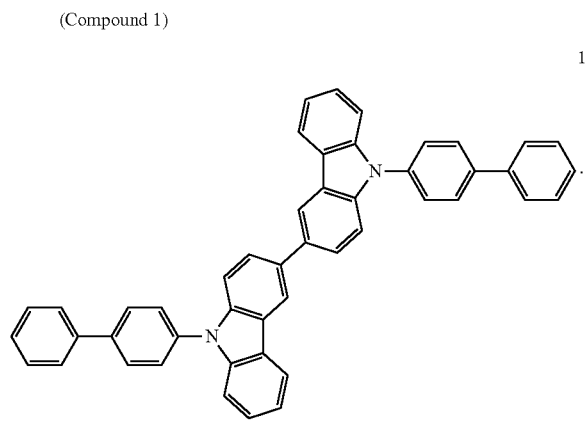

1

Compound HT1 (200 Å) was deposited on the first charge generation layer to form an HT-auxiliary layer, CBP and (BT)$_2$Ir(acac) (having an amount of about 15 weight %) were co-deposited on the HT-auxiliary layer to form an emission layer having a thickness of 200 Å, and Alq (50 Å) was deposited on the emission layer to form an ET-auxiliary layer, thereby forming a second light-emitting unit.

Then, Alq (50 Å) was deposited on the second light-emitting unit to form an electron transport layer, and LiF (15 Å) was deposited on the electron transport layer to form an electron injection layer, thereby forming an electron transport region.

Al (100 Å) was deposited on the electron transport region to form a cathode, thereby completing the manufacture of an organic light-emitting device:

Comparative Example 1

An organic light-emitting device was manufactured in the same manner as in Example 1, except that Compound ET1 and Li (having an amount of about 10 weight %) were used as materials for forming the n-type charge generation layer, and HATCN was used as a material for forming the p-type charge generation layer.

ET1

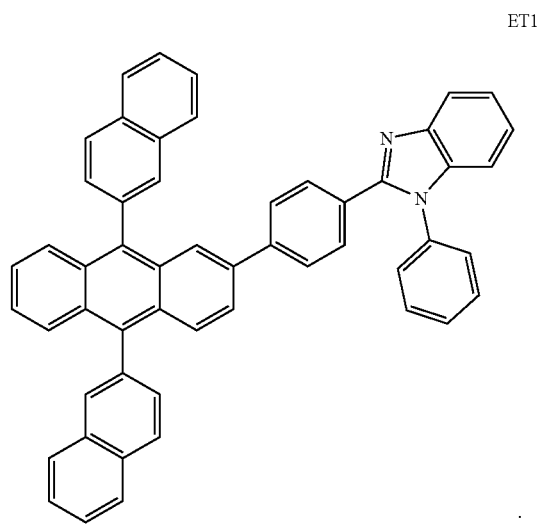 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

Evaluation Example 1

Figure 6:
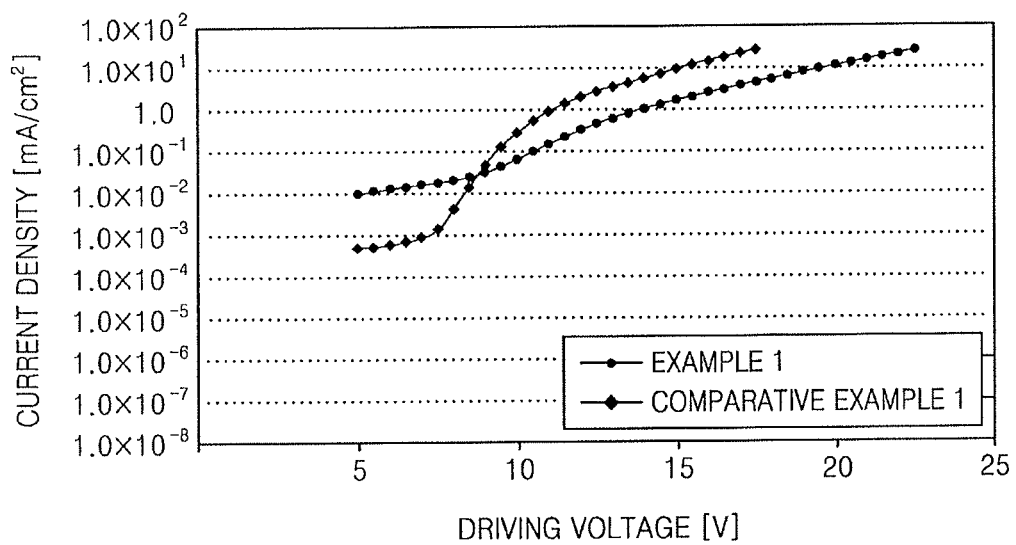
FIG. 6 illustrates a graph showing driving voltage (V)-dependent current density ($mA/cm^2$) of organic light-emitting devices prepared according to Example 1 and Comparative Example 1.
Figure 7:
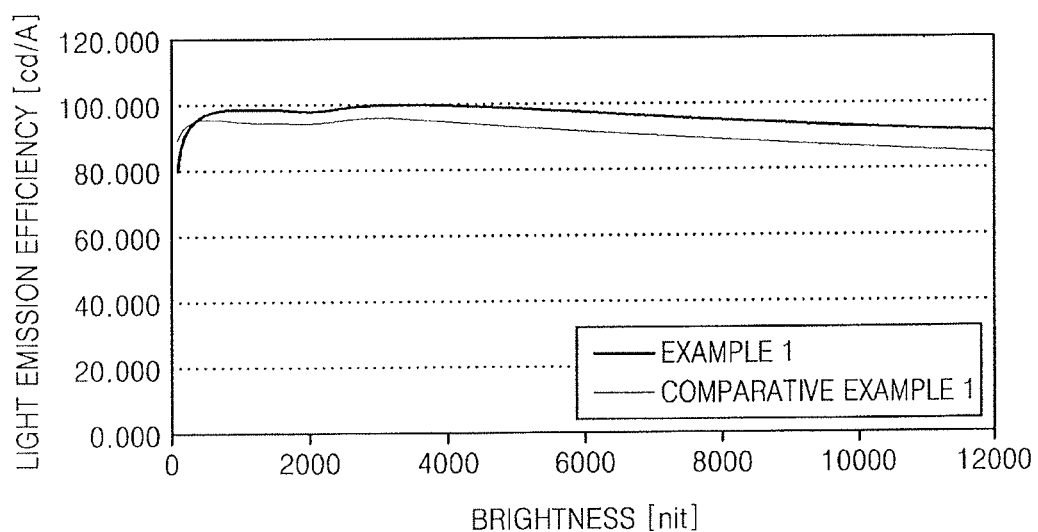
FIG. 7 illustrates a graph showing brightness-dependent light emission efficiency (cd/A) of organic light-emitting devices prepared according to Example 1 and Comparative Example 1.

Driving voltage (V)-dependent current density (mA/cm²) and brightness-dependent light emission efficiency (cd/A) of each of the organic light-emitting devices of Example 1 and Comparative Example 1 were measured, and results thereof are shown in Table 1 and FIGS. 6 and 7.

TABLE 1

|  | Current density (mA/cm²) at driving voltage of 6 V | Current density (mA/cm²) at driving voltage of 15 V | Efficiency (cd/A) at brightness of 2,000 nit | Efficiency (cd/A) at brightness of 1,000 nit |
|---|---|---|---|---|
| Example 1 | 0.0009 | 10 | 99 | 96 |
| Comparative Example 1 | 0.02 | 1.1 | 95 | 86 |

Referring to FIGS. 6 and 7 and Table 1, it was confirmed that the organic light-emitting device of Example 1 had improved effects in terms of reducing driving voltage and increasing light emission efficiency, compared to those of the organic light-emitting device of Comparative Example 1. In addition, it was confirmed that the light-emitting device of Example 1 showed a decrease in current leakage.

Example 2

An organic light-emitting device was manufactured in the same manner as in Example 1, except that Al was deposited to form an n-type charge generation layer having a thickness of about 2 nm, and Compound 2 was deposited to form a p-type charge generation layer:

(Compound 2)

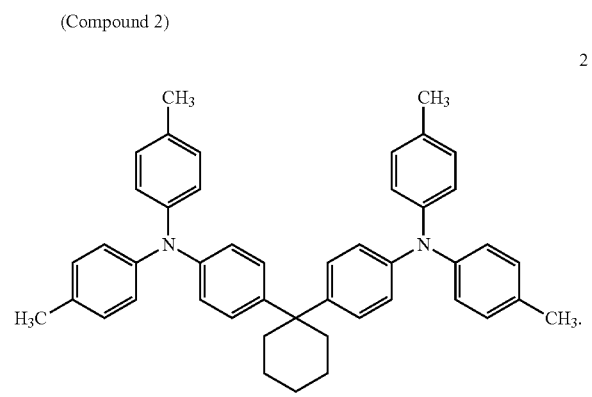

Comparative Example 2

An organic light-emitting device was manufactured in the same manner as in Example 2, except that HATCN was deposited to form the p-type charge generation layer.

Comparative Example 3

An organic light-emitting device was manufactured in the same manner as in Example 2, except that m-MTDATA (having an absolute value of a HOMO energy level of about 5.1 eV) was deposited to form the p-type charge generation layer.

Comparative Example 4

An organic light-emitting device was manufactured in the same manner as in Example 2, except that HATCN and m-MTDATA were co-deposited at a ratio of 5:5 to form the p-type charge generation layer.

Evaluation Example 2

Figure 8:
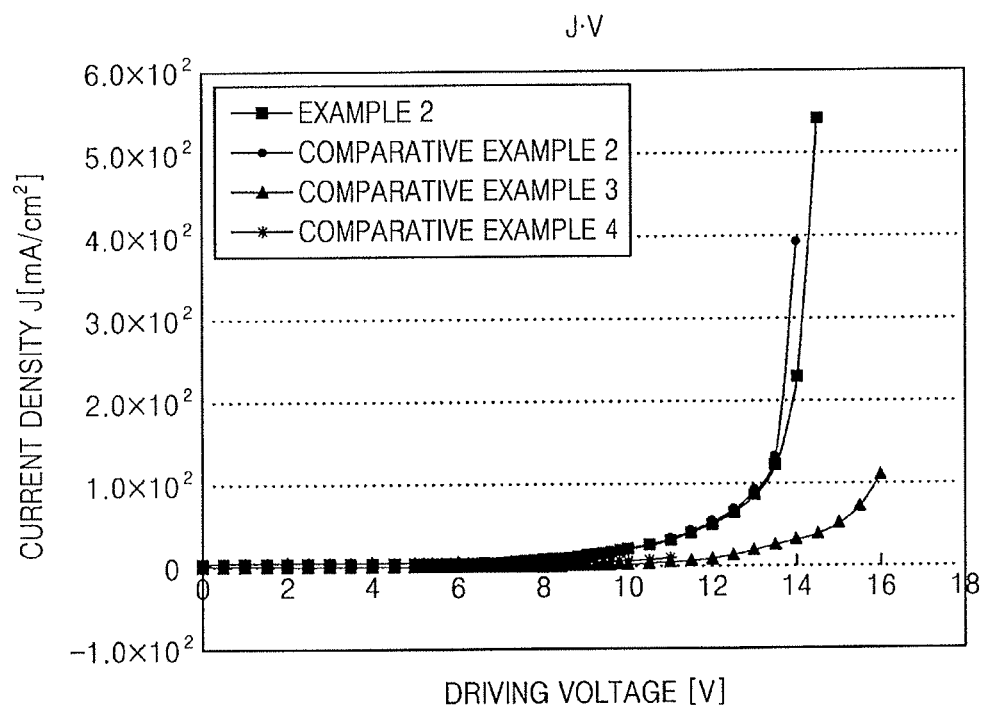
FIG. 8 illustrates a graph showing voltage (V)-dependent current density ($J(mA/cm^2)$) of organic light-emitting devices prepared according to Example 2 and Comparative Examples 2 to 4.
Figure 9:
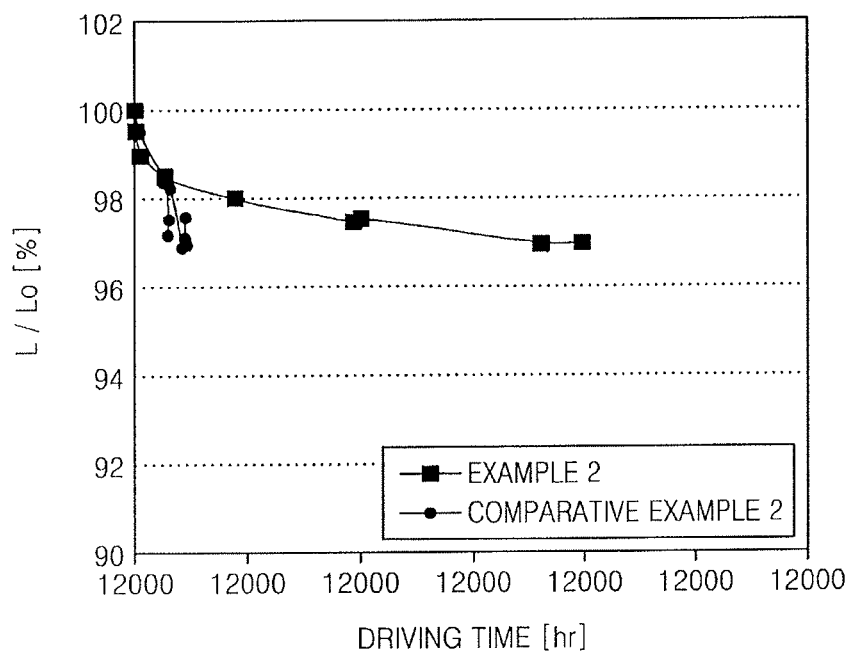
FIG. 9 illustrates a graph showing lateral leakage current of organic light-emitting devices prepared according to Example 2 and Comparative Example 2 relative to driving time.

Voltage (V)-dependent current density (J (mA/cm$^2$)) of each of the organic light-emitting devices of Example 2 and Comparative Examples 2 to 4 was measured, and results thereof are shown in Table 2 and FIG. 8, and lateral leakage current of each of the organic light-emitting devices of Example 2 and Comparative Examples 2 to 4 was measured relative to driving time, and results thereof are shown in Table 2 and FIG. 9. Here, lifespan (T$_{98}$) is the driving time taken for the organic light-emitting device to reach about 98% of its initial brightness.

TABLE 2

|  | Current density (mA/cm$^2$) at driving voltage of 10 V | Current density (mA/cm$^2$) at driving voltage of 12 V | Lifespan (T$_{98}$) (at 12,000 nit) (hr) |
|---|---|---|---|
| Example 2 | 19.7 | 52 | 44.6 |
| Comparative Example 2 | 19.7 | 52 | 15.7 |
| Comparative Example 3 | 1.2 | 7.5 | — |
| Comparative Example 4 | 2.56 | — | — |

Referring to Table 2 and FIGS. 8 and 9, it was confirmed that the organic light-emitting device of Example 2 maintained current characteristics and exhibited a long lifespan, compared to the organic light-emitting device of Comparative Example 2. In addition, it was confirmed that the organic light-emitting device of Example 2 showed a decrease in lateral leakage current, thereby increasing surface resistance while reducing conductivity.

In addition, referring to FIG. 8, it was confirmed that the organic light-emitting device of Example 2 exhibits excellent current characteristics, compared to those of the organic light-emitting devices of Comparative Examples 2 and 3.

Example 3

An organic light-emitting device was manufactured in the same manner as in Example 2, except that Yb was deposited to form an n-type charge generation layer having a thickness of about 2 nm.

Example 4

An organic light-emitting device was manufactured in the same manner as in Example 3, except that a first electron transport layer including ET1 and Yb in a ratio of 98:2 was formed under the n-type charge generation layer to a thickness of about 10 nm.

Comparative Example 5

An organic light-emitting device was manufactured in the same manner as in Example 3, except ET1 and Li (having an amount of 10 weight %) were deposited on the first light-emitting unit to form an n-type charge generation layer having a thickness of about 150 Å.

Evaluation Example 3

Figure 10:
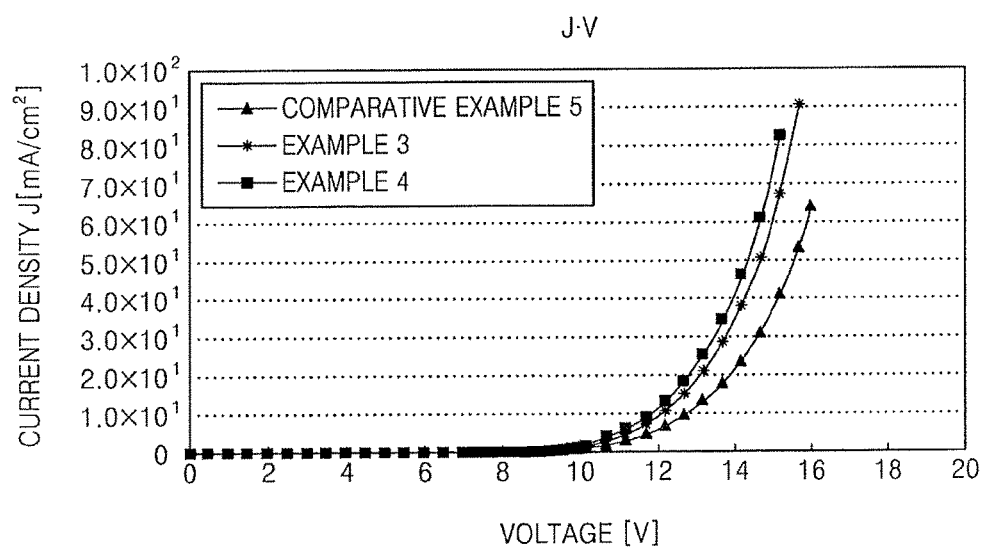
FIG. 10 illustrates a graph showing voltage (V)-dependent current density ($J(mA/cm^2)$) of organic light-emitting devices prepared according to Examples 3 and 4 and Comparative Example 5.

Voltage (V)-dependent current density (J(mA/cm$^2$) of each of the organic light-emitting devices of Examples 3 and 4 and Comparative Example 5 was measured, and results thereof are shown in Table 3 and FIG. 10.

TABLE 3

|  | Current density (mA/cm$^2$) at driving voltage of 12 V | Current density (mA/cm$^2$) at driving voltage of 15 V |
|---|---|---|
| Example 3 | 9.5 | 61 |
| Example 4 | 12 | 75 |
| Comparative Example 5 | 5.5 | 37 |

Referring to Table 3 and FIG. 10, it was confirmed that the organic light-emitting devices of Examples 3 and 4 showed improved current density and efficiency, compared to those of the organic light-emitting device of Comparative Example 5.

In particular, the organic light-emitting device of Example 4 showed a significantly decreased driving voltage, compared to that of the organic light-emitting device of Comparative Example 5, and accordingly, it was confirmed that a driving voltage of the organic light-emitting device further including the first electron transport layer and the second electron transport layer may significantly decrease.

As described above, embodiments may provide an organic light-emitting device having a low driving voltage, high efficiency, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light-emitting device, comprising:
a first electrode, a second electrode facing the first electrode, and a plurality of light-emitting units disposed in a stack between the first and second electrodes, each light emitting unit including an emission layer; and
a charge generation layer, including an n-type charge generation layer and a p-type charge generation layer, disposed between each adjacent pair of light-emitting units, wherein:
a wavelength of maximum intensity of light emitted from one of the light-emitting units is different from the wavelength of maximum intensity of light emitted from another of the light-emitting units,
at least one n-type charge generation layer consists of a metal-containing material having a work function of about 2.0 eV to about 4.5 eV, the metal-containing material being a metal, a metal oxide, a metal halide, or a combination thereof, and
at least one p-type charge generation layer includes a hole transport material,
at least one light-emitting unit adjacent to the p-type charge generation layer including the hole transport material includes a hole transport region,
the hole transport region includes a hole transport layer, an absolute value of a highest occupied molecular orbital (HOMO) energy level of the hole transport material being greater than about 5.5 eV, and an absolute value of a lowest unoccupied molecular orbital (LUMO) energy level of the hole transport material being less than that of a LUMO energy level of a hole transport layer of a light-emitting unit adjacent to the p-type charge generation layer.

2. The organic light-emitting device as claimed in claim 1, wherein the metal-containing material has a work function of about 2.5 eV to about 4.0 eV.

3. The organic light-emitting device as claimed in claim 1, wherein the metal-containing material includes at least one selected from ytterbium (Yb), silver (Ag), aluminum (Al), samarium (Sm), magnesium (Mg), lithium (Li), RbI, titanium (Ti), rubidium (Rb), sodium (Na), potassium (K), barium (Ba), manganese (Mn), and $YbSi_2$.

4. The organic light-emitting device as claimed in claim 1, wherein the absolute value of the HOMO energy level of the hole transport material is greater than an absolute value of a HOMO energy level of the hole transport layer.

5. The organic light-emitting device as claimed in claim 1, wherein the absolute value of the HOMO energy level of the hole transport material is about 5.5 eV to about 7.0 eV.

6. The organic light-emitting device as claimed in claim 1, wherein the hole transport material is formed from compounds that do not have a cyano group, the absolute value of the HOMO energy level of the hole transport material being about 5.5 eV to about 7.0 eV.

7. The organic light-emitting device as claimed in claim 1, wherein the hole transport material is selected from an amine-containing compound and a carbazole-containing compound, the absolute value of the HOMO energy level of the hole transport material being about 5.5 eV to about 7.0 eV.

8. The organic light-emitting device as claimed in claim 1, wherein the hole transport material is selected from compounds represented by Formulae 201, 202, and 301-2:

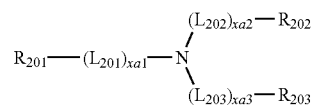

<Formula 201>

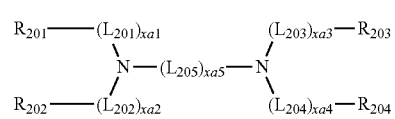

<Formula 202>

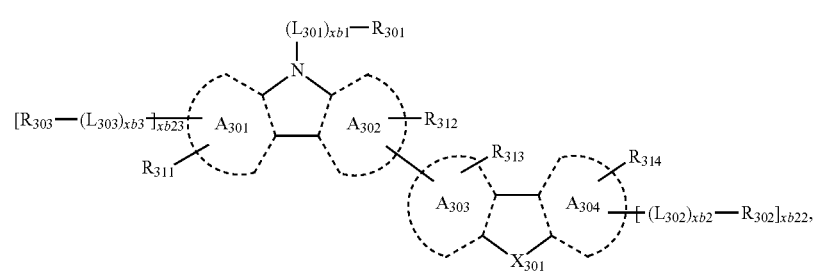

<Formula 301-2> wherein, in Formulae 201, 202, and 301-2, $A_{301}$ to $A_{304}$ are each independently selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ is O, S, or N-$[(L_{304})_{xb4}$-$R_{304}]$, $L_{201}$ to $L_{204}$ and $L_{301}$ to $L_{303}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ is selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 are each independently an integer of 0 to 3, xa5 is an integer of 1 to 10, xb1 to xb4 are each independently an integer of 0 to 5, xb22 and xb23 are each independently 0, 1, or 2, $R_{201}$ to $R_{204}$ and $Q_{201}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{301}$ to $R_{304}$ are each independently selected from deuterium, —F, —Cl, —Br, —I, a hydroxyl group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), $R_{311}$ to $R_{314}$ are each independently selected from hydrogen, deuterium, —F, —Cl, —Br, —I, a hydroxyl group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ and $Q_{301}$ to $Q_{303}$ are each independently selected from a $C_1$-$C_{10}$ alkyl group, a $C_1$-$C_{10}$ alkoxy group, a phenyl group, a biphenyl group, a terphenyl group, and a naphthyl group.

9. The organic light-emitting device as claimed in claim 1, wherein at least one p-type charge generation layer consists of the hole transport material.

10. The organic light-emitting device as claimed in claim 1, further comprising a first electron transport layer, the first electron transport layer being disposed between an n-type charge generation layer and an adjacent light-emitting unit, wherein:
the first electron transport layer includes an electron transport material and a metal-containing material, and
the metal-containing material includes a metal, a metal oxide, a metal halide, or a combination thereof.

11. The organic light-emitting device as claimed in claim 10, wherein an amount of the electron transport material of the electron transport layer is greater than an amount of the metal-containing material.

12. The organic light-emitting device as claimed in claim 10, wherein the electron transport material in the first electron transport layer includes at least one π electron-depleted nitrogen-containing ring.

13. The organic light-emitting device as claimed in claim 10, wherein an n-type charge generation layer includes a same metal-containing material as the first electron transport layer.

14. The organic light-emitting device as claimed in claim 10, further comprising a second electron transport layer disposed between the first electron transport layer and an adjacent light-emitting unit, the second electron transport layer including an electron transport material.

15. The organic light-emitting device as claimed in claim 1, wherein 2 or 3 light emitting units are disposed between the first and second electrodes.

16. The organic light-emitting device as claimed in claim 1, wherein:
two light emitting units are disposed between the first and second electrodes, the two light emitting units being a first light-emitting unit and a second light-emitting unit, the charge generation layer being disposed between the first light-emitting unit and the second light-emitting unit, the first light-emitting unit is disposed between the first electrode and the charge generation layer, and the second light-emitting unit is disposed between the charge generation layer and the second electrode, the n-type charge generation layer is disposed between the first light-emitting unit and the second light-emitting unit, and the p-type charge generation layer is disposed between the n-type charge generation layer and the second light-emitting unit, the n-type charge generation layer consists of the metal-containing material, the p-type charge generation layer includes the hole transport material, the second light-emitting unit includes a hole transport layer, the p-type charge generation layer is adjacent to the hole transport layer of the second light-emitting unit, an absolute value of a HOMO energy level of the hole transport material of the p-type charge generation layer is greater than about 5.5 eV, and an absolute value of a LUMO energy level of the hole transport material of the p-type charge generation layer is less than that of a LUMO energy level of the hole transport layer of the second light-emitting unit.

17. The organic light-emitting device as claimed in claim 16, wherein the absolute value of the HOMO energy level of the hole transport material is the same as or greater than the absolute value of a HOMO energy level of the hole transport layer of the second light-emitting unit.

18. The organic light-emitting device as claimed in claim 16, further comprising a first electron transport layer disposed between the n-type charge generation layer and the first light-emitting unit, wherein:

the first electron transport layer includes an electron transport material and a metal-containing material, and the metal-containing material includes a metal, a metal oxide, a metal halide, or a combination thereof.

19. The organic light-emitting device as claimed in claim 18, further comprising a second electron transport layer disposed between the first electron transport layer and the first light-emitting unit, the second electron transport layer including an electron transport material.

20. The organic light-emitting device as claimed in claim 1, wherein:

three light emitting units are disposed between the first and second electrodes, the three light emitting units being a first light-emitting unit, a second light-emitting unit, and a third light-emitting unit, a first charge generation layer is disposed between the first light-emitting unit and the second light-emitting unit, and a second charge generation layer is disposed between the second light-emitting unit and the third light-emitting unit, the first light-emitting unit is disposed between the first electrode and the first charge generation layer, the second light-emitting unit is disposed between the first charge generation layer and the second charge generation layer, and the third light-emitting unit is disposed between the second charge generation layer and the second electrode, the first charge generation layer includes a first n-type charge generation layer and a first p-type charge generation layer, the first n-type charge generation layer being disposed between the first light-emitting unit and the second light-emitting unit, and the first p-type charge generation layer being disposed between the first n-type charge generation layer and the second light-emitting unit, the second charge generation layer includes a second n-type charge generation layer and a second p-type charge generation layer, the second n-type charge generation layer being disposed between the second light-emitting unit and the third light-emitting unit, and the second p-type charge generation layer being disposed between the second n-type charge generation layer and the third light-emitting unit, the first n-type charge generation layer or the second n-type charge generation layer consists of the metal-containing material, the first p-type charge generation layer or the second p-type charge generation layer includes the hole transport material, the second light-emitting unit or the third light-emitting unit includes the hole transport layer, the first p-type charge generation layer is adjacent to the hole transport layer of the second light-emitting unit, or the second p-type charge generation layer is adjacent to the hole transport layer of the third light-emitting unit, an absolute value of a HOMO energy level of the hole transport material of the first p-type charge generation layer or the second p-type charge generation layer is greater than about 5.5 eV, and an absolute value of a LUMO energy level of the hole transport material of the first p-type charge generation layer is less than the absolute value of a LUMO energy level of the hole transport layer of the second light-emitting unit, or an absolute value of a LUMO energy level of the hole transport material of the second p-type charge generation layer is less than that of a LUMO energy level of the hole transport layer of the third light-emitting unit.

* * * * *